(12) United States Patent
Kendall et al.

(10) Patent No.: US 12,048,558 B2
(45) Date of Patent: Jul. 30, 2024

(54) SYSTEM FOR DETERMINING FLUID LEVEL IN A BIOLOGICAL SUBJECT

(71) Applicant: WearOptimo Pty Ltd, Milton (AU)

(72) Inventors: Mark Anthony Fernance Kendall, Woolloongabba (AU); Stephen James Wilson, Woolloongabba (AU); Anthony Mark Brewer, Woolloongabba (AU)

(73) Assignee: WearOptimo Pty Ltd, Milton (AU)

( * ) Notice: Subject to any disclaimer, the term of this patent is extended or adjusted under 35 U.S.C. 154(b) by 0 days.

(21) Appl. No.: 17/042,798

(22) PCT Filed: Oct. 1, 2019

(86) PCT No.: PCT/AU2019/051059
§ 371 (c)(1),
(2) Date: Sep. 28, 2020

(87) PCT Pub. No.: WO2020/069564
PCT Pub. Date: Apr. 9, 2020

(65) Prior Publication Data
US 2021/0077019 A1 Mar. 18, 2021

(30) Foreign Application Priority Data
Oct. 2, 2018 (AU) .................. 2018903709

(51) Int. Cl.
*A61B 5/00* (2006.01)
*A61B 5/145* (2006.01)
(Continued)

(52) U.S. Cl.
CPC .......... *A61B 5/4875* (2013.01); *A61B 5/0002* (2013.01); *A61B 5/14503* (2013.01);
(Continued)

(58) Field of Classification Search
CPC ... A61B 5/685; A61B 5/150984; A61B 5/157; A61B 5/150282; A61B 2562/028;
(Continued)

(56) References Cited

U.S. PATENT DOCUMENTS

| | | | |
|---|---|---|---|
| 4,969,468 | A | 11/1990 | Byers et al. |
| 5,582,981 | A | 12/1996 | Toole et al. |

(Continued)

FOREIGN PATENT DOCUMENTS

| | | |
|---|---|---|
| CN | 102660547 A | 9/2012 |
| CN | 102703455 A | 10/2012 |

(Continued)

OTHER PUBLICATIONS

Miller, Philip R. et al., Multiplexed microneedle-based biosensor array for characterization of metabolic acidosis, Talanta, Jan. 15, 2012, pp. 739-742, vol. 88, Elsevier.
(Continued)

*Primary Examiner* — Tse W Chen
*Assistant Examiner* — Michael A Catina
(74) *Attorney, Agent, or Firm* — Howard & Howard Attorneys PLLC

(57) ABSTRACT

A system for performing fluid level measurements on a biological subject, the system including at least one substrate including a plurality of microstructures configured to breach a stratum corneum of the subject, at least some microstructures including an electrode, a signal generator operatively connected to at least one microstructure to apply an electrical stimulatory signal to the at least one microstructure and at least one sensor operatively connected to at least one microstructure, the at least one sensor being configured to measure electrical response signals from at least one microstructure. The system also includes one or more electronic processing devices that determine measured
(Continued)

response signals, the response signals being at least partially indicative of a bioimpedance and perform an analysis at least in part using the measured response signals to determine at least one indicator at least partially indicative of fluid levels in the subject.

20 Claims, 40 Drawing Sheets

(51) Int. Cl.
| | | |
|---|---|---|
| A61B 5/1459 | (2006.01) | |
| A61B 5/1473 | (2006.01) | |
| A61B 5/251 | (2021.01) | |
| A61B 5/256 | (2021.01) | |
| A61B 5/257 | (2021.01) | |
| A61B 5/262 | (2021.01) | |
| A61B 5/263 | (2021.01) | |
| A61B 5/266 | (2021.01) | |
| A61B 5/277 | (2021.01) | |

(52) U.S. Cl.
CPC .......... *A61B 5/1451* (2013.01); *A61B 5/1459* (2013.01); *A61B 5/14735* (2013.01); *A61B 5/251* (2021.01); *A61B 5/256* (2021.01); *A61B 5/257* (2021.01); *A61B 5/262* (2021.01); *A61B 5/263* (2021.01); *A61B 5/266* (2021.01); *A61B 5/277* (2021.01); *A61B 5/685* (2013.01); *A61B 2560/063* (2013.01); *A61B 2562/028* (2013.01)

(58) Field of Classification Search
CPC .......... A61B 2562/046; A61B 5/1451; A61M 37/0015; A61M 2037/0053; A61M 2037/0046
See application file for complete search history.

(56) References Cited

U.S. PATENT DOCUMENTS

| | | | |
|---|---|---|---|
| 5,595,877 | A | 1/1997 | Gold et al. |
| 6,052,652 | A | 4/2000 | Lee |
| 6,091,975 | A * | 7/2000 | Daddona ............ A61B 5/14865 |
| | | | 600/309 |
| 6,256,533 | B1 | 7/2001 | Yuzhakov et al. |
| 6,267,724 | B1 | 7/2001 | Taylor |
| 6,558,361 | B1 | 5/2003 | Yeshurun |
| 6,589,202 | B1 | 7/2003 | Powell |
| 6,591,124 | B2 | 7/2003 | Sherman et al. |
| 6,908,453 | B2 | 6/2005 | Fleming et al. |
| 6,923,764 | B2 | 8/2005 | Aceti et al. |
| 6,972,013 | B1 | 12/2005 | Zhang et al. |
| 7,285,090 | B2 | 10/2007 | Stivoric et al. |
| 8,506,529 | B1 | 8/2013 | Yang |
| 8,543,179 | B2 | 9/2013 | Chen et al. |
| 8,588,884 | B2 | 11/2013 | Hegde et al. |
| 9,974,471 | B1 | 5/2018 | Kam et al. |
| 10,098,574 | B1 | 10/2018 | Kam |
| 2002/0028991 | A1 | 3/2002 | Thompson |
| 2002/0133129 | A1 | 9/2002 | Arias et al. |
| 2003/0162190 | A1 | 8/2003 | Gorenstein et al. |
| 2003/0181936 | A1* | 9/2003 | Trautman .......... A61M 37/0015 |
| | | | 606/186 |
| 2004/0006264 | A1 | 1/2004 | Mojarradi et al. |
| 2004/0039254 | A1 | 2/2004 | Stivoric et al. |
| 2005/0070778 | A1 | 3/2005 | Lackey et al. |
| 2005/0261606 | A1 | 11/2005 | Sohrab |
| 2005/0261632 | A1 | 11/2005 | Xu |
| 2006/0172320 | A1 | 8/2006 | Stojanovic |
| 2006/0264782 | A1 | 11/2006 | Holmes et al. |
| 2007/0020641 | A1 | 1/2007 | Heeger et al. |
| 2007/0134721 | A1 | 6/2007 | Laitenberger et al. |
| 2007/0142885 | A1 | 6/2007 | Hantash et al. |
| 2007/0276211 | A1 | 11/2007 | Mir et al. |
| 2008/0009763 | A1 | 1/2008 | Chiou et al. |
| 2008/0221407 | A1 | 9/2008 | Baker |
| 2009/0062752 | A1 | 3/2009 | Gonnelli |
| 2010/0075432 | A1 | 3/2010 | Piletsky et al. |
| 2010/0100005 | A1 | 4/2010 | Mir et al. |
| 2010/0121163 | A1 | 5/2010 | Vestel et al. |
| 2010/0256524 | A1 | 10/2010 | Levinson et al. |
| 2010/0286491 | A1* | 11/2010 | Chen .................... A61B 5/0059 |
| | | | 600/301 |
| 2011/0105871 | A1 | 5/2011 | Zimmermann et al. |
| 2011/0125058 | A1 | 5/2011 | Levinson et al. |
| 2011/0224515 | A1 | 9/2011 | Mir et al. |
| 2011/0295100 | A1* | 12/2011 | Hegde ................... A61B 5/291 |
| | | | 600/391 |
| 2011/0318846 | A1 | 12/2011 | Lee et al. |
| 2011/0319786 | A1 | 12/2011 | Rebello et al. |
| 2012/0040865 | A1 | 2/2012 | Kim |
| 2012/0135540 | A1 | 5/2012 | Bruno |
| 2012/0316326 | A1 | 12/2012 | Ban et al. |
| 2013/0225956 | A1 | 8/2013 | Huang et al. |
| 2013/0338746 | A1 | 12/2013 | Guvanasen et al. |
| 2014/0259652 | A1 | 9/2014 | Pushpala et al. |
| 2015/0208984 | A1 | 7/2015 | Huang |
| 2015/0247816 | A1 | 9/2015 | Bhansali et al. |
| 2015/0257685 | A1 | 9/2015 | Pushpala et al. |
| 2015/0335288 | A1* | 11/2015 | Toth ..................... A61B 5/6833 |
| | | | 600/373 |
| 2015/0351690 | A1* | 12/2015 | Toth ..................... A61B 5/296 |
| | | | 600/373 |
| 2016/0029962 | A1 | 2/2016 | Hyde et al. |
| 2016/0051195 | A1 | 2/2016 | Pang et al. |
| 2016/0131668 | A1 | 5/2016 | Roncancio et al. |
| 2016/0166184 | A1 | 6/2016 | Teng et al. |
| 2016/0166185 | A1 | 6/2016 | Liepmann et al. |
| 2016/0256091 | A1 | 9/2016 | Cho et al. |
| 2016/0278638 | A1 | 9/2016 | Schwartz et al. |
| 2016/0278672 | A1* | 9/2016 | Cho ...................... A61B 5/685 |
| 2016/0302687 | A1 | 10/2016 | Lee et al. |
| 2016/0331290 | A1 | 11/2016 | Oh et al. |
| 2016/0338639 | A1 | 11/2016 | Myers et al. |
| 2016/0345872 | A1 | 12/2016 | Wasson et al. |
| 2017/0128009 | A1 | 5/2017 | Pushpala et al. |
| 2017/0233738 | A1 | 8/2017 | Jackson |
| 2017/0347925 | A1 | 12/2017 | Wang et al. |
| 2018/0059099 | A1 | 3/2018 | Kaushik et al. |
| 2018/0177439 | A1 | 6/2018 | Sia et al. |
| 2018/0327746 | A1 | 11/2018 | Minagawa et al. |
| 2018/0338713 | A1 | 11/2018 | Polsky et al. |
| 2019/0013425 | A1 | 1/2019 | Huang |
| 2019/0125223 | A1 | 5/2019 | Wang et al. |
| 2019/0219595 | A1 | 7/2019 | Leung |
| 2019/0256852 | A1 | 8/2019 | Xiao et al. |
| 2019/0328938 | A1 | 10/2019 | Son |
| 2020/0081001 | A1 | 3/2020 | Cleveland et al. |
| 2020/0172907 | A1 | 6/2020 | Yang et al. |
| 2021/0077019 | A1 | 3/2021 | Kendall et al. |

FOREIGN PATENT DOCUMENTS

| | | |
|---|---|---|
| CN | 104745585 A | 7/2015 |
| CN | 105136754 A | 12/2015 |
| CN | 105349545 A | 2/2016 |
| CN | 106618598 A | 5/2017 |
| EP | 1 266 608 A2 | 12/2002 |
| EP | 1 006 868 B1 | 6/2004 |
| EP | 2 532 749 A1 | 12/2012 |
| EP | 2 898 821 A1 | 7/2015 |
| EP | 2 898 921 A1 | 7/2015 |
| EP | 3 517 023 | 7/2019 |
| EP | 3 564 672 A1 | 11/2019 |
| JP | 2001-523993 A | 11/2001 |
| JP | 2003-501161 A | 1/2003 |
| JP | 2003-501163 A | 1/2003 |
| JP | 2004-526581 A | 9/2004 |
| JP | 2009-519062 A | 5/2009 |
| JP | 4672142 B2 | 1/2011 |
| JP | 2013-512062 A | 4/2013 |

(56) References Cited

FOREIGN PATENT DOCUMENTS

| | | |
|---|---|---|
| JP | 2014-533523 A | 12/2014 |
| KR | 20170041375 A | 10/2015 |
| KR | 10-2016-0021488 A | 2/2016 |
| KR | 20170041473 | 4/2017 |
| WO | 1998/46124 | 10/1998 |
| WO | 2000/074763 | 12/2000 |
| WO | 2000/074766 | 12/2000 |
| WO | 03/050290 A2 | 6/2003 |
| WO | 2005/060621 A2 | 7/2005 |
| WO | 2005/072630 | 8/2005 |
| WO | 2006101798 A2 | 9/2006 |
| WO | 2006/116242 A2 | 11/2006 |
| WO | 2009/012420 A1 | 1/2009 |
| WO | 2009/140735 | 11/2009 |
| WO | 2010/070619 A1 | 6/2010 |
| WO | 2012/130948 A1 | 10/2012 |
| WO | 2013/058879 | 4/2013 |
| WO | 2013/058879 A2 | 4/2013 |
| WO | 2014/120114 A1 | 8/2014 |
| WO | 2014/143427 A1 | 9/2014 |
| WO | 2014/159669 A2 | 10/2014 |
| WO | 2014/197822 | 12/2014 |
| WO | 2015/197706 A1 | 12/2015 |
| WO | 2016/009228 | 1/2016 |
| WO | 2016/009228 A1 | 1/2016 |
| WO | 2016/019250 | 2/2016 |
| WO | 2017/156223 A1 | 9/2017 |
| WO | 2017/164982 A1 | 9/2017 |
| WO | 2017/210683 A1 | 12/2017 |
| WO | 2018/017196 | 1/2018 |
| WO | 2018/026931 A1 | 2/2018 |
| WO | 2018/031559 A1 | 2/2018 |
| WO | 2018/037407 | 3/2018 |
| WO | 2018/124327 | 7/2018 |
| WO | 2018/202922 A1 | 11/2018 |
| WO | 2018/223105 A2 | 12/2018 |
| WO | 2018/237380 A1 | 12/2018 |
| WO | 2019/032461 | 2/2019 |
| WO | 2019/050933 A1 | 3/2019 |
| WO | 2019/067383 A1 | 4/2019 |
| WO | 2019/094315 A1 | 5/2019 |
| WO | 2019/099856 A1 | 5/2019 |
| WO | 2019/121324 | 6/2019 |
| WO | 2019/143923 A1 | 7/2019 |
| WO | 2019/170775 A1 | 9/2019 |
| WO | 2019/186129 | 10/2019 |
| WO | 2019/190596 | 10/2019 |
| WO | 2020/069564 A1 | 4/2020 |
| WO | 2020/069565 A1 | 4/2020 |
| WO | 2020/069567 A1 | 4/2020 |
| WO | 2020/069568 A1 | 4/2020 |
| WO | 2020/069570 A1 | 4/2020 |
| WO | 2020/102277 A1 | 5/2020 |

OTHER PUBLICATIONS

Miller, Philip R. et al., Integrated carbon fiber electrodes within hollow polymer microneedles for transdermal electrochemical sensing, Biomicrofluidics, 2011, pp. 013415-1 to 013415-14, vol. 5, No. 1.

Szeitner, Zsuzsanna et al., A rational approach for generating cardiac troponin I selective Spiegelmers, The Royal Society of Chemistry, 2014, pp. 6801-6804, vol. 50.

Xiao, Yi et al., Preparation of electrode-immobilied, redox-modified oligonucleotides for electrochemical DNA and aptamer-based sensing, Nature Protocols, 2007, pp. 2875-2880, vol. 2, No. 11, Santa Barbara, California.

Xiao, Yi et al., Label-Free Electronic Detection of Thrombin in Blood Serum by Using an Aptamer-Based Sensor, Angew. Chem. Int. Ed., 2005, pp. 5456-5459, vol. 44, Wiley-VCH Verlag GmbH 7 Co. KGaA, Weinheim.

Pfeiffer, Franziska et al., Selection and Biosensor Application of Aptamers for Small Molecules, Frontiers in Chemistry, Jun. 15, 2016, 21 pages, vol. 4, Bonn, Germany.

Negahdary, M. et al., Electrochemical aptasensing of human cardiac troponin I based on an array of gold nanodumbells—Applied to early detection of myocardial infarction, Elsevier, 2017, pp. 62-71.

Stojanovic, Milan N. et al., Fluorescent Sensors Based on Aptamer Self-Assembly, American Chemical Society, 2000, pp. 11547-11548, vol. 122.

Gupta, Shashi et al., Chemically Modified DNA Aptamers Bind Interleukin-6 with High Affinity and Inhibit Signaling by Blocking Its Interaction with Interleukin-6 Receptor, The Journal of Biological Chemistry, Mar. 21, 2014, pp. 8706-8719, vol. 289, No. 12, USA.

Jo, Hunho et al., Electrochemical Aptasensor of Cardiac Troponin I for the Early Diagnosis of Acute Myocardial Infarction, analytical chemistry, 2015, pp. 9869-9875, vol. 87, ACS Publications.

Negahdary, M. et al., An Aptamer-based Biosensor for Troponin I Detection in Diagnosis of Myocardial Infarction, J Biomed Phys Eng, 2018, pp. 167-178, vol. 8, No. 2.

Mishra, Geetesh Kumar et al., Electrochemical Aptasensors for Food and Environmental Safeguarding: A Review, Biosensors, Mar. 23, 2018, pp. 1-13, vol. 8, No. 28.

Meng, Ellis et al., Plasma Removal of Parylene C, Journal of Micromechanics and Microengineering, Feb. 22, 2008, pp. 1-13, vol. 18, IOP Publishing.

Liu, Ying et al., Aptamer-Based Electrochemical Biosensor for Interferon Gamma Detection, Analytical Chemistry, Oct. 1, 2010, pp. 8131-8136, vol. 82, No. 19.

Kumar, L.S. Selva et al., Label free nano-aptasensor for interleukin-6 in protein-dilute bio fluids such as sweat, Analytical Methods, 2015, pp. 1-5, vol. xx.

Lai, Rebecca Y. et al., Comparison of the Signaling and Stability of Electrochemical DNA Sensors Fabricated from 6- or 11-Carbon Self-Assembled Monolayers, Lanmuir, Jun. 13, 2006, pp. 10796-10800, vol. 22, Santa Barbara, California.

Hirota, Masao et al., Chemically Modified Interleukin-6 Aptamer Inhibits Development of Collagen-Induced Arthritis n Cynomolgus Monkeys, Nucleic Acid Therapeutics, 2016, pp. 10-20, vol. 26, No. 1, Mary Ann Liebert, Inc.

Ricci, Francesco et al., Using Nature's "Tricks" to Rationally Tune the Binding Properties of Biomolecular Receptors, American Chemical Society, Aug. 26, 2016, pp. 1884-1892, vol. 49, ACS Publications.

* cited by examiner

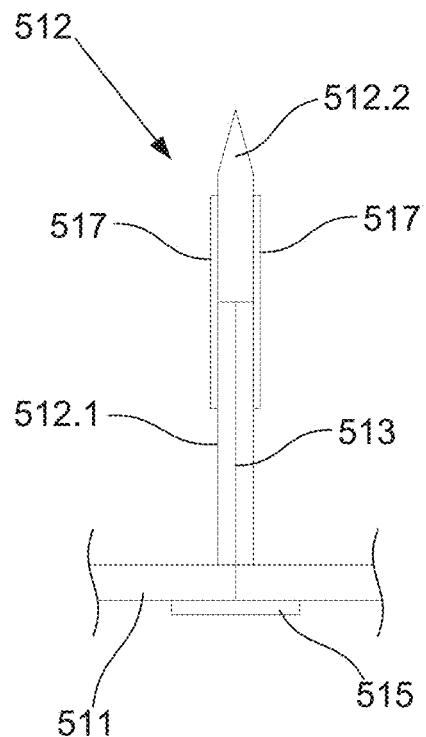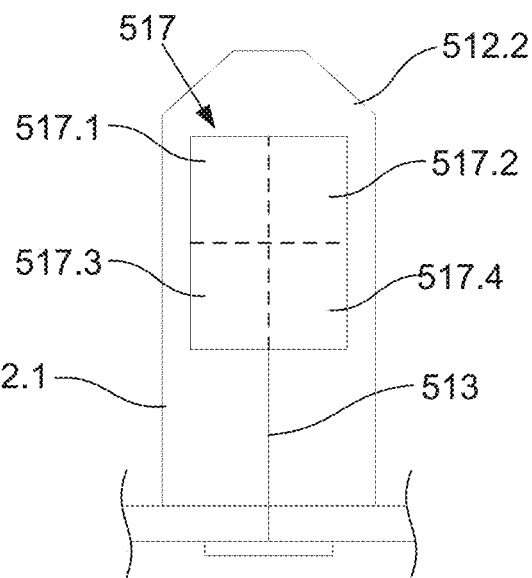
Fig. 5A Fig. 5B
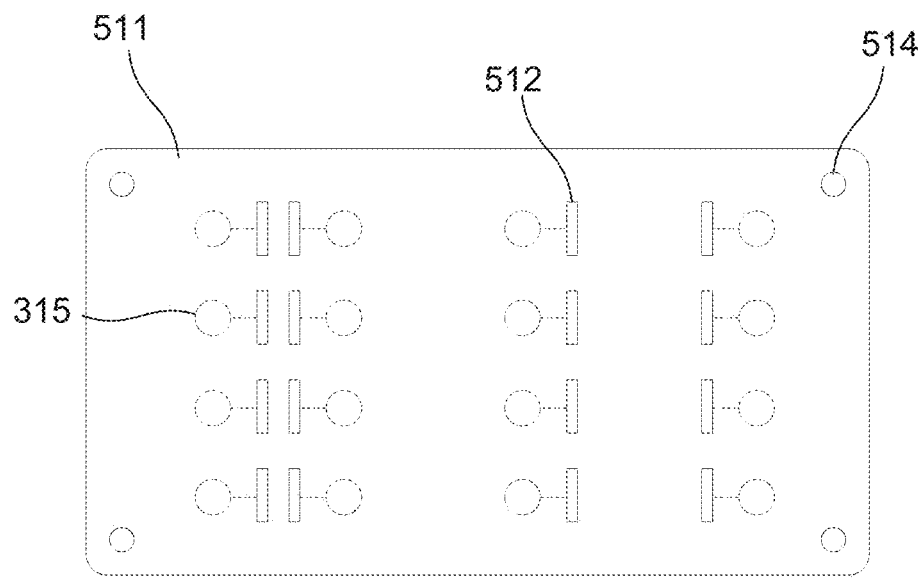
Fig. 5C

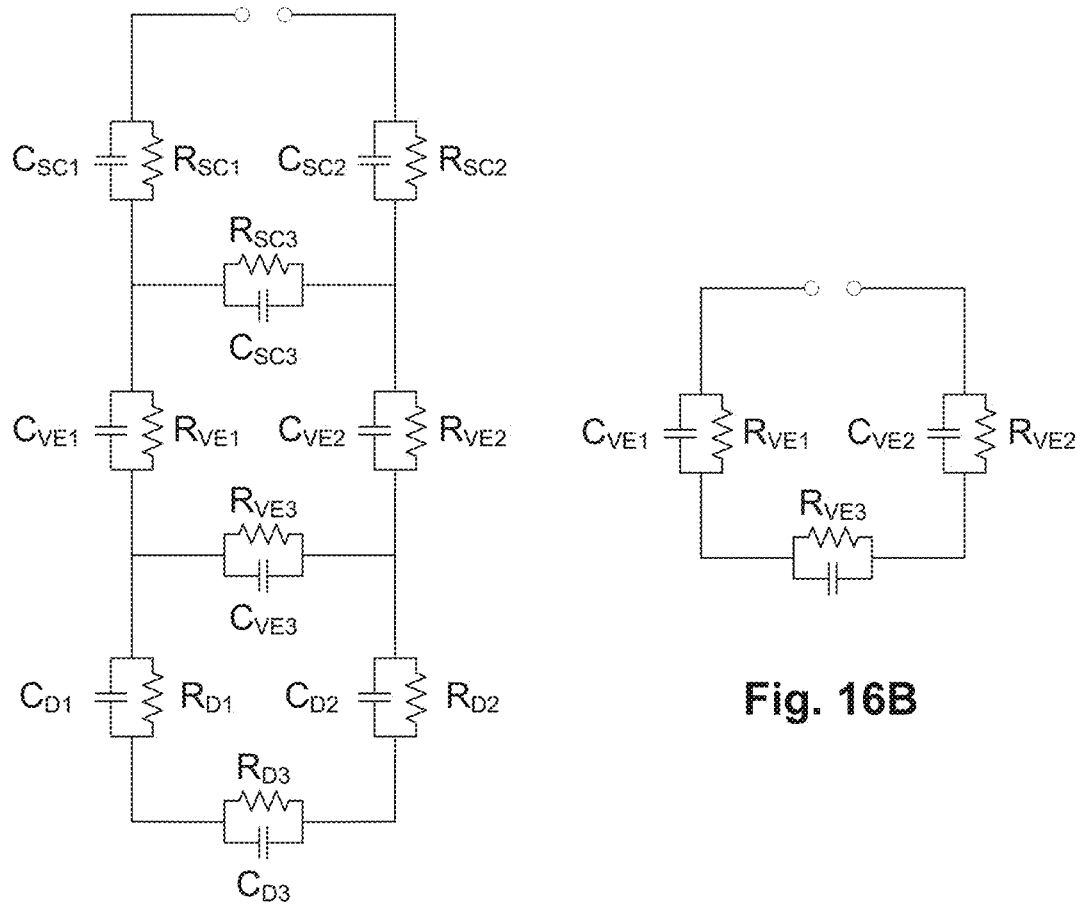
Fig. 16A
Fig. 16B
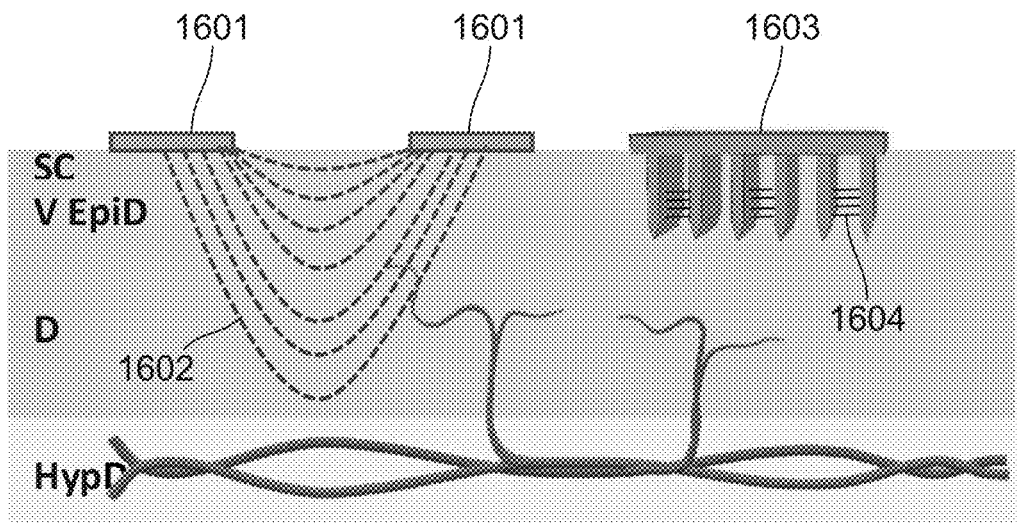
Fig. 16C

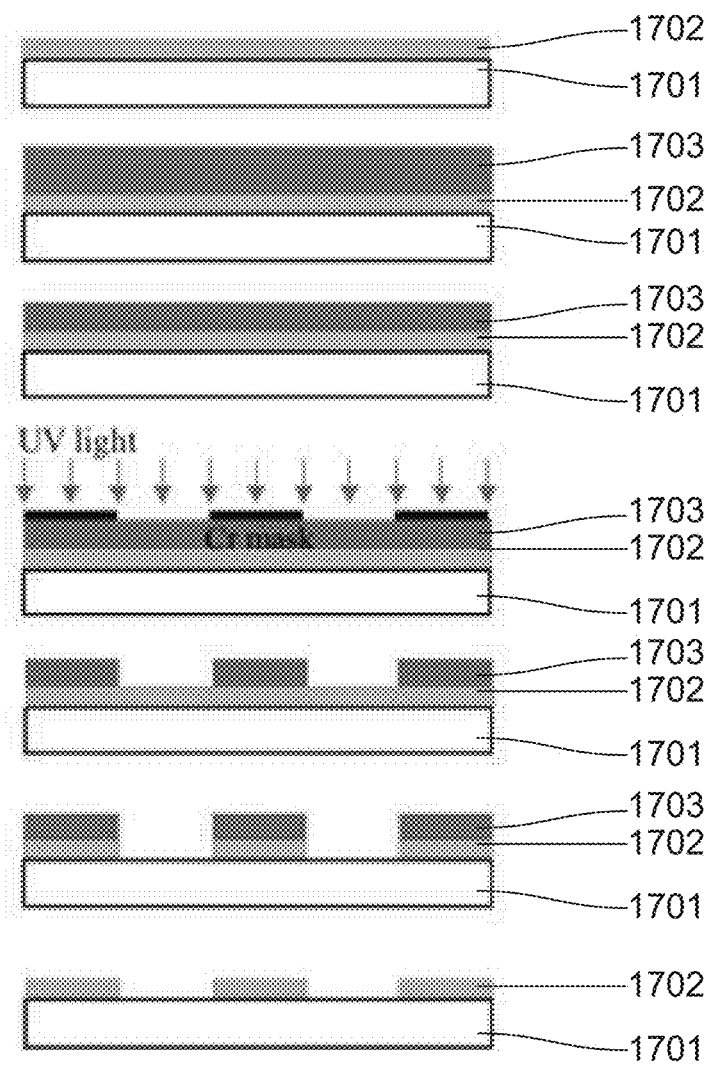

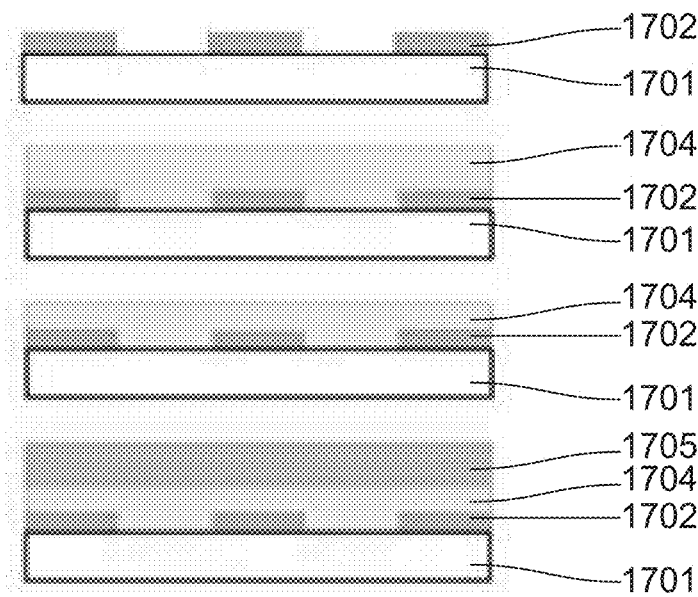
Fig. 17H
Fig. 17I
Fig. 17J
Fig. 17K
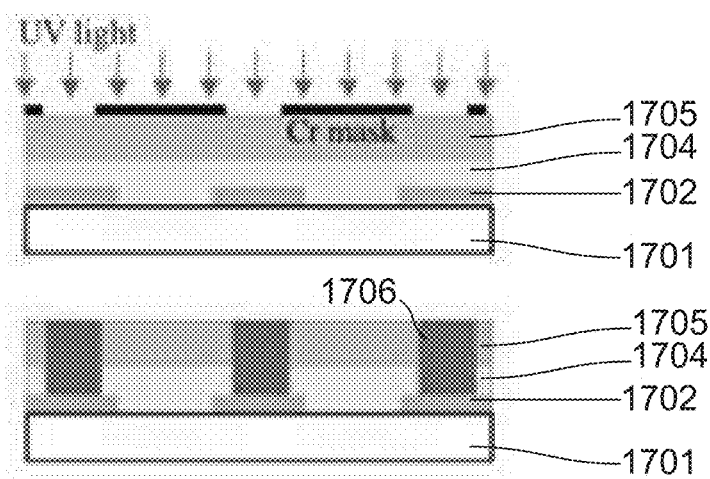
Fig. 17L
Fig. 17M
Fig. 17N
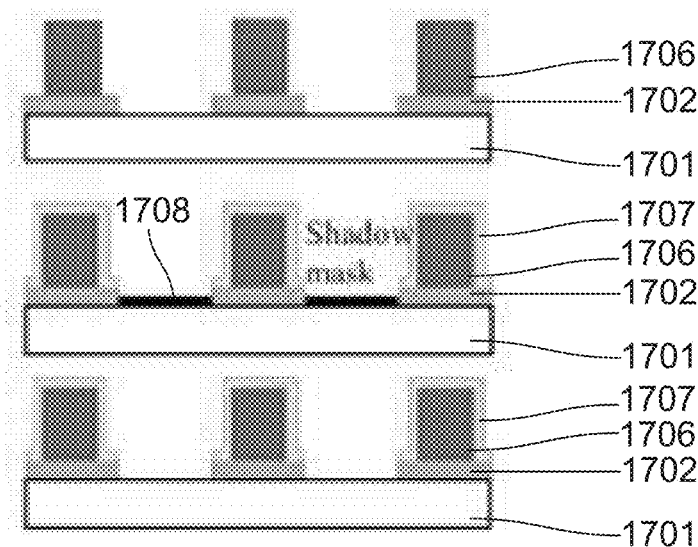
Fig. 17O
Fig. 17P

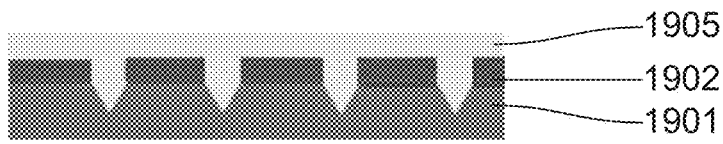
Fig. 19H
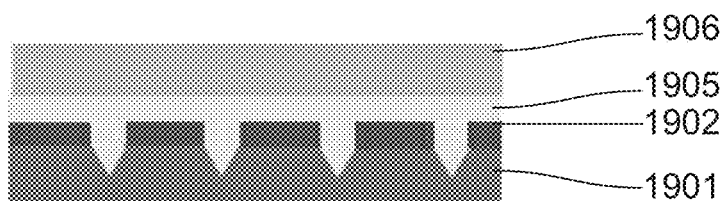
Fig. 19I
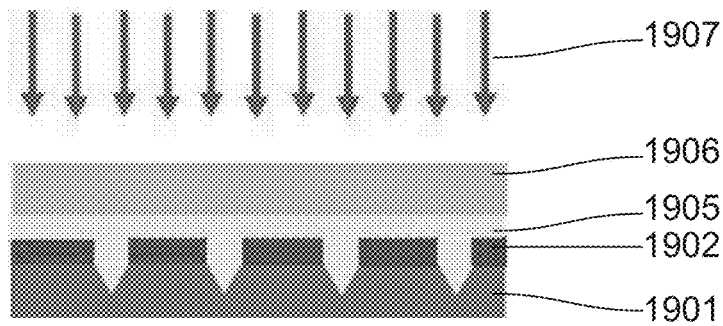
Fig. 19J
Fig. 19K
Fig. 19L
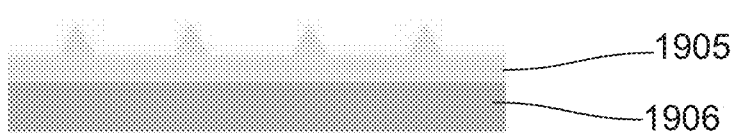

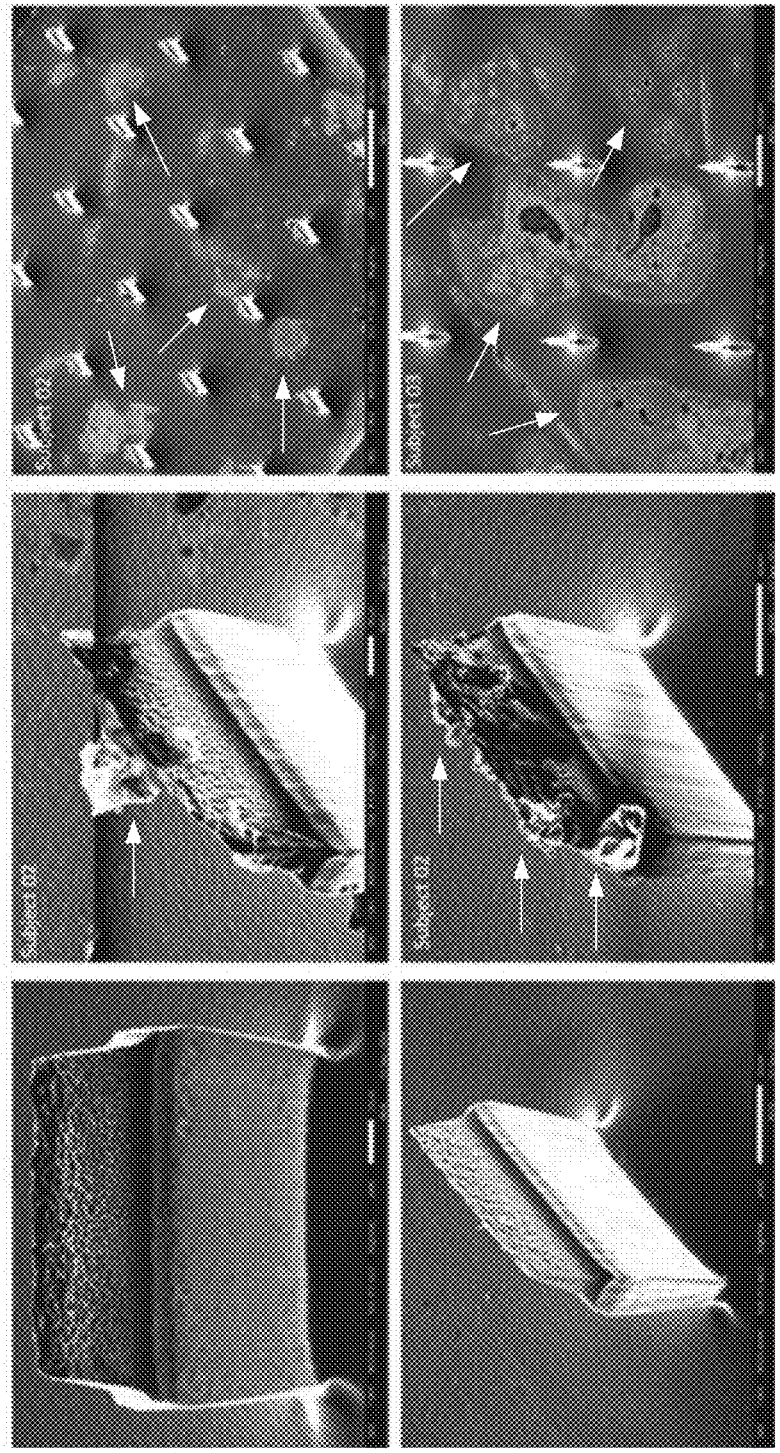

SYSTEM FOR DETERMINING FLUID LEVEL IN A BIOLOGICAL SUBJECT

CROSS-REFERENCE TO RELATED APPLICATIONS

The present application is the National Stage of International Patent Application No. PCT/AU2019/051059, filed Oct. 1, 2019, which claims priority to and all the benefits of Australian Patent Application No. 2018903709, filed Oct. 2, 2018, all disclosures of which are expressly incorporated herein by reference in their entirety.

BACKGROUND OF THE INVENTION

The present invention relates to a system and method for performing measurements on a biological subject, and in one particular example, to performing measurements of fluid levels on a biological subject by breaching a stratum corneum of the subject using microstructures.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to use impedance measurements to perform body composition and/or total body water measurements on a biological subject. Such arrangements typically utilise surface based electrodes to apply a current through tissue, with a potential across the tissue being measured and used to derive an impedance measurement. Analysis of the impedance measurement can then be used to derive information regarding fluid levels in the subject, such as levels of intra-cellular and/or extra-cellular.

US20110295100 describes methods, systems and/or devices for enhancing conductivity of an electrical signal through a subject's skin using one or more microneedle electrodes are provided. A microneedle electrode may be applied to the subject's skin by placing the microneedle electrode in direct contact with the subject's skin. The microneedles of the microneedle electrode may be inserted into the skin such that the microneedles pierce stratum corneum of the skin up to or through dermis of the skin. An electrical signal passes or is conducted through or across the microneedle electrode and the subject's skin, where impedance of the microneedle electrode is minimal and greatly reduced compared to existing technologies.

US 2019/0013425 describes a biometric information measuring sensor is provided that includes a base comprising a plurality of bio-marker measuring areas and a plurality of electrodes. Each of the plurality of electrodes is disposed on a respective one of the plurality of bio-marker measuring areas, and each of the plurality of electrodes includes a working electrode and a counter electrode spaced apart from the working electrode. The biometric information measuring sensor also includes a plurality of needles. Each of the needles is disposed on a respective one of the plurality of electrodes. Two or more of the plurality of needles have different lengths.

US20150208984 describes a transdermal microneedle continuous monitoring system. The continuous system monitoring includes a substrate, a microneedle unit, a signal processing unit and a power supply unit. The microneedle unit at least comprises a first microneedle set used as a working electrode and a second microneedle set used as a reference electrode, the first and second microneedle sets arranging on the substrate. Each microneedle set comprises at least a microneedle. The first microneedle set comprises at least a sheet having a through hole on which a barbule forms at the edge. One of the sheets provides the through hole from which the barbules at the edge of the other sheets go through, and the barbules are disposed separately.

U.S. Pat. No. 8,588,884 describes devices for enhancing conductivity of an electrical signal through a subject's skin using one or more microneedle electrodes are provided. A microneedle electrode may be applied to the subject's skin by placing the microneedle electrode in direct contact with the subject's skin. The microneedles of the microneedle electrode may be inserted into the skin such that the microneedles pierce stratum corneum of the skin up to or through dermis of the skin. An electrical signal passes or is conducted through or across the microneedle electrode and the subject's skin, where impedance of the microneedle electrode is minimal and greatly reduced compared to existing technologies.

SUMMARY OF THE PRESENT INVENTION

In one broad form, an aspect of the present invention seeks to provide a system for performing fluid level measurements on a biological subject, the system including: at least one substrate including a plurality of microstructures configured to breach a stratum corneum of the subject, at least some microstructures including an electrode; a signal generator operatively connected to at least one microstructure to apply an electrical stimulatory signal to the at least one microstructure; at least one sensor operatively connected to at least one microstructure, the at least one sensor being configured to measure electrical response signals from at least one microstructure; and, one or more electronic processing devices that are configured to: determine measured response signals, the response signals being at least partially indicative of a bioimpedance; and, perform an analysis at least in part using the measured response signals to determine at least one indicator at least partially indicative of fluid levels in the subject.

In one broad form, an aspect of the present invention seeks to provide a method for performing fluid level measurements on a biological subject, the method including: using at least one substrate including a plurality of microstructures to breach a stratum corneum of the subject, at least some microstructures including an electrode; using a signal generator operatively connected to at least one microstructure to apply an electrical stimulatory signal to the at least one microstructure; using at least one sensor operatively connected to at least one microstructure, the at least one sensor being configured to measure electrical response signals from at least one microstructure; and, in one or more electronic processing devices: determining measured response signals, the response signals being at least partially indicative of a bioimpedance; and, performing an analysis at least in part using the measured response signals to determine at least one indicator at least partially indicative of fluid levels in the subject.

In one embodiment at least some of the microstructures are arranged in pairs, and wherein the system is configured so that at least one of: response signals are measured between microstructures in the pair; and, stimulation is applied between microstructures in the pair.

In one embodiment each pair of microstructures includes at least one of: spaced apart plate microstructures having substantially planar electrodes in opposition; and, spaced apart substantially parallel plate microstructures.

In one embodiment at least one of: at least some pairs of microstructures are angularly offset; at least some pairs of microstructures are orthogonally arranged; adjacent pairs of microstructures are orthogonally arranged; pairs of microstructures are arranged in rows, and the pairs of microstructures in one row are angularly offset relative to pairs of microstructures in other rows; pairs of microstructures are arranged in rows, and the pairs of microstructures in one row are orthogonally arranged relative to pairs of microstructures in other rows.

In one embodiment: a spacing between the microstructures in each pair is at least one of: less than 0.25 mm; about 0.1 mm; and, more than 10 μm; and, a spacing between groups of microstructures is at least one of: less than 1 mm; about 0.5 mm; and, more than 0.2 mm.

In one embodiment at least some of the microstructures are plates.

In one embodiment the plate microstructures are at least partially tapered and have a substantially rounded rectangular cross sectional shape.

In one embodiment at least some of the microstructures have at least one of: a length that is at least one of: less than 300 μm; about 150 μm; greater than 100 μm; and, greater than 50 μm; a maximum width that is at least one of: greater than the length; about the same as the length; less than 300 μm; about 150 μm; and, greater than 50 μm; and, a thickness that is at least one of: less than 50 μm; about 25 μm; greater than 10 μm.

In one embodiment at least some of the microstructures have a tip that at least one of: has a length that is at least one of: less than 50% of a length of the microstructure; at least 10% of a length of the microstructure; and, about 30% of a length of the microstructure; and, has a sharpness of at least one of: at least 0.1 μm; less than 5 μm; and, about 1 μm.

In one embodiment at least some of the microstructures include at least one of: a shoulder that is configured to abut against the stratum corneum to control a depth of penetration; and, a shaft extending from a shoulder to the tip, the shaft being configured to control a position of the tip in the subject.

In one embodiment the microstructures have a density that is at least one of: less than 5000 per $cm^2$; greater than 100 per $cm^2$; and, about 600 per $cm^2$.

In one embodiment the microstructures have a spacing that is at least one of: less than 1 mm; about 0.5 mm; about 0.2 mm; about 0.1 mm; and, more than 10 μm.

In one embodiment the substrate includes electrical connections to allow electrical signals to be applied to and/or received from respective microstructures.

In one embodiment the system includes one or more switches for selectively connecting at least one of the at least one sensor and at least one signal generator to one or more of the microstructures.

In one embodiment the one or more processing devices are configured to control the switches and the signal generator to allow at least one measurement to be performed.

In one embodiment system includes: a substrate coil positioned on the substrate and operatively coupled to one or more microstructure electrodes; and, an excitation and receiving coil positioned in proximity to the substrate coil such that alteration of a drive signal applied to the excitation and receiving coil acts as a response signal.

In one embodiment the electrode includes a coating on a surface of the microstructure.

In one embodiment the microstructure includes at least one of: a conductive core material; and a conductive core material and an electrically insulating layer including ports to allow electrical signals to be emitted from or received by the ports.

In one embodiment the microstructures include an insulating layer extending over at least one of: part of a surface of the microstructure; a proximal end of the microstructure; at least half of a length of the microstructure; about 90 μm of a proximal end of the microstructure; and, at least part of a tip portion of the microstructure.

In one embodiment at least one electrode has a surface area of at least one of: less than 200,000 $\mu m^2$; about 22,500 $\mu m^2$; at least 2,000$^{\mu m2}$.

In one embodiment at least one electrode at least one of: extends over a length of a distal portion of the microstructure; extends over a length of a portion of the microstructure spaced from the tip; is positioned proximate a distal end of the microstructure; is positioned proximate a tip of the microstructure; extends over at least 25% of a length of the microstructure; extends over less than 50% of a length of the microstructure; extends over about 60 μm of the microstructure; and, is configured to be positioned in a viable epidermis of the subject in use.

In one embodiment at least one of the substrate and the microstructures include at least one of: metal; polymer; and, silicon.

In one embodiment the microstructures include anchor microstructures used to anchor the substrate to the subject.

In one embodiment the anchor microstructures at least one of: include anchoring structures; have a length greater than that of other microstructures; and, enter the dermis.

In one embodiment the microstructures include a material including at least one of: a material to reduce biofouling; a material to attract at least one substance to the microstructures; and, a material to repel at least one substance from the microstructures.

In one embodiment at least some of the microstructures are coated with a coating.

In one embodiment the coating at least one of: modifies surface properties to at least one of: increase hydrophilicity; increase hydrophobicity; and, minimize biofouling; attracts at least one substance to the microstructures; repels at least one substance from the microstructures; acts as a barrier to preclude at least one substance from the microstructures; and, includes at least one of: polyethylene; polyethylene glycol; polyethylene oxide; zwitterions; peptides; hydrogels; and, self-assembled monolayer.

In one embodiment the system includes an actuator configured to apply a force to the substrate to cause the microstructures to penetrate the stratum corneum.

In one embodiment the actuator is at least one of: an electromagnetic actuator; an electric actuator; a piezoelectric actuator; and, a mechanical actuator.

In one embodiment the actuator is configured to apply at least one of: a vibratory force; and, a continuous force.

In one embodiment the vibratory force is applied at a frequency that is at least one of: at least 10 Hz; about 100 to 200 Hz; and, less than 1 kHz;

In one embodiment the force includes at least one of: a continuous force that is at least one of: greater than 1 N; less than 10 N; and, about 2.5 to 5 N; and, a vibratory force that is at least one of: at least 1 mN; about 200 mN; and, less than 1000 mN.

In one embodiment the actuator is configured to cause movement of the microstructures that is at least one of: at least 10 μm less than 300 μm; and, about 50 μm to 100 μm.

In one embodiment the one or more electronic processing devices control the actuator.

In one embodiment the system includes a housing containing the at least one sensor, the signal generator and at least one electronic processing device.

In one embodiment the housing selectively couples to the substrate.

In one embodiment the housing couples to the substrate using at least one of: electromagnetic coupling; mechanical coupling; adhesive coupling; and, magnetic coupling.

In one embodiment at least one of the housing and substrate are at least one of: secured to the subject; secured to the subject using anchor microstructures; secured to the subject using an adhesive patch; and, secured to the subject using a strap.

In one embodiment the housing includes housing connectors that operatively connect to substrate connectors on the substrate to communicate signals with the microstructures.

In one embodiment the system is configured to perform repeated measurements over a time period and wherein the microstructures are configured to remain in the subject during the time period.

In one embodiment the time period is at least one of: at least one minute; at least one hour; at least one day; and, at least one week.

In one embodiment the system is configured to perform repeated measurements with a frequency that is at least one of: substantially continuously; every second; every minute; every 5 to 10 minutes; and, hourly.

In one embodiment the system includes a transmitter that transmits at least one of: subject data derived from the measured response signals; and, measured response signals.

In one embodiment the system includes a monitoring device that is configured to: perform the measurements; and, at least one of: provide an output indicative of the indicator; and, provide a recommendation based on the indicator.

In one embodiment the system includes a monitoring device and a patch including the substrate and microstructures.

In one embodiment the monitoring device is at least one of: inductively coupled to the patch; attached to the patch; brought into contact with the patch when a reading is to be performed;

In one embodiment the monitoring device is configured to at least one of: cause a measurement to be performed; at least partially analyse measurements; control stimulation applied to at least one microstructure; generate an output; provide an output indicative of the indicator; provide a recommendation based on the indicator; and, cause an action to be performed.

In one embodiment the system includes: a wearable monitoring device that performs the measurements; and, a processing system that: receives subject data derived from the measured response signals; and, analyses the subject data to generate at least one indicator, the at least one indicator being at least partially indicative of a health status associated with the subject.

In one embodiment the system includes a client device that: receives measurement data from the wearable monitoring device; generates subject data using the measurement data; transfer the subject data to the processing system; receive an indicator from the processing system; and, displays a representation of the indicator.

In one embodiment the system is at least partially wearable.

In one embodiment the system is configured to perform impedance measurements in the viable epidermis to determine an indicator indicative of at least one of: interstitial fluid levels; a change in interstitial fluid levels; an ion concentration in interstitial fluid; a change in an ion concentration in interstitial fluid; an ion concentration; a change in an ion concentration; a total body water; intracellular fluid levels; extracellular fluid levels; plasma water levels; fluid volumes; and, hydration levels.

In one embodiment the indicator is indicative of a hydration of the subject. It will be appreciated that the broad forms of the invention and their respective features can be used in conjunction and/or independently, and reference to separate broad forms is not intended to be limiting. Furthermore, it will be appreciated that features of the method can be performed using the system or apparatus and that features of the system or apparatus can be implemented using the method.

BRIEF DESCRIPTION OF THE DRAWINGS

Various examples and embodiments of the present invention will now be described with reference to the accompanying drawings, in which:—

FIG. 5A is a schematic side view of an example of a plate microstructure;

FIG. 5B is a schematic front view of the microstructure of FIG. 5A;

FIG. 5C is a schematic underside view of an example of a patch including the microstructure of FIG. 5A;

FIG. 16A is an equivalent circuit for skin based impedance measurements;

FIG. 16B is an equivalent circuit for epidermal based impedance measurements;

FIG. 16C is a schematic diagram comparing skin and microstructure based impedance measurements;

FIGS. 17A to 17P are schematic diagrams illustrating steps in an example manufacturing process;

FIGS. 19A to 19L are schematic diagrams illustrating steps in an example manufacturing process;

FIG. 25A is a Scanning Electron Micrographs of microstructure prior to application into human forearm skin;

FIG. 25B is a Scanning Electron Micrographs of the microstructure of FIG. 25A post application into human forearm skin;

FIG. 25C is a Scanning Electron Micrographs of a microstructure patch post application into human forearm skin;

FIG. 25D is a Scanning Electron Micrographs of microstructure prior to application into human forearm skin;

FIG. 25E is a Scanning Electron Micrographs of the microstructure of FIG. 25D post application into human forearm skin; and, FIG. 25F is a Scanning Electron Micrographs of a microstructure patch post application into human forearm skin.

DETAILED DESCRIPTION OF THE PREFERRED EMBODIMENTS

Definitions

Figure 1:
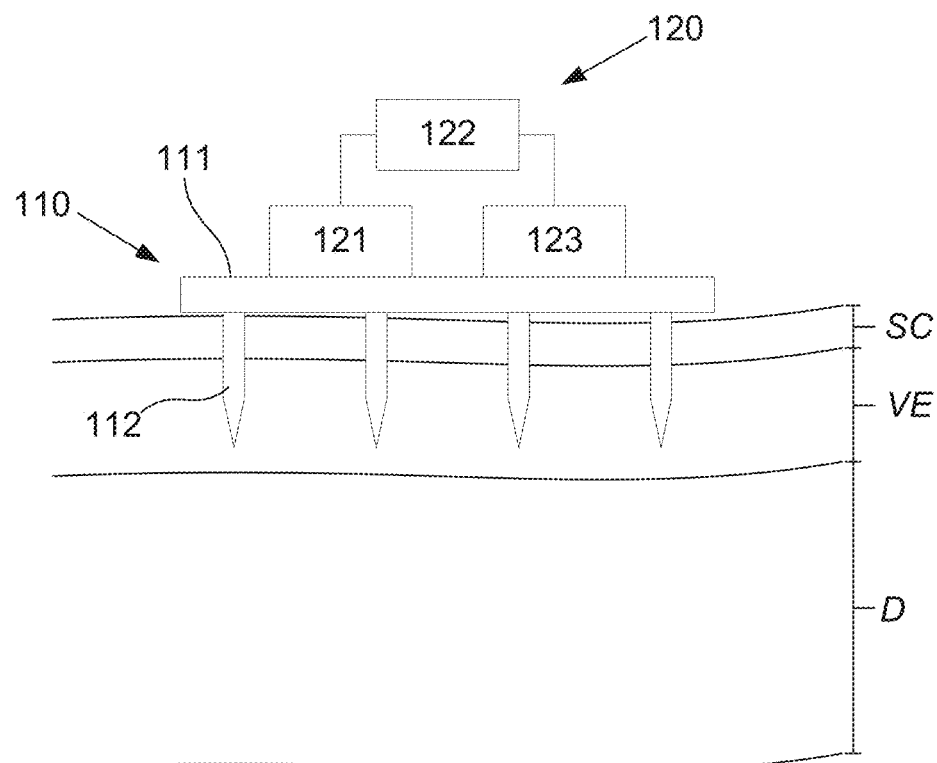
FIG. 1 is a schematic diagram of an example of a system for performing measurements on a biological subject.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The terms "about" and "approximately" are used herein to refer to conditions (e.g. amounts, levels, concentrations, time, etc.) that vary by as much as 20% (i.e. ±20%), especially by as much as 10%, 9%, 8%, 7%, 6%, 5%, 4%, 3%, 2% or 1% to a specified condition.

As used herein, the term "and/or" refers to and encompasses any and all possible combinations of one or more of the associated listed items, as well as the lack of combinations when interpreted in the alternative (or).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "plurality" is used herein to refer to more than one, such as 2 to $1 \times 10^{15}$ (or any integer therebetween) and upwards, including 2, 10, 100, 1000, 10000, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, etc. (and all integers therebetween).

The term "subject" as used herein refers to a vertebrate subject, particularly a mammalian subject, for whom monitoring and/or diagnosis of a disease, disorder or condition is desired. Suitable subjects include, but are not limited to, primates; avians (birds); livestock animals such as sheep, cows, horses, deer, donkeys and pigs; laboratory test animals such as rabbits, mice, rats, guinea pigs and hamsters; companion animals such as cats and dogs; and captive wild animals such as foxes, deer and dingoes. In particular, the subject is a human.

System for Performing Measurements

An example of a system for performing fluid level measurements on a biological subject will now be described with reference to FIG. 1.

In this example, the system includes at least one substrate 111 having a plurality of microstructures 112. In use, the microstructures are configured to breach a functional barrier associated with a subject. In the current example, the functional barrier is the stratum corneum SC, and the microstructures are configured to breach the stratum corneum SC by penetrating the stratum corneum SC and entering at least the viable epidermis VE. In one particular example, the microstructures are configured to not penetrate a boundary between the viable epidermis VE and the dermis D, although this is not essential and structures that penetrate into the dermis could be used as will be described in more detail below.

The nature of the microstructure will vary depending upon the preferred implementation, but typically structures, such as plates, blades, or the like, are used, as will be described in more detail below.

The substrate and microstructures could be manufactured from any suitable material, and the material used may depend on the intended application, for example depending on whether there is a requirement for the structures to be optically and/or electrically conductive, or the like. The substrate can form part of a patch 110, which can be applied to a subject, although other arrangements could be used for example, having the substrate form part of a housing containing other components.

At least some the microstructures including an electrode, which could be formed by the body of the microstructure, so that the microstructure is the electrode, or which could be a surface electrode provided on the microstructure. At least one sensor 121 is provided, which is operatively connected to at least one microstructure 112, thereby allowing response signals, and in particular electrical response signals, to be measured from respective microstructures 112. Additionally, at least one signal generator 123 is provided, which is operatively connected to at least one microstructure 112, thereby allowing stimulatory signals, and in particular, electrical stimulatory signals to be applied to respective microstructures 112.

It will be noted that whilst the term response signal will be understood to encompass signals that are intrinsic within the subject, such ECG (Electrocardiograph) signals, or the like, in the current example, the response signals are typically signals that are induced as a result of the application of electrical stimulation, such as bioimpedance signals, or the like.

The nature of the sensor will vary depending on the preferred implementation and the nature of the sensing being performed, but typically the sensor senses electrical signals, in which case the sensor could be a voltage or current sensor, or the like. Similarly the signal generator is typically a current source, or the like.

The manner in which the sensor 121 and signal generator 123 are connected to the microstructure(s) 112 will also vary depending on the preferred implementation. In one example, this is achieved using electrical connections between the microstructure(s) 112 and the sensor 121 and/or signal generator 123. Connections could also include wireless connections, allowing the sensor to be located remotely. Furthermore, connections could be provided as discrete elements, although in other examples, the substrate provides the connection, for example, if the substrate is made from a conductive plate which is then electrically connected to some or all of the microstructures. As a further alternative, the sensor could be embedded within or formed from part of the microstructure, in which connections may not be required.

The sensor 121 and/or signal generator 123 can be operatively connected to all of the microstructures 112, with connections being collective and/or independent. For example, one or more sensors and/or signal generators could be connected to different microstructures to allow different measured response signals to be measured from different groups of microstructures 112. However, this is not essential, and any suitable arrangement could be used.

These options allow a range of different types of sensing to be performed, including detecting electrical signals within the body, such as ECG signals, plethysmogram signals, electromagnetic signals, or electrical potentials generated by muscles, neural tissue, blood, or the like, detecting photoplethysmogram, electromagnetic effects, such as, fluorescence, detecting mechanical properties, such as stress or strain, or the like. Sensing typically includes detecting the body's response to applied electrical signals, for example to measure bioimpedance, bioconductance, or biocapacitance. However, it will be appreciated that other forms of sensing, such as detecting the presence, absence, level or concentration of analytes, for example by detecting electrical or optical properties, or the like, could also be performed.

The system further includes one or more electronic processing devices 122, which can form part of a measuring device, and/or could include electronic processing devices forming part of one or more processing systems, such as computer systems, servers, client devices, or the like as will be described in more detail below. In use, the processing devices 122 are adapted to receive signals from the sensor 121 and either store or process the signals. For ease of illustration the remaining description will refer generally to a processing device, but it will be appreciated that multiple processing devices could be used, with processing distributed between the devices as needed, and that reference to the singular encompasses the plural arrangement and vice versa.

Figure 2:
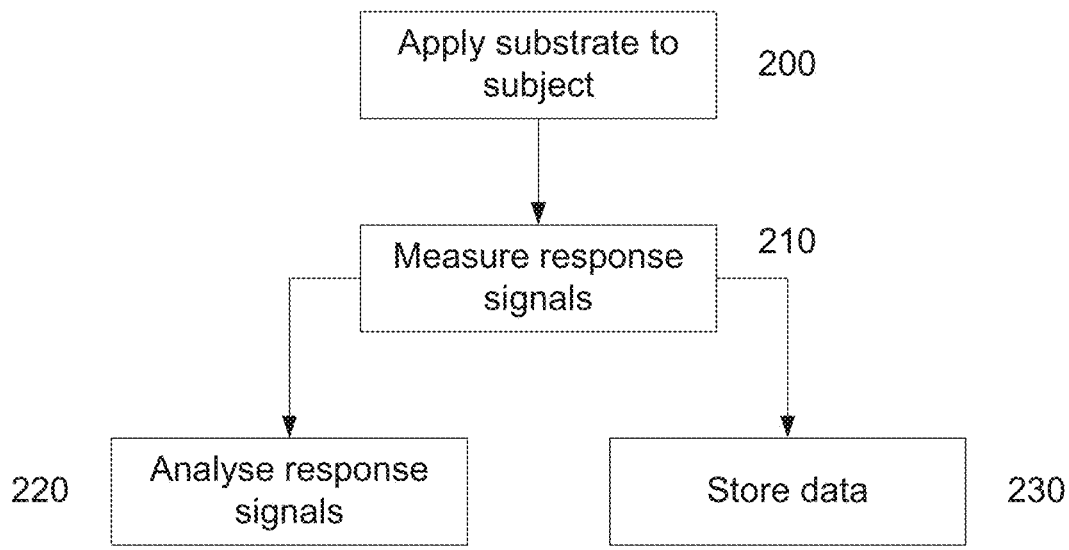
FIG. 2 is a flow chart of an example of a process for performing measurements on a biological subject.

An example of the manner in which this is performed will now be described with reference to FIG. 2.

In particular, in this example, at step 200, the substrate is applied to the subject so that the one or more microstructures breach, and in one example, penetrate the functional barrier. In this example, the substrate is applied to skin, so that the microstructures penetrate the stratum corneum and enter the viable epidermis as shown in FIG. 1. This could be achieved manually and/or through the use of an actuator, to help ensure successful penetration.

At step 210, response signals within the subject are measured in response to application of stimulation signals, with signals indicative of the measured response signals being provided to the electronic processing device 121.

The one or more processing devices then either analyse the resulting measurement data at step 220, and/or store the data based on the measurement data at step 230 for subsequent analysis, or could alternatively provide an output based on the measured response signals. For example, the processing device could display an indicator indicative of measured response signals and/or values derived therefrom. Alternatively, the processing device could generate a recommendation for an intervention, trigger an action, such as alerting a clinician, trainer or guardian, or the like.

The analysis can be performed in any suitable manner, and this will vary depending on nature of the measurements being performed. For example, when measuring fluid levels, this could involve examining the applied stimulatory signals and values of the measured response signals, using these to calculate a bioimpedance within the skin as a whole, or selectively within the skin strata such as the epidermis, which in turn allows an indicator indicative of fluid levels to be derived. In this regard, it will be understood that fluids within the body, such as interstitial fluid, contains ions, such as Sodium (Na+), Potassium (K+), Calcium ($Ca^2+$), Chloride (Cl−), Bicarbonate ($HCO_3-$) and Phosphate ($HPO_4^{2-}$). As fluid levels increase or decrease, for example as the subject's level of hydration increases or decreases, there will be a corresponding fall or rise in ion concentrations, thereby resulting in a change in conductivity of the fluid. Accordingly, measuring the impedance of the fluid can in turn be used to derive information regarding fluid conductivity, which is in turn indicative of ion concentrations and hence fluid levels. Thus, it will be appreciated that this allows changes in impedance to be used to track changes in fluid levels and hence a hydration state of the subject.

Such fluid levels could include any one or more of interstitial fluid levels, a change in interstitial fluid levels, an ion concentration in interstitial fluid, a change in an ion concentration in interstitial fluid, an ion concentration, a change in an ion concentration, a total body water, intracellular fluid levels, extracellular fluid levels, plasma water levels, fluid volumes or hydration levels.

The fluid level indicator could then be used in monitoring a health status, such as hydration levels, ion concentrations, and/or a presence, absence, degree or prognosis of one or more medical conditions, a prognosis associated with a medical condition, or the like. This could also involve monitoring changes in the values over time, for example to perform longitudinal hydration measurements, and may involve comparison to values measured for reference subjects having known hydration levels, thereby allowing an assessment to be made as to whether the subject is under or over hydrated.

In any event, it will be appreciated that the above described system operates by providing microstructures that are configured to breach the stratum corneum, allowing these to be used to apply stimulatory signals and measure response signals within the subject, and in particular, within the epidermis and/or dermis. These response signals can then be processed and subsequently analysed, allowing fluid levels to be derived, which could be indicative of specific measurements, or general hydration levels, or the like. In particular, in one preferred example, the system can be configured so that fluid level measurements are performed within the epidermis only, which in turn allows measures of body hydration to be performed with improved accuracy, providing higher quality data for more precise measures of body hydration. Furthermore, constraining the location in which measurements are performed ensures these are repeatable, allowing for more accurate longitudinal monitoring.

In contrast to traditional approaches, breaching and/or at least partially penetrating the stratum corneum allows measurements to be performed from within the epidermis and/or the dermis, which results in a significant improvement in the quality and magnitude of response signals that are detected. In particular, this ensures that the response signals accurately reflect conditions within the epidermis, such as the impedance of interstitial fluid, or the like, as opposed to traditional external measurements, which are unduly influenced by the environment outside the barrier, such as the physical properties of the skin surface, such as the skin material properties, presence or absence of hair, sweat, mechanical movement of the applied sensor, or the like. Additionally, by penetrating the stratum corneum but not the dermis, this allows measurements to be constrained to the epidermis only, thereby avoiding interference from fluid level changes in the dermis.

For example, this allows accurate measurement of fluid levels within the body which would otherwise be unduly influenced by skin factors. For example, in the case of impedance measurements microstructure electrodes tend to measure different parts of the equivalent circuit of human skin impedances as opposed to standard surface electrodes, which is indicative of the fact that the microstructure electrodes can selectively measure the impedance of the skin strata and do not measure whole skin or tissue impedance, meaning the measured impedance is more indicative of dynamic changes within the body. As the contribution of the skin surface and dermis impedance are significant in magnitude this can result in changes in impedance within the tissue being masked, meaning skin surface based measurements are less likely to be able to detect meaningful changes.

A further issue with skin based impedance measurements is that fields generated tend to pass through the stratum corneum and dermis, and are not constrained to the epidermis. An example of this is shown in FIG. 16C.

In this example, skin based electrodes 1601, result in an electric field 1602 extending into the stratum corneum SC, the viable epidermis VEPiD and dermis D. In contrast, a microstructure patch 1603 result in fields 1604 constrained within the viable epidermis VEPiD.

An example of resulting equivalent circuits for skin based measurements and epidermal measurements are shown in FIGS. 16A and 16B, respectively. In this regard, each equivalent circuit includes three circuits for each layer, representing a contribution of current flow through the tissue in orthogonal directions. Thus, for skin based measurements shown in FIG. 16A, the impedance of the stratum corneum is represented by the circuits $C_{SC1}$, $R_{SC1}$, $C_{SC2}$, $R_{SC2}$, $C_{SC3}$, $R_{SC3}$, the epidermis is represented by the circuits $C_{VE1}$, $R_{VE1}$, $C_{VE2}$, $R_{VE2}$, $C_{VE3}$, $R_{VE3}$, and the dermis is represented by the circuits $C_{D1}$, $R_{D1}$, $C_{D2}$, $R_{D2}$, $C_{D3}$, $R_{D3}$. In this example, $R_{SC1} \gg R_{VE1}$, $R_{SC2} \gg R_{VE2}$ and $R_{SC3} \gg R_{VE3}$, meaning that the contribution of the impedance in the epidermal layer is minimal compared to the contribution of the impedance in the stratum corneum, so skin based measurements will be more reflective of the impedance in the stratum corneum.

In contrast, for epidermal sensing only, shown in FIG. 16B, the impedance is represented by the circuits $C_{VE1}$, $R_{VE1}$, $C_{VE2}$, $R_{VE2}$, $C_{VE3}$, $R_{VE3}$, only, and hence epidermal measurements are more reflective of the fluid levels in the epidermis.

Additionally, in some examples, the microstructures only penetrate the barrier a sufficient distance to allow a measurement to be made. For example, in the case of skin, the microstructures are typically configured to enter the viable epidermis and not enter the dermal layer. This results in a number of improvements over other invasive techniques, including avoiding issues associated with penetration of the dermis, such as pain caused by exposure of nerves, erythema, petechiae, or the like. Avoiding penetrating the dermal boundary also significantly reduces the risk of infection, allowing the microstructures to remain embedded for prolonged periods of time, such as several days, which in turn can be used to perform longitudinal monitoring over a prolonged time periods.

It will be appreciated that the ability of the microstructures to remain in-situ is particularly beneficial, as this ensures that measurements are made at the same site within the subject, which reduces inherent variability arising from inaccuracies of replacement of measuring equipment which can arise using traditional techniques. Despite this, it will be appreciated that the system can be used in other manners, for example to perform single time point monitoring, or the like.

In one example, this allows the arrangement to be provided as part of a wearable device, enabling measurements to be performed that are significantly better than existing surface based measurement techniques, for example by providing access to dynamic signals within the skin that cannot otherwise be measured through the stratum corneum, but whilst allowing measurements to be performed whilst the subject is undergoing normal activities and/or over a prolonged period of time. This in turn enables measurements to be captured that are more accurately reflective of the health or other status of the subject. For example, this allows variations in a subject's condition during a course of the day to be measured, during physical activities, and avoids measurements being made under artificial conditions, such as within a clinic, which are not typically indicative of the actual condition of the subject. This also allows monitoring to be performed substantially continuously, which can allow conditions to be detected as they arise, for example, in the case of myocardial infarction, cardiovascular disease, vomiting, diarrhoea or similar, which can allow more rapid intervention to be sought.

Further variations will become apparent from the following description.

In one example, operation of the signal generator is controlled by the processing device, allowing the processing device to control the signal generator to thereby cause a measurement to be performed, for example by applying an electrical signal to allow an impedance measurement to be performed.

As mentioned above, the signal generator and/or sensor can be connected to the microstructures via connections. The nature of the connections will vary depending on the preferred implementation and the nature of the signal. In the case of electrical signals, the connections can be conductive connections, such as wires, or conductive tracks on a substrate, or could be formed by a conductive substrate. Connections could also include wireless connections, such as short-range radio frequency wireless connections, inductive connections, or the like. Connections could also be mechanical, magnetic, thermal, or the like.

In one example, inductive connections can be used to transmit signals and power, so that for example, inductive coupling could be used to power electronic circuits mounted on the substrate. This could be used to allow basic processing to be performed on board the substrate, such as amplifying and process impedance changes, using a simple integrated circuit or similar, without requiring an in-built power supply on the substrate.

In one example, the system can include response microstructures used to measure response signals and/or stimulation microstructures used to apply stimulation signals to the subject. Thus, stimulation and response could be measured via different microstructures, in which case the substrate typically incorporates response connections for allowing response signals to be measured and stimulation connections allowing stimulation signals to be applied. In some examples, multiple stimulation and response connections are provided, allowing different measurements to be performed via different connections. For example, different types of measurements could be performed via different microstructures or different parts of given microstructures, to enable multi-modal sensing. Additionally and/or alternatively, the same type of measurements could be performed at different locations and/or depths, for example to identify localised issues. In other cases, stimulation and measurement could be performed via the same connections, for example when making bipolar impedance measurements.

Signals could be applied to or measured from individual microstructures and/or to different parts of microstructures, which can be useful to discern features at different locations and/or depths within the body. This can be used for example to perform mapping or tomography, for example to produce images wherein the image contrast or colour is proportional to the concentrations of one or more analytes or the change in a physical property such as bioimpedance. Additionally, and/or alternatively, signals could be applied to or measured from multiple microstructures collectively, which can be used to improve signal quality, or perform measurements, such as bipolar, tetra-polar, or other multi-polar impedance measurements. Additionally and/or alternatively, microstructures might be used for both measuring and stimulation, for example applying a signal to a microstructure and then subsequently measuring a response therefrom.

In one particular example, sensors and/or signal generators can be connected to microstructures via one or more switching devices, such as multiplexers, allowing signals to be selectively communicated between the sensor or signal generator and different microstructures. The processing device is typically configured to control the switches, allowing a variety of different sensing and stimulation to be achieved under control of the processing device. In one example, this allows at least some electrodes can be used independently of at least some other electrodes. This ability to selectively interrogate different electrodes can provide benefits.

For example, this allows measurements to be performed via different electrodes to allow for spatial discrimination and hence mapping to be performed. For example, interrogating electrodes at different locations on a patch, this enables a map of measurements at different locations to be constructed, which can in turn be used to localise an effect, so as the presence of analytes or specific objects, such as lesions or cancer.

In one example, as described in more detail below, when electrodes are provided as pairs, this allows some pairs of electrodes to be used independently of other pairs. In one particular example, electrodes and/or pairs of electrodes, can be arranged in rows, and this can allows measurements to be performed on a row by row basis, although this is not essential and other groupings could be used.

The nature of the substrate and/or microstructures will vary depending upon the preferred implementation. For example, substrate and/or microstructures could be made from or contain fabric, woven fabric, electronic fabric, natural fibres, silk, organic materials, natural composite materials, artificial composite materials, ceramics, stainless steel, ceramics, metals, such as stainless steel, titanium or platinum, polymers, such as rigid or semi-rigid plastics, including doped polymers, silicon or other semiconductors, including doped semiconductors, organosilicates, gold, silver, carbon, carbon nano materials, or the like. The substrate and microstructures could be made from similar and/or dissimilar materials, and could be integrally formed, or made separately and bonded together. Microstructures can also be provided on one or more substrates, so for example, signals could be measured or applied between microstructures on separate substrates.

It will be appreciated that the particular material used will depend on the intended application, so for example different materials will be used if the microstructure needs to be conductive as opposed to insulative. Insulating materials, such as polymers and plastics could be doped so as to provide required conductivity, for example via doping with micro or nano sized metal particles, or conductive composite polymers could be used such as PEDOT:PSS (poly(3,4-ethylenedioxythiophene)polystyrene). If doping is used, this could involve using graphite or graphite derivates, including 2D materials such as graphene and carbon nanotubes, with these materials also being useable as stand-alone materials or as dopants in blends with polymers or plastics.

The substrate and microstructures can be manufactured using any suitable technique. For example, in the case of silicon-based structures, this could be performed using etching techniques. Polymer or plastic structures could be manufactured using additive manufacturing, such as 3D printing, moulding, imprinting, stamping, hot embossing, or the like. In one particular example, a mould is filled with a suitable filling material, such as a solution containing a material such as an active compound and/or sugar-based excipient, such as carboxy-methylcellulose (CMC), or one or more polymers, or the like, which is then cured and removed. It will also be appreciated that the filling material may include any required probes, reagents, or the like that are to be contained within the structures, as will be discussed in more detail below. Photosensitive or thermally sensitive polymers might be used, such as photoresists, including SU8 or polyimides, for direct patterning of electrodes on the substrate or to make microstructures. Successive layers of photosensitive resists, polymers, metals, or the like, can be deposited and/or selectively removed to produce bespoke 3D microstructure geometries.

In one example, the substrate could be at least partially flexible in order to allow the substrate to conform to the shape of a subject and thereby ensure penetration of the microstructures into the viable epidermis, or other functional barrier. In this example, the substrate could potentially be a textile or fabric, with electrodes and circuitry woven in, or multiple substrates could be mounted on a flexible backing, to provide a segmented substrate arrangement. Alternatively, the substrate could be shaped to conform to a shape of the subject, so that the substrate is rigid but nevertheless ensures penetration of the microstructures.

In preferred examples, the substrate and microstructures are formed from one or more of metal, polymer or silicon.

The microstructures could have a range of different shapes and could include ridges or needles, although plates or blades, or similar, are typically preferred. In this regard, the terms plates and blades are used interchangeably to refer to microstructures having a width that is of a similar order of magnitude in size to the length, but which are significantly thinner. The microstructures can be tapered to facilitate insertion into the subject, and can have different shapes, for example depending on the intended use. The microstructures typically have a rounded rectangular shape when viewed in cross section through a plane extending laterally through the microstructures and parallel to but offset from the substrate. The microstructures may include shape changes along a length of the microstructure. For example, microstructures could include a shoulder that is configured to abut against the stratum corneum to control a depth of penetration and/or a shaft extending to the tip, with the shaft being configured to control a position of the tip in the subject and/or provide a surface for an electrode.

Microstructures can have a rough or smooth surface, or may include surface features, such as pores, raised portions, serrations, or the like, which can increase surface area and/or assist in penetrating or engaging tissue, to thereby anchor the microstructures within the subject. This can also assist in reducing biofouling, for example by prohibiting the adherence and hence build-up of biofilms. The microstructures might also be hollow or porous and can include an internal structure, such as holes or similar, in which case the cross sectional shape could also be at least partially hollow. In particular embodiments, the microstructures are porous, which may increase the effective surface area of the microstructure. The pores may be of any suitable size to allow an analyte of interest to enter the pores, but exclude one or more other analytes or substances, and thus, will depend on the size of the analyte of interest. In some embodiments, the pores may be less than about 10 µm in diameter, preferably less than about 1 µm in diameter.

In one example, the microstructures have a rounded rectangular shape when viewed in cross section through a plane extending laterally through the microstructures and parallel to but offset from the substrate. The microstructures may include shape changes along a length of the microstructure. For example, microstructures could include a shoulder that is configured to abut against the stratum corneum to control a depth of penetration and/or a shaft extending to the tip, with the shaft being configured to control a position of the tip in the subject and/or provide a surface for an electrode.

Different microstructures could be provided on a common substrate, for example providing different shapes of microstructure to achieve different functions. In one example, this could include performing different types of measurement. In other examples, microstructures could be provided on different substrates, for example, allowing sensing to be performed via microstructures on one patch and delivery of therapy to be performed via microstructures on a different patch. In this example, this could allow a therapy patch to be replaced once exhausted, whilst a sensing patch could remain in situ. Additionally, measurements could be performed between patches, for example, performing whole of body impedance measurements between patches provided at different locations on a subject.

Additionally and/or alternatively anchor microstructures could be provided, which can be used to anchor the substrate to the subject. In this regard, anchor microstructures would typically have a greater length than that of the microstructures, which can help retain the substrate in position on the subject and ensure that the substrate does not move during the measurements or is not being inadvertently removed. Anchor microstructures can include anchoring structures, such as raised portions, which can assist with engaging the tissue, and these could be formed by a shape of the microstructure and/or a shape of a coating. Additionally, the coating could include a hydrogel or other similar material, which expands upon expose to moisture within the subject, thereby further facilitating engagement with the subject. Similarly the microstructure could undergo a shape change, such as swelling either in response to exposure to substances, such as water or moisture within the subject, or in response to an applied stimulation. When applied to skin, the anchor microstructures can enter the dermis, and hence are longer than other microstructures, to help retain the substrate in place, although it will be appreciated that this is not essential and will depend upon the preferred implementation. In other examples the anchor microstructures are rougher than other microstructures, have a higher surface friction than other microstructures, are blunter than other microstructures or are fatter than other microstructures.

In a further example, at least part of the substrate could be coated with an adhesive coating in order to allow the substrate and hence patch, to adhere to the subject.

As previously mentioned, when applied to skin, the microstructures typically enter the viable epidermis and preferably do not enter the dermis. But this is not essential, and for some applications, it may be necessary for the microstructures to enter the dermis, for example projecting shortly through the viable epidermis/dermis boundary or entering into the dermis a significant distance, largely depending on the nature of the sensing being performed. In one example, for skin, the microstructures have a length that is at least one of less than 2500 µm, less than 1000 µm, less than 750 µm, less than 600 µm, less than 500 µm, less than 400 µm, less than 300 µm, less than 250 µm, greater than 100 µm, greater than 50 µm and greater than 10 µm, but it will be appreciated that other lengths could be used. More generally, when applied to a functional barrier, the microstructures typically have a length greater than the thickness of the functional barrier, at least 10% greater than the thickness of the functional barrier, at least 20% greater than the thickness of the functional barrier, at least 50% greater than the thickness of the functional barrier, at least 75% greater than the thickness of the functional barrier and at least 100% greater than the thickness of the functional barrier.

In another example, the microstructures have a length that is no more than 2000% greater than the thickness of the functional barrier, no more than 1000% greater than the thickness of the functional barrier, no more than 500% greater than the thickness of the functional barrier, no more than 100% greater than the thickness of the functional barrier, no more than 75% greater than the thickness of the functional barrier or no more than 50% greater than the thickness of the functional barrier. This can avoid deep penetration of underlying layers within the body, which can in turn be undesirable, and it will be appreciated that the length of the microstructures used will vary depending on the intended use, and in particular the nature of the barrier to be breached, and/or signals to be applied or measured. The length of the microstructures can also be uneven, for example, allowing a blade to be taller at one end than another, which can facilitate penetration of the subject or functional barrier.

Similarly, the microstructures can have different widths depending on the preferred implementation. Typically, the widths are at least one of less than 25% of the length, less than 20% of the length, less than 15% of the length, less than 10% of the length, or less than 5% of the length. Thus, for example, when applied to the skin, the microstructures could have a width of less than 50 µm, less than 40 µm, less than 30 µm, less than 20 µm or less than 10 µm. However, alternatively, the microstructures could include blades, and could be wider than the length of the microstructures. In some example, the microstructures could have a width of less than 50000 µm, less than 40000 µm, less than 30000 µm, less than 20000 µm, less than 10000 µm, less than 5000 µm, less than 2500 µm, less than 1000 µm, less than 500 µm or less than 100 µm. In blade examples, it is also feasible to use microstructures having a width substantially up to the width of the substrate.

In general the thickness of the microstructures is significantly lower in order to facilitate penetration and is typically less than 1000 µm, less than 500 µm, less than 200 µm, less than 100 µm, less than 50 µm, less than 20 µm, less than 10 µm, at least 1 µm, at least 0.5 µm or at least 0.1 µm. In general the thickness of the microstructure is governed by mechanical requirements, and in particular the need to ensure the microstructure does not break, fracture or deform upon penetration. However, this issue can be mitigated through the use of a coating that adds additional mechanical strength to the microstructures.

In one specific example, for epidermal sensing, the microstructures have a length that is less than 300 µm, greater than 50 µm, greater than 100 µm and about 150 µm, and, a width that is greater than or about equal to a length of the microstructure, and is typically less than 300 µm, greater than 50 µm and about 150 µm. In another example, for dermal sensing, the microstructures have a length that is less than 450 µm, greater than 100 µm, and about 250 µm, and, a width that is greater than or about equal to a length of the microstructure, and at least of a similar order of magnitude to the length, and is typically less than 450 µm, greater than 100 µm, and about 250 µm. In other examples, longer microstructures could be used, so for example for hyperdermal sensing, the microstructures would be of a greater length. The microstructures typically have a thickness that is less than the width, significantly less than the width and of an order of magnitude smaller than the width. In one example, the thickness is less than 50 µm, greater than 10 µm, and about 25 µm, whilst the microstructure typically includes a flared base for additional strength, and hence includes a base thickness proximate the substrate that is about three times the thickness, and typically is less than 150 µm, greater than 30 µm and about 75 µm. The microstructures typically have a tip has a length that is less than 50% of a length of the microstructure, at least 10% of a length of the microstructure and more typically about 30% of a length of the microstructure. The tip further has a sharpness that is at least 0.1 µm, less than 5 µm and typically about 1 µm.

In one example, the microstructures have a relatively low density, such as less than 10000 per cm$^2$, such as less than 1000 per cm$^2$, less than 500 per cm$^2$, less than 100 per cm$^2$, less than 10 per cm$^2$ or even less than 5 per cm$^2$. The use of a relatively low density facilitates penetration of the microstructures through the stratum corneum and in particular avoids the issues associated with penetration of the skin by high density arrays, which in turn can lead to the need for high powered actuators in order for the arrays to be correctly applied. However, this is not essential, and higher density microstructure arrangements could be used, including less than 50,000 microstructures per cm$^2$, less than 30,000 microstructures per cm$^2$, or the like. As a result, the microstructures typically have a spacing that is less than 20 mm, less than 10 mm, less than 1 mm, less than 0.1 mm or less than 10 µm.

In one specific example, the microstructures have a density that is less than 5000 per cm$^2$, greater than 100 per cm$^2$, and about 600 per cm$^2$, leading to a spacing of less than 1 mm, more than 10 µm, and about 0.5 mm, 0.2 mm or 0.1 mm.

It should be noted that in some circumstances, microstructures are arranged in pairs, with the microstructures in each pair having a small spacing, such as less than 10 µm, whilst the pairs have a great spacing, such as more than 1 mm, in order to ensure a low overall density is maintained. However, it will be appreciated that this is not essential, and higher densities could be used in some circumstances.

As mentioned above, at least some of microstructures include an electrode, which can be used to apply electrical signals to a subject, measure intrinsic or extrinsic response electrical signals, for example measuring ECG or impedances. The microstructures could be made from a metal or other conductive material, so that the entire microstructure constitutes the electrode, or alternatively the electrode could be coated or deposited onto the microstructure, for example by depositing a layer of gold to form the electrode. The electrode material could include any one or more of gold, silver, colloidal silver, colloidal gold, colloidal carbon, carbon nano materials, platinum, titanium, stainless steel, or other metals, or any other biocompatible conductive material.

In a further example, the microstructure could include an electrically conductive core covered by a non-conductive layer (insulating), with openings providing access to the core to allow conduction of electrical signals through the openings, to thereby define electrodes. In one example, the insulating layer extends over part of a surface of the microstructure, including a proximal end of the microstructure adjacent the substrate. The insulating layer could extend over at least half of a length of the microstructure and/or about 90 µm of a proximal end of the microstructure, and optionally, at least part of a tip portion of the microstructure. In one specific example, this is performed so the non-insulating portion is provided in the epidermis, so stimulatory signals are applied to and/or response signals received from, the epidermis.

The insulating layer could also extend over some or all of a surface of the substrate. In this regard, in some examples connections are formed on a surface of the substrate, in which case a coating could be used to isolate these from the subject. For example, electrical tracks on a surface of the substrate could be used to provide electrical connections to the electrodes, with an insulating layer being provided on top of the connections to ensure the connections do not make electrical contact with the skin of the subject, which could in turn adversely affect measured response signals.

In one example, the microstructures include plates having a substantially planar face having an electrode thereon. The use of a plate shape maximizes the surface area of the electrode, whilst minimizing the cross sectional area of the microstructure, to thereby assist with penetration of the microstructure into the subject. This also allows the electrode to act as a capacitive plate, allowing capacitive sensing to be performed. In one example, the electrodes have a surface area of at least at least 10 mm$^2$, at least 1 mm$^2$, at least 100,000 µm$^2$, 10,000 µm$^2$, at least 7,500 µm$^2$, at least 5,000 µm$^2$, at least 2,000 µm$^2$, at least 1,000 µm$^2$, at least 500 µm$^2$, at least 100 µm$^2$, or at least 10 µm$^2$. In one example, the electrodes have a width or height that is up to 2500 µm, at least 500 µm, at least 200 µm, at least 100 µm, at least 75 µm, at least 50 µm, at least 20 µm, at least 10 µm or at least 1 µm. In the case of electrodes provided on blades, the electrode width could be less than 50000 µm, less than 40000 µm, less than 30000 µm, less than 20000 µm, less than 10000 µm, or less than 1000 µm, as well as including widths outlined previously. In this regard, it will be noted that these dimensions apply to individual electrodes, and in some examples each microstructure might include multiple electrodes.

In one specific example, the electrodes have a surface area of less than 200,000 µm$^2$, at least 2,000 µm$^2$ and about 22,500 µm$^2$, with the electrodes extending over a length of a distal portion of the microstructure, optionally spaced from the tip, and optionally positioned proximate a distal end of the microstructure, again proximate the tip of the microstructure. The electrode can extend over at least 25% and less than 50% of a length of the microstructure, so that the electrode typically extends over about 60 µm of the microstructure and hence is positioned in a viable epidermis of the subject in use. Other lengths, such as 90 µm or 150 µm could be used for dermal sensing.

In one example, at least some of the microstructures are arranged in groups, such as pairs, with response signals or stimulation being measured from or applied to the microstructures within the group. The microstructures within the group can have a specific configuration to allow particular measurements to be performed. For example, when arranged in pairs, a separation distance can be used to influence the nature of measurements performed. For example, when performing bioimpedance measurements, if the separation between the microstructures is greater than a few millimetres, this will tend to measure properties of interstitial fluid located between the electrodes, whereas if the distance between the microstructures is reduced, measurements will be more influenced by microstructure surface properties, such as the presence of materials bound to the surface of the microstructures. Measurements are also influenced by the nature of the applied stimulation, so that for example, current at low frequencies will tend to flow though extra-cellular fluids, whereas current at higher frequencies is more influenced by intra-cellular fluids.

In one particular example, plate microstructures are provided in pairs, with each pair including spaced apart plate microstructures having substantially planar electrodes in opposition. This can be used to generate a highly uniform field in the subject in a region between the electrodes, and/or to perform capacitive or conductivity sensing of substances between the electrodes. However, this is not essential, and other configurations, such as circumferentially spacing a plurality of electrodes around a central electrode, can be used. Typically the spacing between the electrodes in each group is typically less than 50 mm; less than 20 mm, less than 10 mm, less than 1 mm, less than 0.1 mm or less than 10 µm, although it will be appreciated that greater spacings could be used, including spacing up to dimensions of the substrate and/or greater, if microstructures are distributed across multiple substrates.

Thus, in one specific example, at least some of the microstructures are arranged in pairs, with response signals being measured between microstructures in the pair and/or stimulation being applied between microstructures in the pair. Each pair of microstructures typically includes spaced apart plate microstructures having substantially planar electrodes in opposition and/or spaced apart substantially parallel plate microstructures.

In one example, at least some pairs of microstructures are angularly offset, and in one particular example, are orthogonally arranged. Thus, in the case of plate microstructures, at least some pairs of microstructures extend in different and optionally orthogonal directions. This distributes stresses associated with insertion of the patch in different directions, and also acts to reduce sideways slippage of the patch by ensuring plates at least partially face a direction of any lateral force. Reducing slippage either during or post insertion helps reduce discomfort, erythema, or the like, and can assist in making the patch comfortable to wear for prolonged periods. Additionally, this can also help to account for any electrical anisotropy within the tissue, for example as a result of fibrin structures within the skin, cellular anisotropy, or the like.

In one specific example, adjacent pairs of microstructures are angularly offset, and/or orthogonally arranged, and additionally and/or alternatively, pairs of microstructures can be arranged in rows, with the pairs of microstructures in one row are orthogonally arranged or angularly offset relative to pairs of microstructures in other rows.

In one specific example, when pairs of microstructures are used, a spacing between the microstructures in each pair is typically less than 0.25 mm, more than 10 µm and about 0.1 mm, whilst a spacing between groups of microstructures is typically less than 1 mm, more than 0.2 mm and about 0.5 mm. Such an arrangement helps ensure electrical signals are primarily applied and measured within a pair and reduces cross talk between pairs, allowing independent measurements to be recorded for each pair of microstructures/electrodes.

Additionally, the microstructures can incorporate one or more materials or other additives, either within the body of the microstructure, or through addition of a coating containing the additive. The nature of the additive will vary depending on the preferred implementation and could include a material to reduce biofouling, a material to attract at least one substance to the microstructures, or a material to repel at least one substance from the microstructures. Example materials include polyethylene, polyethylene glycol, polyethylene oxide, zwitterions, peptides, hydrogels and SAMs.

The material can be contained within the microstructures themselves, for example by impregnating the microstructures during manufacture, or could be provided in a coating. For example, in the case of moulded patches manufactured using a polymer material, the material can be introduced into the mould together with the polymer material so that the material is distributed throughout the structures. In this example, the polymer can be arranged so that pores form within the structures during the curing process.

Using affinity surface coatings on each structure also allows a reduction of non-specific adsorption of ISF and/or blood components whilst facilitating specific extraction of the molecular targets of interest.

It will be appreciated that microstructures could be differentially coated, for example by coating different microstructures with different coatings, and/or by coating different parts of the microstructures with different coatings.

Additionally, at least some microstructures could remain uncoated, for example, to allow these to be used as a control, some may be partially coated, or may include a porous structure with an internal coating. It will also be appreciated that multiple coatings could be provided. For example, an outer coating could be provided that gives mechanical strength during insertion, and which dissolves once in-situ, allowing an underlying functional coating to be exposed, for example to allow analytes to be detected.

The nature of the coating and the manner in which this is applied will vary depending on the preferred implementation and techniques such as dip coating, spray coating, jet coating or the like, could be used, as described above. The thickness of the coating will also vary depending on the circumstances and the intend functionality provided by the coating. For example, if the coating is used to provide mechanical strength, or contains a payload material to be delivered to the subject, a thicker coating could be used, whereas if the coating is used for sensing other applications, a thinner coating might be required.

In one example, stimulation, such as chemical, biochemical, electrical, optical or mechanical stimulation, can be used to release material from the coating on the microstructure, disrupt the coating, dissolve the coating or otherwise release the coating.

In another example, the microstructures can be coated with a selectively dissolvable coating. The coating could be adapted to dissolve after a defined time period, such as after the microstructures have been present within the subject for a set length of time, in response to the presence, absence, level or concentration of one or more substances in the subject, upon breaching or penetration of the functional barrier, or in response application of a stimulatory signal, such as an electrical signal, optical signal or the like. Dissolving of the coating can be used in order to trigger a measurement process, for example by exposing a binding agent, or other functional feature, so that analytes are only detected once the coating has dissolved.

In a further example, dissolving of the coating could be detected, for example through a change in optical or electrical properties, with the measurement being performed after the coating has dissolved. Thus, dissolving of the coating could be detected based on a change in a response signal.

In one example, the coating can be used to provide mechanical properties. For example, the coating can provide a physical structure that can be used to facilitate penetration of the barrier, for example by providing a microstructure with a smooth tapered outer profile. The coating can strengthen the microstructures, to prevent microstructures breaking, fracturing, buckling or otherwise being damaged during insertion, or could be used to help anchor the microstructures in the subject. For example, the coating could include hydrogels, which expand upon exposure to moisture, so that the size of the microstructure and coating increases upon insertion into the subject, thereby making it harder to remove the microstructure.

The coating can also be used to modify surface properties of the microstructures, for example to increase or decrease hydrophilicity, increase or decrease hydrophobicity and/or minimize biofouling. The coating can also be used to attract or repel at least one substance, such as analytes, cells, fluids, or the like. The coating could also dissolve to expose a microstructure, a further coating or material, allowing this to be used to control the detection process. For example, a time release coating could be used to enable a measurement to be performed a set time after the patch has been applied. This could also be used to provide stimulation to the subject, for example by releasing a treatment or therapeutic material, or the like.

In one example, at least some of the microstructures attract at least one substance to the microstructures and/or repel or exclude at least one substance from the microstructures. The nature of the substance will vary depending on the preferred implementation and may include one or more analytes, or may include other substances containing analytes, such as ISF, blood or the like. This can be used to attract, repel or exclude analytes, for example attracting analytes of interest, allowing these to be concentrated and/or sensed, or repelling or excluding analytes that are not of interest.

The ability to repel or exclude substances can also assist with preventing biofouling. For example, the microstructures could contain a material, or include a coating, such as polyethylene glycol (PEG), which generally repels substances from the surface of the microstructure. Reduction in biofouling could also be achieved based on a choice of microstructure material or structure of the microstructure e.g. coating the binding agent in the pores of a porous microstructure, surface coatings that release to expose a sensing surface when sensing is to be performed, permeable coatings such as a porous polymer e.g. a nylon membrane, a polyvinylidenefluoride coating, a polyphenylenediamine coating, a polyethersulfone coating, or a hydrogel coating such as a poly(hydroxyethyl methacrylate) or PEG coating; an isoporous silica micelle membrane; a protein membrane, such as a fibroin membrane; a polysaccharide membrane, such as a cellulose membrane or a chitosan membrane; or a diol or silane membrane; releasable coatings that interfere with biofouling material; and/or porous coatings. In particular embodiments, the microstructure is porous, and the binding agent is coated in the pores of the microstructure.

In another example, biofouling can be accounted for using a control. For example, a patch could include functionalised microstructures for analyte detection as well as un-functionalised microstructures that act as a control. Assuming both sets of microstructures are subject to similar levels of biofouling, changes in response signals measured via the un-functionalised microstructures can be used to quantify a degree of biofouling that has occurred. This can then be accounted for when processing signals from the functionalised microstructures, for example by removing any change in response signals arising from the biofouling.

In one example, the system includes an actuator configured to apply force to the substrate, which in one example is used to help the microstructures to breach the barrier, and in particular the stratum corneum. The actuator could additionally and/or alternatively be used for other purposes. For example, the actuator can also be used to cause the microstructures to penetrate the barrier, or retract the microstructures from the barrier and/or the subject. In one example, this allows the microstructures to be inserted and removed from the subject as needed, so that microstructures can be removed when measurements are not being performed. This can be used to comfort, to reduce the chance of infection, reduce biofouling, or the like.

As the microstructures are provided in a low-density configuration, the force required is typically minimal, in which case this could be achieved utilising an actuator that provides a small force, such as piezoelectric actuator, or a mechanical actuator, such as an offset motor. Other actuators could however be used, including any one or more of an electric actuator, a magnetic actuator, a polymeric actuator, a fabric or woven actuator, a pneumatic actuator, a thermal actuator, a hydraulic actuator, a chemical actuator, or the like.

In one specific example, this is achieved using a biasing force, for example provided by a spring or electromagnetic actuator, together with a vibratory, periodic or repeated force, which can assist with penetration, for example by agitating the microstructures to overcome the elasticity of the stratum corneum and/or reduce friction for penetrating the epidermis and/or dermis, as well as to reduce the force required to pierce a barrier. This reduces the overall force required to penetrate the stratum corneum. However, this is not essential and single continuous or instantaneous forces could be used.

The frequency of vibration used will vary depending upon the preferred implementation and potentially the type of skin to which the microstructures are applied, and could include any one or more of at least 0.01 Hz, 0.1 Hz, 1 Hz, at least 10 Hz, at least 50 Hz, at least 100 Hz, at least 1 kHz, at least 1 kHz, or at least 100 kHz and potentially up to several MHz. In one example, a varying frequency could be used. The frequency could vary depending on a wide range of factors, such as a time of application, and in particular the length of time for which the application process has been performed, the depth or degree of penetration, a degree of resistance to insertion, or the like. In one example, the system uses response signals measured via the microstructures in order to detect when the barrier has been breached, such as when the microstructures have penetrated the stratum corneum. Thus, the frequency could be continuously varied, either increasing or decreasing, until successful penetration is achieved, or depending on a depth of penetration, which can be detected using response signals, at which point the actuator can be deactivated. In another example, the frequency starts high and progressively reduces as the microstructures penetrate the barrier, and in particular the stratum corneum.

In another example, the magnitude of the applied force can also be controlled. The force used will vary depending on a range of factors, such as the structure of the patch, the manner in which the patch is applied, the location of application, the depth of penetration, or the like. For example, patches with large numbers of microstructures typically require an overall higher force in order to ensure penetration, although for minimal numbers of microstructures, such as 10 or so, a larger force may be required to account for damping or loss from the substrate/skin. Similarly, the force required to penetrate the stratum corneum, would typically be higher than that required to penetrate the buccal mucosa. In one example, the applied force could be any one or more of at least 0.1 µN, at least 1 µN, at least 5 µN, at least 10 µN, at least 20 µN, at least 50 µN, at least 100 µN, at least 500 µN, at least 1000 µN, at least 10 mN, or at least 100 mN, per microstructure and/or collectively. For example, if there are 1000 microstructures, the force could be 100 mN in total, or 100 mN per projection, leading to an overall 100 N force.

Again, the force could vary, either increasing or decreasing, depending on a time of application, a depth or degree of penetration, which could be determined based on response signals, for examining a change in measured impedance, or an insertion resistance, or the like. In one specific example, the force is progressively increased until a point of penetration, at which point the force decreases.

As mentioned above, the force could be applied as a single continuous or instantaneous force. However, more typically the force is periodic. In this instance the nature of the periodic motion could vary, this could for example, have any waveform, including square waves, sine waves, triangular waves, variable waveforms, or the like. In this case, the force could be an absolute magnitude, or could be a peak-to-peak or Root Mean Square (RMS) force.

Similarly, a magnitude of movement of the microstructures can also be controlled. The degree of magnitude will depend on factors, such as the length of the microstructures and the degree of penetration required. The magnitude could include any one or more of greater than 0.001 times a length of the microstructure, greater than 0.01 times a length of the microstructure, greater than 0.1 times a length of the microstructure, greater than a length of the microstructure, greater than 10 times a length of the microstructure, greater than 100 times a length of the microstructure or greater than 1000 times a length of the microstructure. The magnitude may also vary, either increasing or decreasing, depending a time of application, a depth of penetration, a degree of penetration or an insertion resistance. Again, the magnitude may increase until a point of penetration and then decrease after a point of penetration.

In the above example, the system can be configured to detect aspects of the insertion process. In one example, this can be achieved by monitoring the actuator, for example, monitoring the current required by the actuator to achieve a specific movement, which can in turn be used to detect, a depth of penetration, a degree of penetration an insertion resistance, or the like, with this then being used to control the actuator.

The actuator can also be used to apply mechanical stimulation, which could be used for a variety of purposes. For example, the actuator can be configured to physically disrupt or dislodge a coating on the microstructures, physically stimulate the subject, cause the microstructures to penetrate the barrier, retract the microstructures from the barrier or retract the microstructures from the subject.

The actuator is typically operatively coupled to the substrate, which could be achieved using any suitable coupling mechanism, such as mechanical, electromechanical, or the like.

In one specific example, the actuator includes a spring or electromagnetic actuator to provide a constant bias, and a piezoelectric actuator or vibratory motor to apply a vibratory force. The vibratory force is applied at a frequency that is at least 10 Hz, less than 1 kHz and about 100-200 Hz. The continuous force is typically greater than 1 N, less than 10 N and about 5 N, whilst the vibratory force is at least 1 mN, less than 1000 mN and about 200 mN. The actuator is typically configured to cause movement of the microstructures that is at least 10 µm, less than 300 µm and about 50 µm to 100 µm.

In one example, the system includes a housing containing at least the sensor, the signal generator and one or more electronic processing devices, and optionally including other components, such as the actuator, power supply, wireless transceiver, or the like. In one particular example, the housing provides reader functionality that can be used to interrogate the microstructures, and which can be provided in an integrated device, or could be provided remote to the substrate and engaged or provided in proximity with the substrate when readings are to be performed.

In the integrated configuration, the reader is typically mechanically connected/integrated with the patch during normal use, allowing measurements to be performed automatically. For example, continual monitoring could be performed, with a reading being performed every 1 second to daily or weekly typically every 2 to 60 minutes, and more typically every 5 to 10 minutes. The timing of readings can vary depending on the nature of the measurement being performed and the particular circumstance. So for example, an athlete might wish to undergo more frequent monitoring while competing in an event, and then less frequent monitoring during post event recovery. Similarly, for a person undergoing medical monitoring, the frequency of monitoring may vary depending on the nature and/or severity of a condition. In one example, the frequency of monitoring can be selected based on user inputs and/or could be based on a defined user profile, or the like.

In the integrated arrangement, the reader can be connected to the patch using conventional resistance bridge circuitry, with analogue to digital conversion being used to perform measurements.

Alternatively, the reader can be separate, which allows the reader to be removed when not in use, allowing the user to wear a patch without any integrated electronics, making this less intrusive. This is particularly useful for applications, such as sports, geriatric and paediatric medicine, or the like, where the presence of a bulkier device could impact on activities. In this situation, the reader is typically brought into contact or proximity with the patch allowing readings to be performed on demand. It will be appreciated that this requires a user/person to drive the interrogation. However, the reader could include alert functionality to encourage interrogation.

Readings could be performed wirelessly, optionally using inductive coupling to both power the patch and perform the reading as will be described in more detail below, although alternatively, direct physical contact could alternatively be used. In this example, the microstructures and tissue form part of a resonant circuit with discrete inductance or capacitance, allowing the frequency to be used to determine the impedance and hence fluid levels. Additionally, and/or alternatively, ohmic contacts could be used, where the reader makes electrical contact with connectors on the patch.

In either case, some analysis and interpretation of the hydration signal may be performed in the reader, optionally allowing an indicator to be displayed on the reader using an output, such as an LED indicator, LCD screen, or the like. Additionally, and/or alternatively, audible alarms may be provided, for example providing an indication in the event that the subject is under or over hydrated. The reader can also incorporate wireless connectivity, such as Bluetooth, Wi-Fi or similar, allowing reading events to be triggered remotely and/or to allow data, such as impedance values, hydration indicators, or the like to be transmitted to remote devices, such as a client device, computer system, or cloud based computing arrangement.

In one example, the housing selectively couples to the substrate, allowing the housing and substrate to be attached and detached as needed. In one example, this could be achieved utilising any appropriate mechanism, such as electromagnetic coupling, mechanical coupling, adhesive coupling, magnetic coupling, or the like. This allows the housing and in particular sensing equipment to only be connected to the substrate as needed. Thus, a substrate could be applied to and secured to a subject, with a sensing system only being attached to the substrate as measurements are to be performed. However, it will be appreciated that this is not essential, and alternatively the housing and substrate could be collectively secured to the subject for example using an adhesive patch, adhesive coating on the patch/substrate, strap, anchor microstructures, or the like. In a further example, the substrate could form part of the housing, so that the substrate and microstructures are integrated into the housing.

When the housing is configured to attach to the substrate, the housing typically includes connectors that operatively connect to substrate connectors on the substrate, to thereby communicate signals between the signal generator and/or sensor, and the microstructures. The nature of the connectors and connections will vary depending upon the preferred implementation and the nature of the signal, and could include conductive contact surfaces, that engage corresponding surfaces on the substrate, or could include wireless connections, such as tuned inductive coils, wireless communication antennas, or the like.

In one example, the system is configured to perform repeated measurements over a time period, such as a few hours, days, weeks, or similar. To achieve this, the microstructures can be configured to remain in the subject during the time period, or alternatively could be removed when measurements are not being performed. In one example, the actuator can be configured to trigger insertion of the microstructures into the skin and also allow for removal of the microstructures once the measurements have been performed. The microstructures can then be inserted and retracted as needed, to enable measurements to be performed over a prolonged period of time, without ongoing penetration of the skin. However, this is not essential and alternatively short term measurements can be performed, in which case the time period can be less than 0.01 seconds, less than 0.1 seconds, less than 1 second or less than 10 seconds. It will be appreciated that other intermediate time frames could also be used.

In one example, once measurements have been performed, the one or more electronic processing devices analyse the measured response signals to determine an indicator indicative of a health and/or physiological status of the subject.

In one example, this is achieved by deriving at least one metric, which can then be used to determine an indicator. For example, the system could be configured to perform impedance measurements, with the metric corresponding to an impedance parameter, such as an impedance at a particular frequency, a phase angle, or similar. The metric can then be used to derive indicators, such as an indication of fluid levels, such as extra or intra cellular fluid levels.

The manner in which this is performed will vary depending upon the preferred implementation. For example, the electronic processing devices could apply the metric to at least one computational model to determine the indicator, with the computational model embodying the relationship between a health status and the one or more metrics. In this instance, the computational model could be obtained by applying machine learning to reference metrics derived from subject data measured for one or more reference subjects having known health statuses. In this instance, the health status could be indicative of organ function, tissue function or cell function, could include the presence, absence, degree or severity of a medical condition, or could include one or more measures otherwise associated with a health status, such as measurements of the presence, absence, level or concentration of one or more analytes or measurements of other biomarkers.

The nature of the model and the training performed can be of any appropriate form and could include any one or more of decision tree learning, random forest, logistic regression, association rule learning, artificial neural networks, deep learning, inductive logic programming, support vector machines, clustering, Bayesian networks, reinforcement learning, representation learning, similarity and metric learning, genetic algorithms, rule-based machine learning, learning classifier systems, or the like. As such schemes are known, these will not be described in any further detail. In one example, this can include training a single model to determine the indicator using metrics from reference subjects with a combination of different health states, or the like, although this is not essential and other approaches could be used.

Measured signals can also be used in other manners. For example, changes in metrics over time can be used to track changes in a health state or medical condition for a subject. Measured signals can also be analysed in order to generate images or to perform mapping. For example, tomography could be used to establish a 2D or 3D image of a region of the subject based on impedance measurements or similar. The signals could also be used in contrast imaging, or the like.

In one example, the system can include a transmitter that transmits measured subject data, metrics or measurement data such as response signals or values derived from measured response signals, allowing these to be analysed remotely.

In one particular example, the system includes a wearable patch including the substrate and microstructures, and a monitoring device (also referred to as a "reader") that performs the measurements. The monitoring device could be attached or integrally formed with the patch, for example mounting any required electronics on a rear side of the substrate. Alternatively, the reader could be brought into contact with the patch when a reading is to be performed. In either case, connections between the monitoring device could be conductive contacts, but alternatively could be indicative coupling, allowing the patch to be wirelessly interrogated and/or powered by the reader.

The monitoring device can be configured to cause a measurement to be performed and/or to at least partially analyse measurements. The monitoring device can control stimulation applied to at least one microstructure, for example by controlling the signal generator and/or switches as needed. This allows the monitoring device to selectively interrogate different microstructures, allowing different measurements to be performed, and/or allowing measurements to be performed at different locations.

The monitoring device could also be used to generate an output, such as an output indicative of the indicator or a recommendation based on the indicator and/or cause an action to be performed. Thus, the monitoring device could be configured to generate an output including a notification or an alert. This can be used to trigger an intervention, for example, indicating to a user that action is required. This could simply be an indication of an issue, such as telling a user they are dehydrated or have elevated troponin levels and/or could include a recommendation, such as telling the user to rehydrate, or seek medical attention or similar. The output could additionally and/or alternatively, include an indication of an indicator, such as a measured value, or information derived from an indicator. Thus, a hydration level or analyte level or concentration could be presented to the user.

The monitoring device could also be configured to trigger other actions,

The output could be used to alert a caregiver that an intervention is required, for example transferring a notification to a client device and/or computer of the caregiver. In another example, this could also be used to control remote equipment. For example, this could be used to trigger a drug delivery system, such as an electronically controlled syringe injection pump, allowing an intervention to be triggered automatically. In a further example, a semi-automated system could be used, for example providing a clinician with a notification including an indicator, and a recommended intervention, allowing the clinician to approve the intervention, which is then performed automatically.

In one example, the monitoring device is configured to interface with a separate processing system, such as a client device and/or computer system. In this example, this allows processing and analysis tasks to be distributed between the monitoring device and the client device and/or computer system. For example, the monitoring device could perform partial processing of measured response signals, such as filtering and/or digitising these, providing an indication of the processed signals to a remote process system for analysis. In one example, this is achieved by generating subject data including the processed response signals, and transferring this to a client device and/or computer system for analysis. Thus, this allows the monitoring device to communicate with a computer system that generates, analyses or stores subject data derived from the measurement data. This can then be used to generate an indicator at least partially indicative of a health status associated with the subject.

It will also be appreciated that this allows additional functionality to be implemented, including transferring notifications to clinicians, or other caregivers, and also allowing for remote storage of data and/or indicators. In one example, this allows recorded measurements and other information, such as derived indicators, details of applied stimulation or therapy and/or details of other resulting actions, to be directly incorporated into an electronic record, such as an electronic medical record.

In one example, this allows the system to provide the data that will underpin the growing telehealth sector empowering telehealth systems with high fidelity and accurate clinical data to enable remote clinicians to gain the information they require, and they will be highly valued both in central hospitals and in rural areas away from centralized laboratories and regional hospitals. With time to treatment a strong predictor of improved clinical outcomes with heart attack patients, decentralized populations cannot rely solely on access to conventional large-scale hospitals. Accordingly, the system can provide a low cost, robust and accurate monitoring system, capable for example of diagnosing a heart attack, and yet being provided at any local health facility and as simple as applying a patch device. In this example, resources could be dispatched quickly for patients who test positive to troponin I, with no delay for cardiac troponin laboratory blood-tests. Similarly patients determined to be low-risk could be released earlier and with fewer invasive tests, or funnelled into other streams via their GP etc.

In a further example, a client device such as a smart phone, tablet, or the like, is used to receive measurement data from the wearable monitoring device, generate subject data and then transfer this to the processing system, with the processing system returning an indicator, which can then be displayed on the client device and/or monitoring device, depending on the preferred implementation.

However, this is not essential and it will be appreciated that some or all of the steps of analysing measurements, generating an indicator and/or displaying a representation of the indicator could be performed on board the monitoring device.

Again, it will be appreciated that similar outputs could also be provided to or by a remote processing system or client device, for example, alerting a clinician or trainer that a subject or athlete requires attention.

The reader could be configured to perform measurements automatically when integrated into or permanently/semi permanently attached to the patch, or could perform measurements when brought into contact with the patch if the reader is separate. In this latter example, the reader can be inductively coupled to the patch.

Thus, it will be appreciated that functionality, such as processing measured response signals, analysing results, generating outputs, controlling measurement procedures and/or therapy delivery could be performed by an on-board monitoring device, and/or could be performed by remote computer systems, and that the particular distribution of tasks and resulting functionality can vary depending on the preferred implementation.

In one example, the system includes a substrate coil positioned on the substrate and operatively coupled to one or more microstructure electrodes, which could include microstructures that are electrodes, or microstructures including electrodes thereon. An excitation and receiving coil is provided, typically in a housing of a measuring device, with the excitation and receiving coil being positioned in proximity to the substrate coil in use. This is performed to inductively couple the excitation and receiving coil to the substrate coils, so that when an excitation signal is applied to the drive coil, this induces a signal in the substrate coil, which, in association with the electrodes and other reactive components on the substrate, may form a resonant circuit. As a result, the signal frequency, amplitude and damping (Q) of the resonant circuit on the substrate will be reflected in signal observed in the excitation and receive coil, which in turn alters the drive signal applied to the excitation and receiving coil, for example by changing the frequency, phase or magnitude of the signal, allowing this to act as a response signal, for example allowing a bioimpedance to be measured.

A further example of a system for performing measurements in the biological subject will now be described with reference to FIGS. 3A to 3K.

In this example, the system includes a monitoring device 320, including a sensor 321 and one or more electronic processing devices 322. The system further includes a signal generator 323, a memory 324, an external interface 325, such as a wireless transceiver, an actuator 326, and an input/output device 327, such as a touchscreen or display and input buttons, connected to the electronic processing device 322. The components are typically provided in a housing 330, which will be described below.

The nature of the signal generator 323 and sensor 321 will depend on the measurements being performed, and could include a current source and voltage sensor, laser or other electromagnetic radiation source, such as an LED and photodiode or CCD sensor, or the like. The actuator 326 is typically a spring or electromagnetic actuator in combination with a piezoelectric actuator or vibratory motor coupled to the housing, to bias and vibrate the substrate relative to an underside of the housing, to thereby urge the microstructures into the skin, whilst the transceiver is typically a short-range wireless transceiver, such as a Bluetooth system on a chip (SoC).

The processing device 322 executes software instructions stored in the memory 324 to allow various processes to be performed, including controlling the signal generator 323, receiving and interpreting signals from the sensor 321, generating measurement data and transmitting this to a client device or other processing system via the transceiver 325. Accordingly, the electronic processing device is typically a microprocessor, microcontroller, microchip processor, logic gate configuration, firmware optionally associated with implementing logic such as an FPGA (Field Programmable Gate Array), or any other electronic device, system or arrangement.

In use the monitoring device 320 is coupled to a patch 310, including a substrate 311 and microstructures 312, which are coupled to the sensor 321 and/or signal generator 323 via connections 313. The connections could include physical conductive connections, such as conductive tracks, although this is not essential and alternatively wireless connections could be provided, such inductive coupling or radio frequency wireless connections. In this example, the patch further includes anchor microstructures 314 that are configured to penetrate into the dermis and thereby assist in securing the patch to the subject.

Figure 3A:
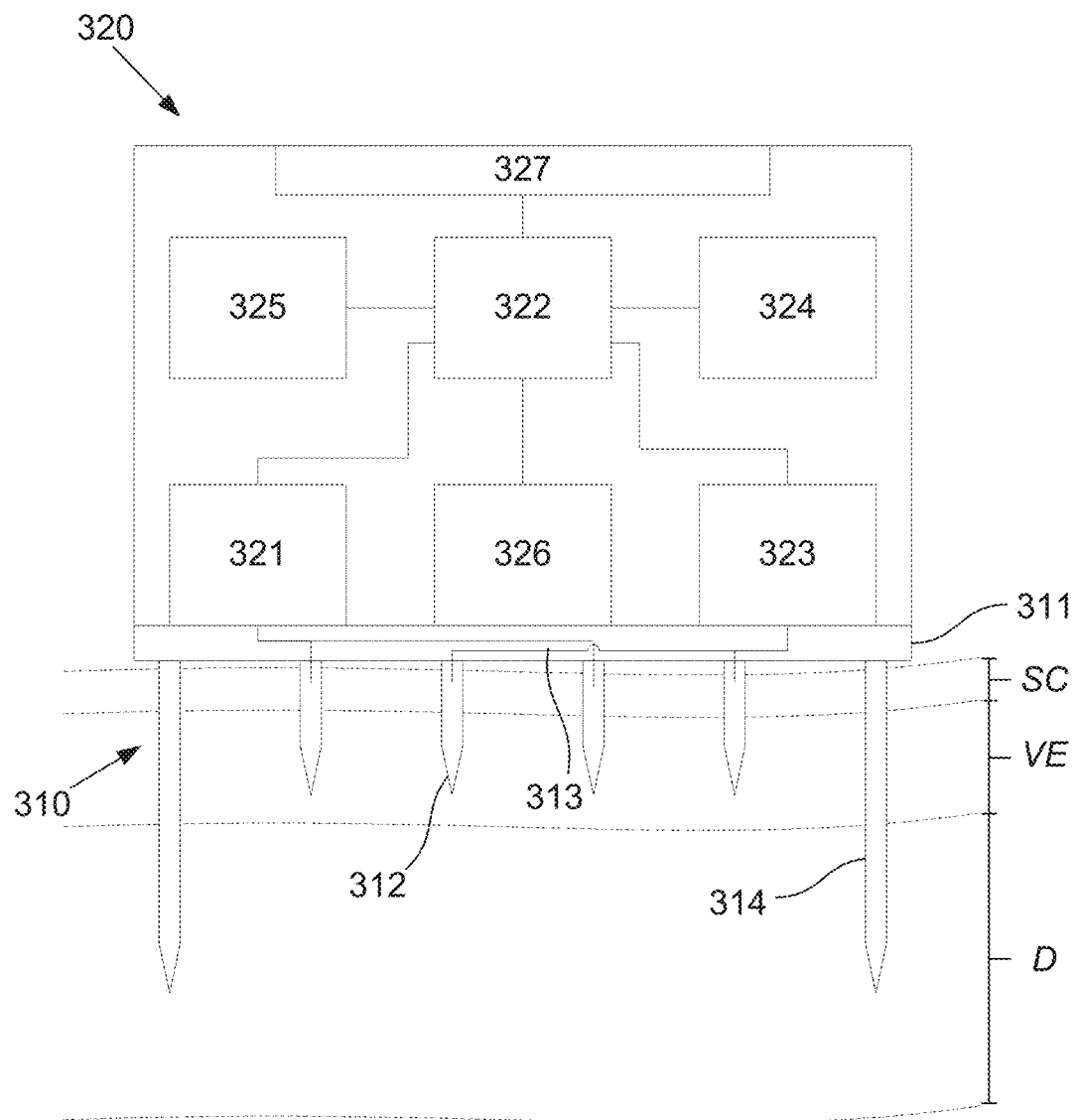
FIG. 3A is a schematic side view of a further example of a system for performing measurements on a biological subject.
Figure 3B:
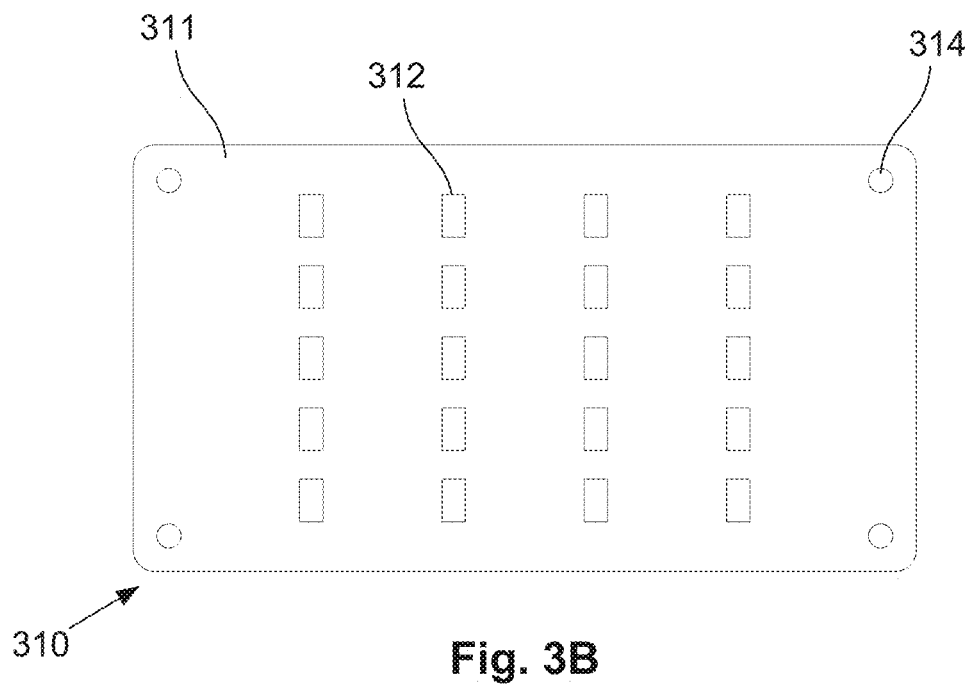
FIG. 3B is a schematic underside view of an example of a patch for the system of FIG. 3A.
Figure 3C:
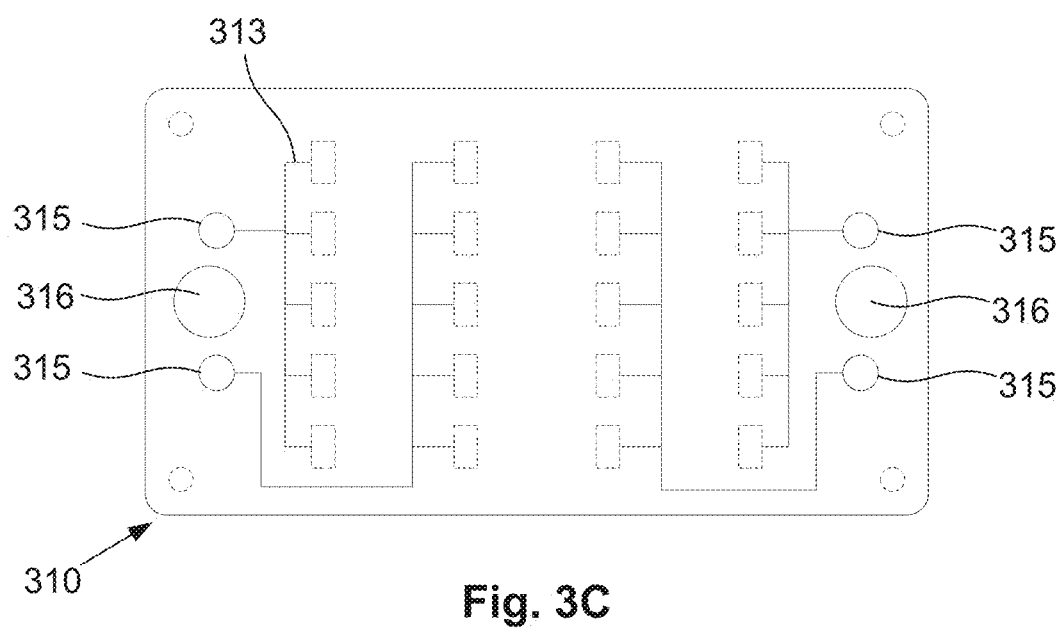
FIG. 3C is a schematic plan view of the patch of FIG. 3B.

An example of the patch 310 is shown in more detail in FIGS. 3B and 3C. In particular, in this example the substrate 311 is generally rectangular, with round corners to avoid discomfort when the substrate is applied to the subject's skin. The substrate 311 includes anchor microstructures 314 are provided proximate corners of the substrate 311 to help secure the substrate, whilst measurement microstructures 312 are arranged in an array on the substrate. In this example, the array has a regular grid formation, with the microstructures 312 being in provided in equally spaced rows and columns, but this is not essential and alternative spacing configurations could be used, as will be described in more detail below.

In the example of FIGS. 3B and 3C, four connectors 315 are provided which are connected to respective microstructures 312 via connections 313 to allow stimulation signals and response signals to be applied to and measured from two sets of respective microstructures. This can be used to allow for symmetric or differential application and detection of signals, as opposed to asymmetric or single-ended application or detection, which is typically performed relative to a ground reference, and which is in turn generally noisier. However, it will be appreciated that for some detection modalities, such as optical detection, or the like, this is not relevant and single connections 315 may be provided.

Figure 3D:
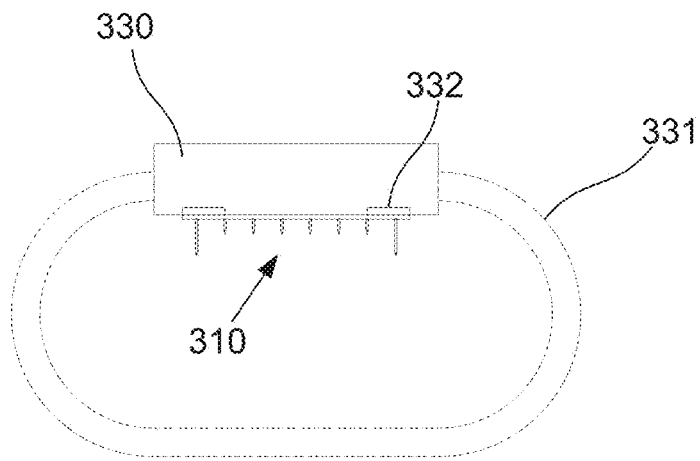
FIG. 3D is a schematic side view of an example of a housing arrangement for the system of FIG. 3A.
Figure 3E:
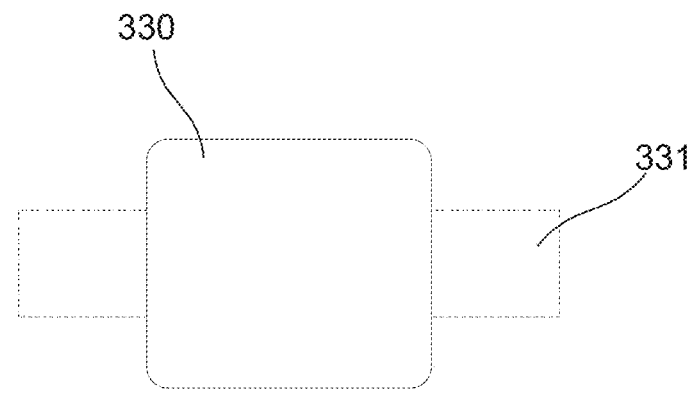
FIG. 3E is a schematic plan view of the housing arrangement of FIG. 3D.

In the example of FIGS. 3D and 3E, the housing 330 is a generally rectangular housing. The measuring device can optionally have a form factor similar to a watch, or other wearable device, in which case a strap 331 is included that allows the housing to be secured to the user. However, this is not essential and other securing mechanisms could be used. Alternatively, the housing could simply be brought into engagement with the patch and held in position each time a measurement is performed. In this example, the housing includes coupling members 332, such as magnets, or the like, which can engage with corresponding coupling members 316 on the substrate allowing the substrate to be secured to the housing. Whilst any form of coupling member could be used, the use of magnets is particularly advantageous as these can be contained within the housing 330, allowing the housing to be sealed, and can also act to ensure correct alignment of the substrate 310, for example by having polarities of the magnets guide a relative orientation of the substrate 310 and housing 330.

However, it will be appreciated that this configuration is for the purpose of illustration only, and other arrangements could be used. For example, the substrate could form part of an adhesive patch, which is applied to the subject and retained in place. Alternatively, adhesive could be provided on a surface of the substrate to adhere the substrate directly to the subject. The housing 330, could then be selectively attached to the patch, for example, using magnetic coupling, thereby allowing measurements to be performed as needed.

In this example, the substrate could be a flexible substrate, which can be achieved using a woven or non-woven fabric or other suitable material, with microstructures directly attached thereto. More typically however, flexibility is achieved using a number of individual substrates 311 mounted on a flexible backing 319, to form a segmented substrate, as shown in FIG. 3H. It will be appreciated that such arrangements can be used in a wide variety of circumstances, including having the substrates mounted to a strap or the like, for attachment to the subject.

Figure 3F:
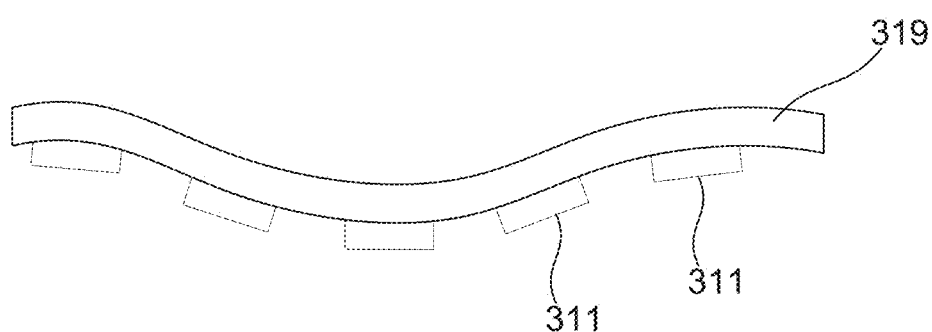
FIG. 3F is a schematic side view of an example of a flexible segmented substrate arrangement.
Figure 3G:
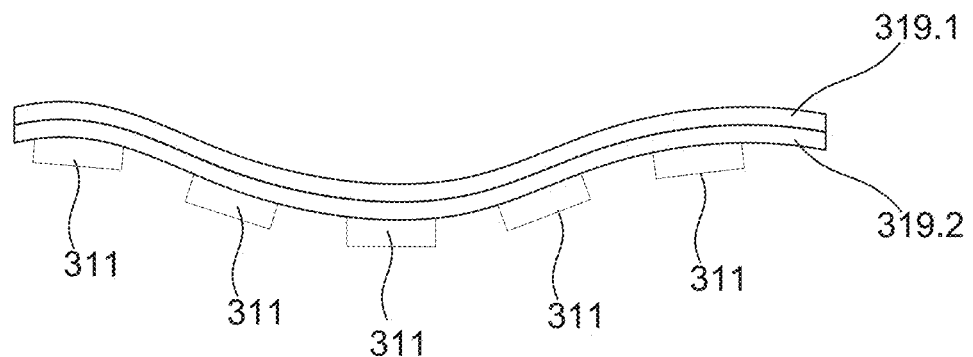
FIG. 3G is a schematic side view of a further example of a flexible segmented substrate arrangement.
Figure 3H:
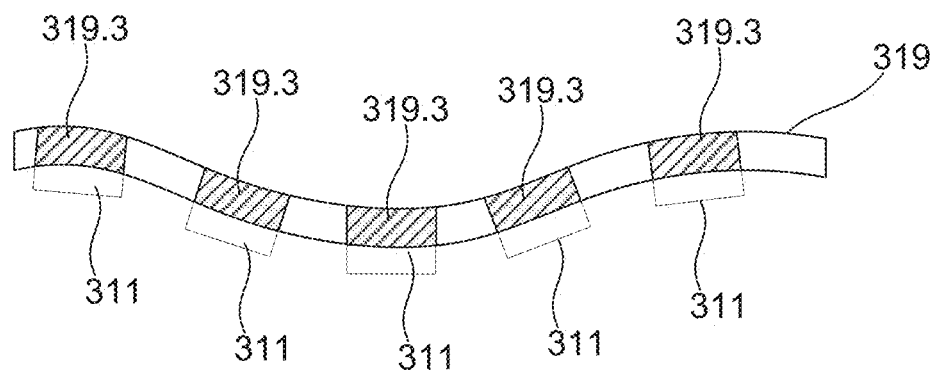
FIG. 3H is a schematic side view of a further example of a flexible segmented substrate arrangement.

A number of further variations are shown in FIGS. 3F to 3H.

Specifically in the example of FIG. 3F, the backing 319 is formed from multiple backing layers 319.1, 319.2, with two being shown in the example for the purpose of illustration only. The use of multiple layers can be beneficial in achieving desired properties, for example to provide adhesive, or waterproof layers, or the like.

In the example of FIG. 3G, the backing layer has multiple interspersed regions 319.3, which can be used for particular purposes, such as to allow for easier attachment of the substrates 311, to provide connectivity to a measuring device 320, to allow for increased flexibility between the substrates 311, or the like. In this example, interspersed regions are substantially aligned with the substrates, although it will be appreciated that this is not essential, and they could be provided at other locations.

A further example shown in FIG. 3H, includes a number of shape modifications, including thinner regions 319.4, located between substrates, which could be used to enhance flexibility, thicker regions 319.5 between the substrates, which could increase strength. Similarly thinner or thicker regions 319.5, 319.6 could be provided in line with the substrates, for example to enhance strength, flexibility, connection to a measuring device, or the like.

Whilst these features have been described with reference to a backing layer, it will be appreciated that similar approaches could be used for the substrate itself.

Figure 3I:
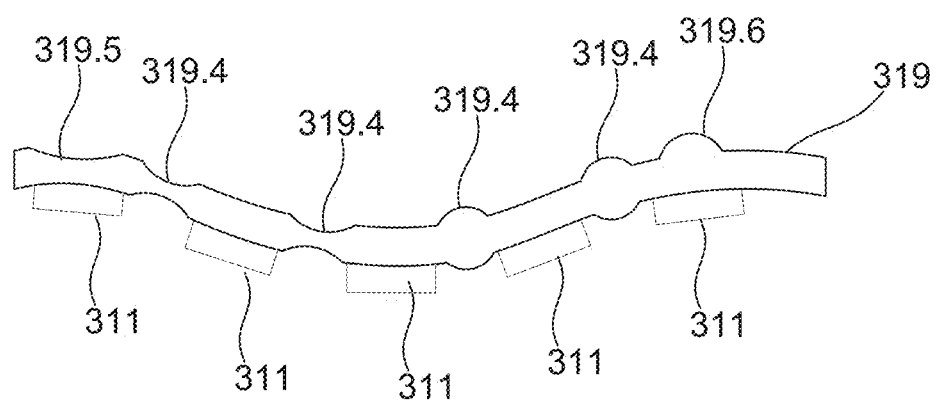
FIG. 3I is a schematic side view of a further example of a flexible segmented substrate arrangement.

An example of an actuator configuration to assist with applying a patch will now be described with reference to FIG. 3I.

In this example, the housing 330 includes a mounting 333 to which the actuator 326, such as a piezoelectric actuator, or vibrating motor, is attached. The actuator 326 is aligned with an opening 334 in an underside of the housing 330, with an arm 326.1 coupled to the actuator 326 extending through the opening 334, which may be sealed using an O-ring 334.1, or other similar arrangement.

The patch substrate 311 is positioned adjacent the underside of the housing 330, with magnets 316, 332 being arranged to urge the substrate 311 towards the housing 330. The arm 326.1 engages the substrate to thereby transmit forces from the actuator 326 to the substrate 311, allowing the substrate and hence microstructures 312, 314, to be vibrated to aid insertion of the microstructures into the subject. Specifically, this arrangement transmits forces directly to the substrate 311, allowing forces in the substrate to be maximised, whilst minimising vibration of the housing 330.

Figure 3J:
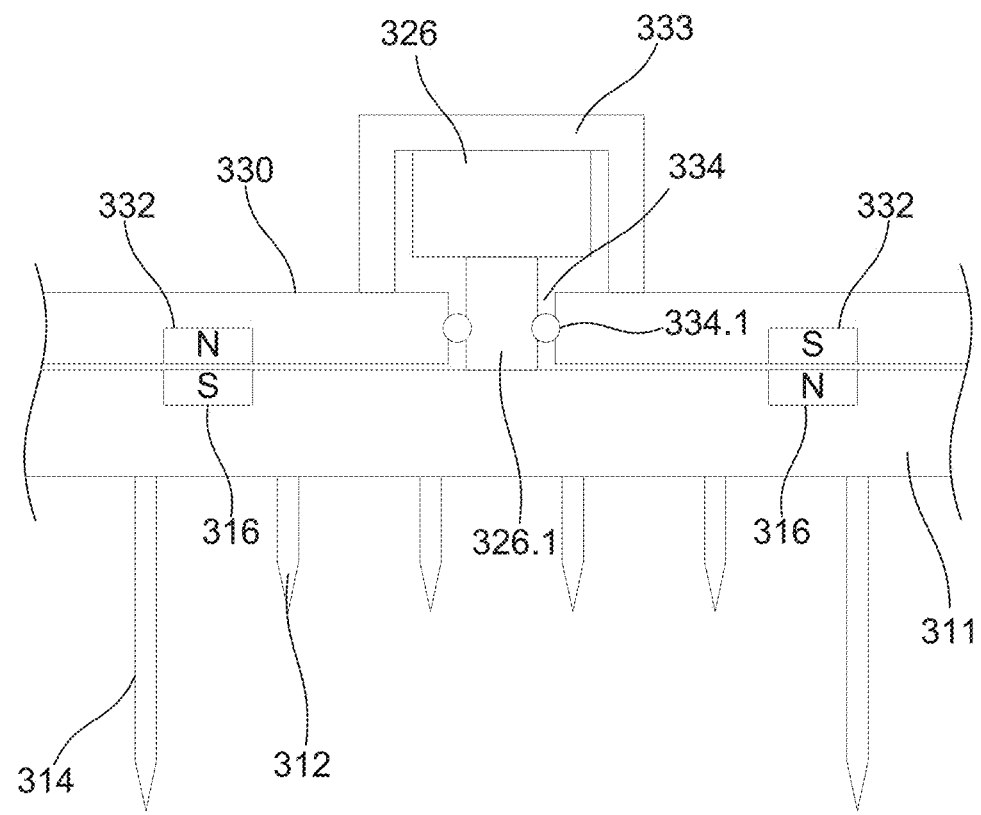
FIG. 3J is a schematic side view of an example actuator arrangement.

In the example of FIG. 3J, the substrate also includes coupling members 316, such as magnets, which can be used to attach the substrate to the housing 330.

Figure 3K:
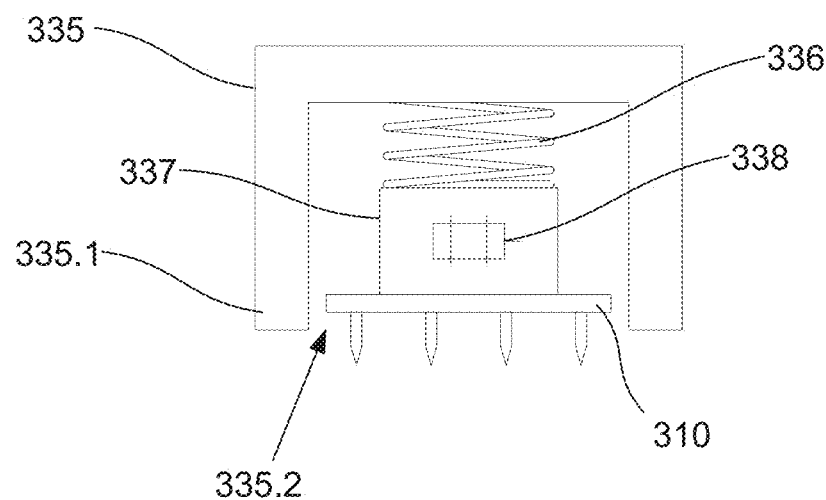
FIG. 3K is a schematic side view of a further example actuator arrangement.

A further example actuator arrangement will now be described with reference to FIG. 3K.

In this example, the actuator arrangement includes an actuator housing 335 having a base 335.1 including an opening 335.2. The housing contains a spring 336 and mounting 337, which in use supports a patch 310 (and optional integrated reader). The mounting also optionally contains a piezoelectric actuator or offset motor 338.

In use, the actuator housing 335 is positioned so that a base 335.1 of the housing 335 abuts against the subject's skin, with the patch at least partially projecting through the opening 335.2. In one example, this is achieved by having an operator hold the actuator housing. However, this is not essential and additionally and/or alternatively, the actuator housing could be integrated into and/or form part of a monitoring device as described above.

In use, the spring 336 is configured to apply a continuous biasing force to the mounting 337, so the patch 310 is urged against the subject's skin. Additionally, the piezoelectric actuator or offset motor 338 can cause the mounting 337, and hence patch 310, to vibrate, thereby facilitating piercing and/or penetration of the stratum corneum by the microstructures.

Example microstructure arrangements will now be described in more detail with reference to FIGS. 4 to 8.

Figure 4A:
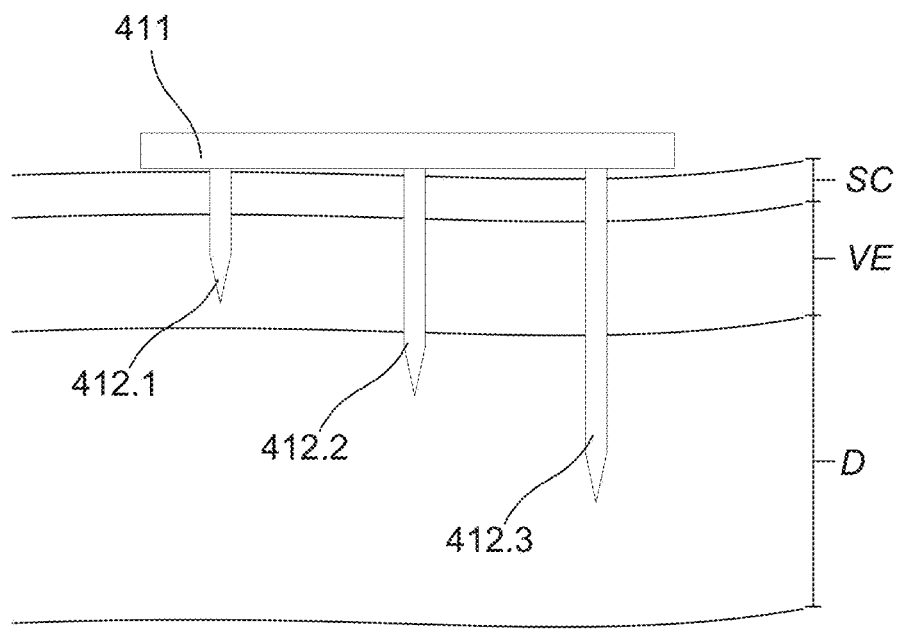
FIG. 4A is a schematic side view of a first example of a microstructure configuration.

In the example of FIG. 4A, different length microstructures are shown with a first microstructure 412.1 penetrating the stratum corneum and viable epidermis, but not breaching the dermis, a second microstructure 412.2 entering the dermis but only just passes the dermal boundary, whereas a third microstructure 412.3 penetrates the dermal layer at greater distance. It will be appreciated that the length of structure used will vary depending upon the intended application of the device, and specifically the nature of the barrier to be breached.

Figure 4B:
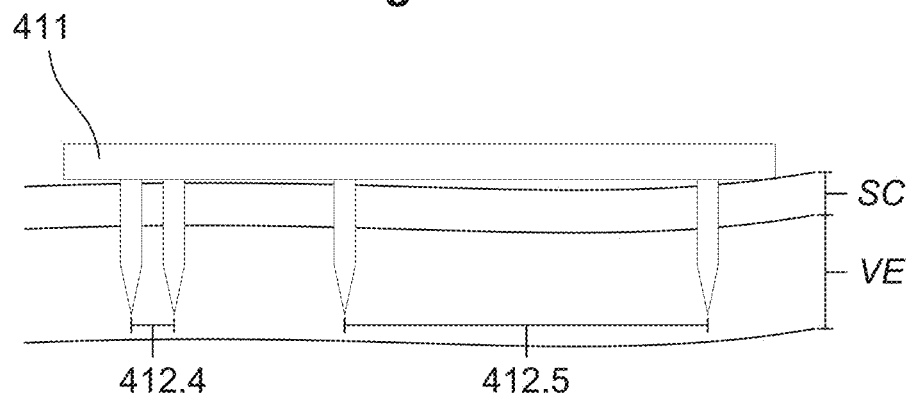
FIG. 4B is a schematic side view of a second example of a microstructure configuration.

In the example of FIG. 4B, pairs of microstructures are provided with a first microstructure pair 412.4 having a closer spacing and a second microstructure pair 412.5 having a relatively large spacing, which can be used to enable different properties to be detected, or different forms of stimulation to be performed.

For example, a greater electrode spacing can be used to perform impedance measurements of interstitial fluid and other tissues and liquids between the electrodes, whereas closer spaced electrodes are more suited to performing capacitive sensing to detect different analytes present on a surface of the electrodes.

Figures 4C, 4D:
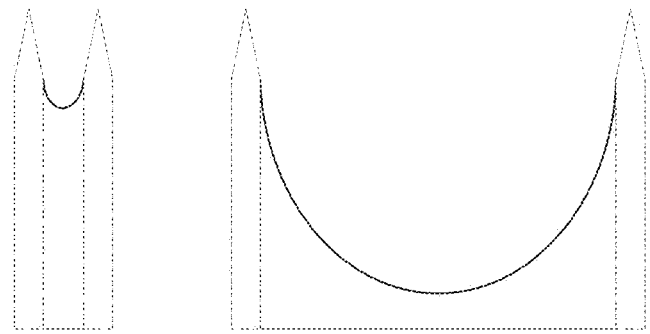
FIG. 4C is a graph illustrating the electric field between closely spaced electrodes.
FIG. 4D is a graph illustrating the electric field between distant spaced electrodes.

Additionally, the electrical field strength generated by applying a signal to the first and second microstructure pairs are shown in FIGS. 4C and 4D, highlighting that the field strength between the electrodes decreases as the spacing increases, which in turn impacts on the ability to perform stimulation. For example, by providing an array of closely spaced microstructures, this can be used to generate a highly uniform field within the subject, without requiring a large applied field. This can be used to allow the field to be used for stimulation, for example, to perform electroporation, or the like.

A specific example of a plate microstructure is shown is shown in FIGS. 5A to 5C.

In this example, the microstructure is a plate having a body 512.1 and a tip 512.2, which is tapered to facilitate penetration of the microstructure 512 into the stratum corneum. In this example, electrode plates 517 are provided on each side of the microstructure, with these being coupled via a single connection 513 to a connector 515 for onward connection to a sensor 321 and/or signal generator 323. This allows a signal to be measured from or applied to the electrode plates collectively. It will be appreciated however that this is not essential and independent connections could be provided allowing each of the electrodes to be driven or sensed independently. Additionally, each electrode 517 could be subdivided into multiple independent segments 517.1, 517.2, 517.3, 517.4, such that each face includes multiple electrodes.

Figure 5D:
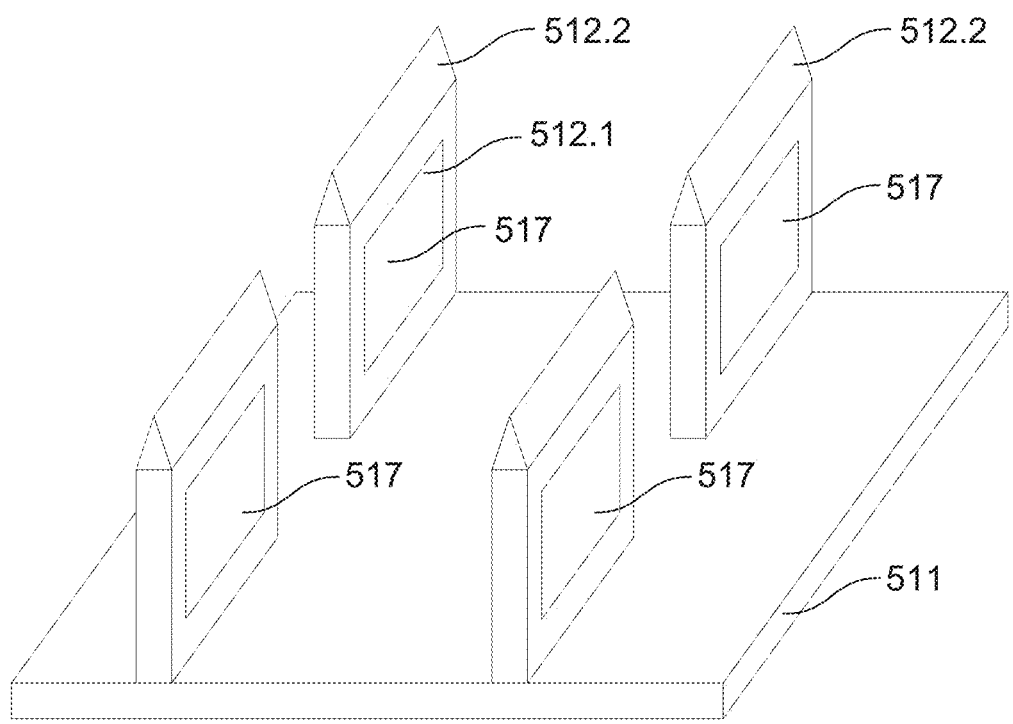
FIG. 5D is a schematic perspective topside view of an example of substrate including pairs of blade microstructures of FIGS. 5A and 5B.

As shown in FIGS. 5C and 5D, different arrangements could be used but in general, pairs of microstructures are formed with the microstructures facing each other allowing signals to be applied between the microstructures or measured between the microstructures. Again, different separations between electrodes in pairs of electrodes can be used to allow different measurements to be performed and/or to alter the profile of stimulation of the tissue between the electrodes.

Figure 5E:
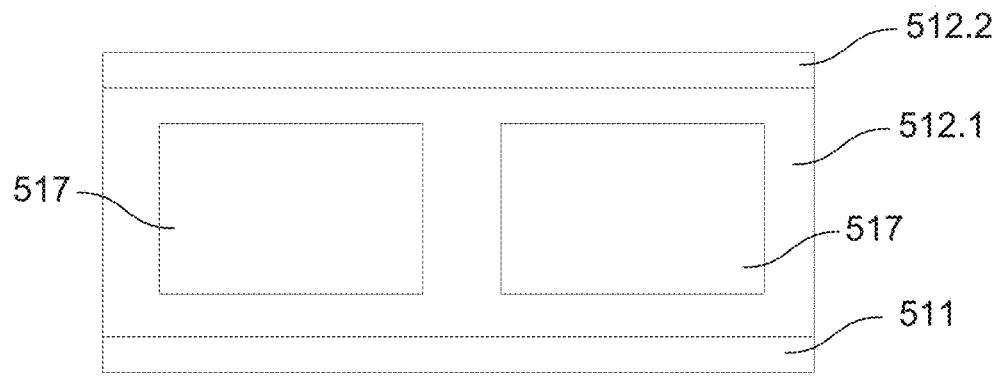
FIG. 5E is a schematic front view of an example of a blade microstructure.
Figure 5F:
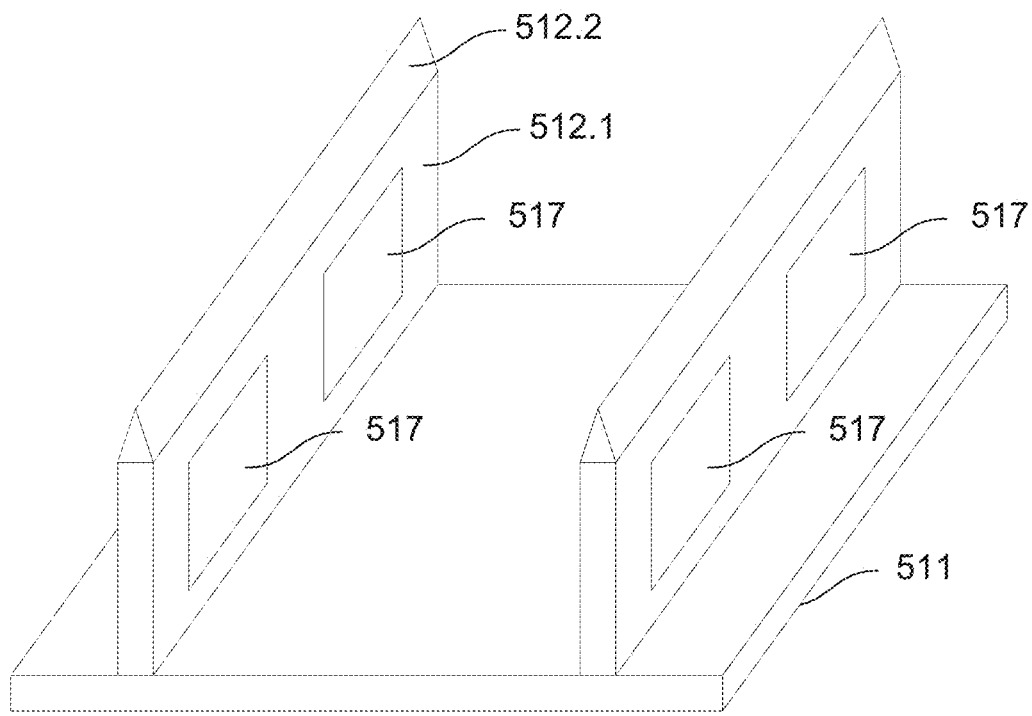
FIG. 5F is a schematic perspective topside view of an example of substrate including blade microstructures.

A further example of a blade microstructure is shown is shown in FIGS. 5E and 5F.

In this example, the microstructure is an elongate body 512.1 and tip 512.2, which is tapered to facilitate penetration of the microstructure 512. This is generally similar in profile to the plate arrangement described above, but in this example is significantly wider, and in one particular example, can extend substantially the entire distance across the substrate. In this example, the microstructures include multiple electrode plates 517 on each side of the microstructure. In this case, the substrate can include multiple spaced parallel blades, allowing signals to be applied across or measured between the electrodes on different blades. However, it will be appreciated that other configurations could be used, such as providing a single electrode, segmented electrodes, or having the entire microstructure act as an electrode.

In the example, shown the blade tip is parallel to the substrate, but this is not essential and other configurations could be used, such as having a sloped tip, so that the blade penetrates progressively along the length of the blade as it is inserted, which can in turn facilitate penetration. The tip may also include serrations, or similar, to further enhance penetration.

Figure 5G:
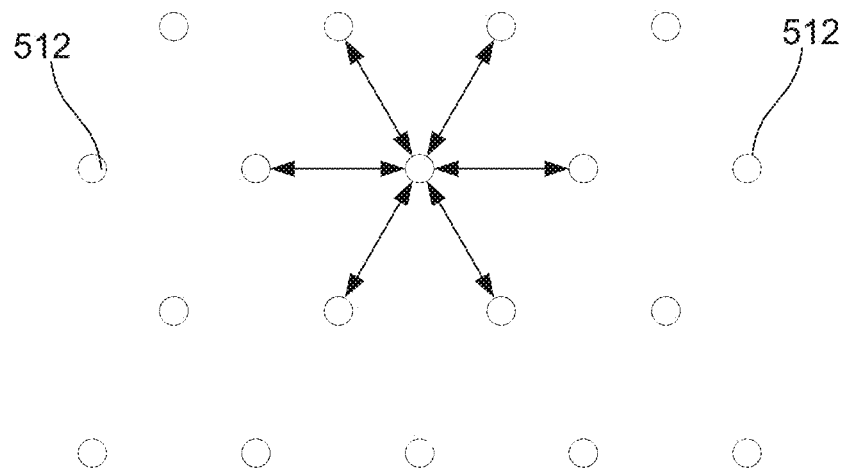
FIG. 5G is a schematic plan view of an example of a hexagonal grid microstructure array.
Figure 5H:
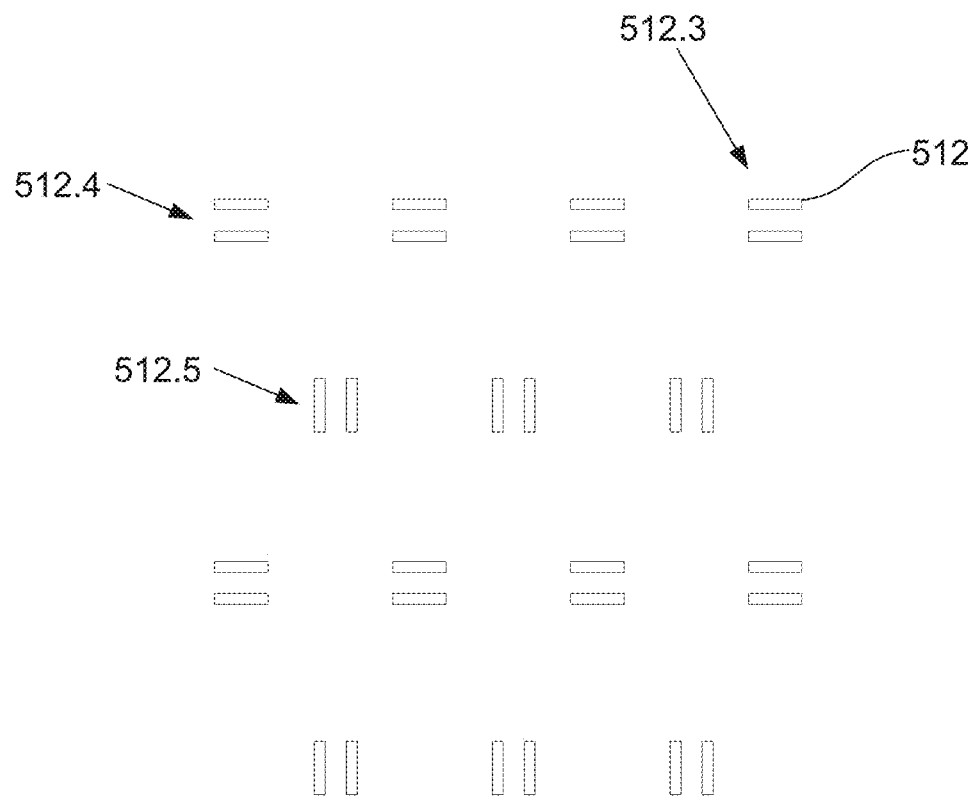
FIG. 5H is a schematic plan view of an alternative example of a grid of pairs of microstructures.
Figure 5I:
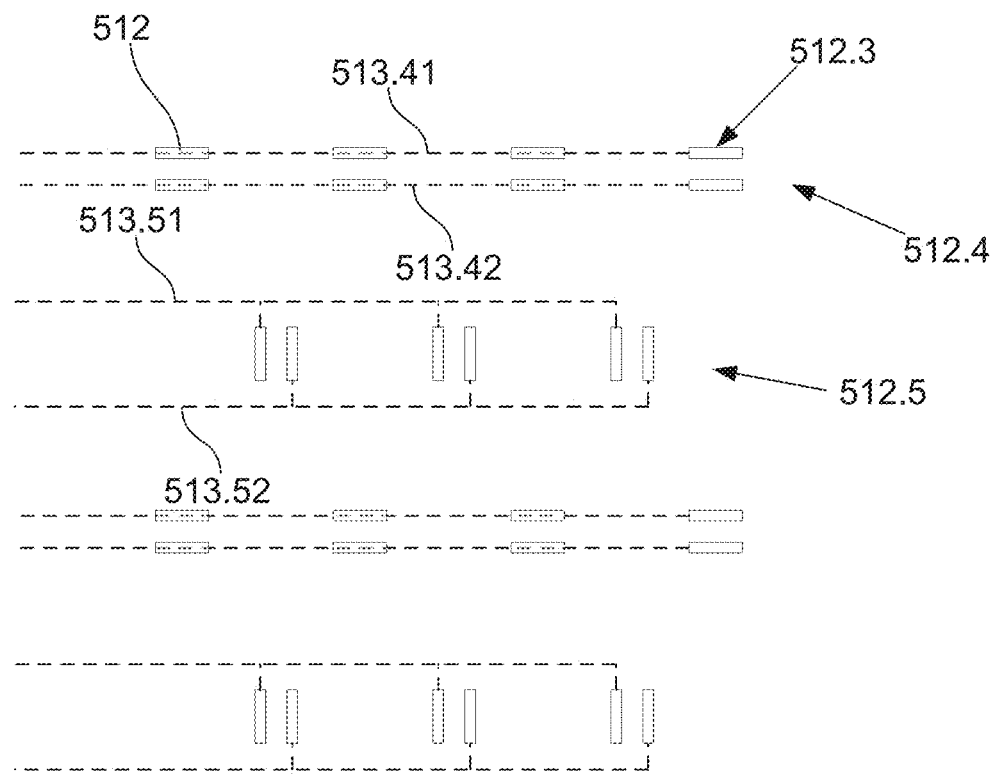
FIG. 5I is a schematic perspective view of an example of a grid of pairs of microstructures.
Figure 5J:
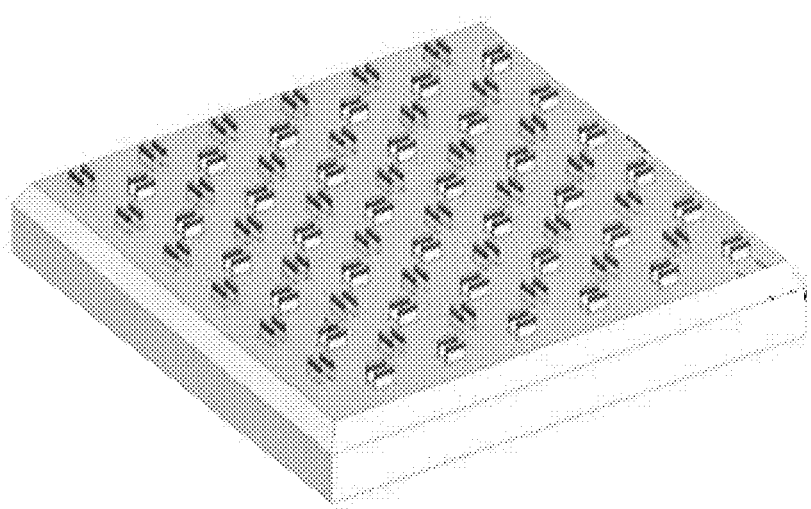
FIG. 5J is a schematic plan view of the grid of FIG. 5I showing example connections.

As mentioned above, in one example, microstructures are provided in a regular grid arrangement. However, in another example, the microstructures are provided in a hexagonal grid arrangement as shown in FIG. 5G. This is particularly advantageous as each microstructure is equally spaced to all of the nearest neighbour microstructures, as shown by the arrows, meaning measurements can be performed relative to any adjacent microstructure without requiring response or stimulation signals to be modified to account for different spacings.

A further example arrangement is shown in FIGS. 5H to 5K, in which microstructures 512 are arranged in pairs 512.3, and with pairs arranged in offset rows, 512.4, 512.5. In this example, pairs in different rows are arranged orthogonally, so that the microstructures extend in different directions. This avoids all microstructures being aligned, which can in turn render a patch vulnerable to lateral slippage in a direction aligned with the microstructures. Additionally arranging the pairs orthogonally reduces interference, such as cross talk, between different pairs of electrodes, improving measurement accuracy and accounting for tissue anisotropy, particularly when measurements are being performed via multiple microstructure pairs simultaneously.

In one example, pairs of microstructures in each row can be provided with respective connections 513.41, 513.42; 513.51, 513.52, allowing an entire row of microstructure pairs to be interrogated and/or stimulated simultaneously, whilst allowing different rows to be interrogated and/or stimulated independently.

Figure 5K:
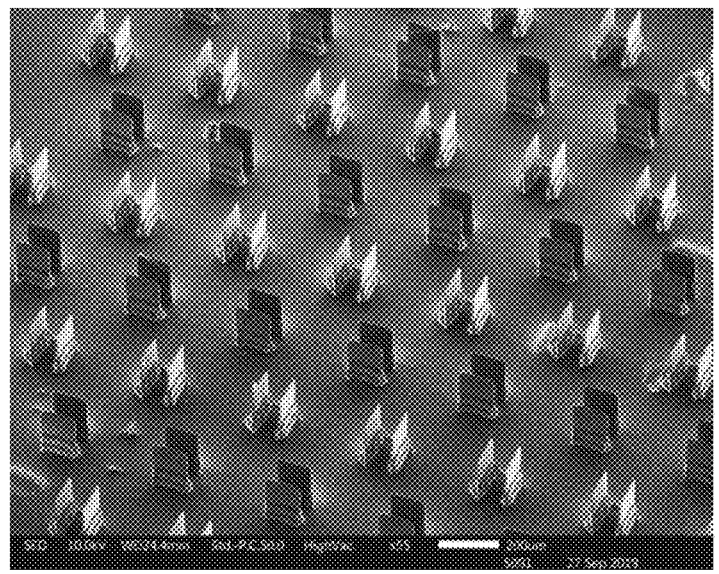
FIG. 5K is an image of an example of a patch including arrays of pairs of angularly offset plate microstructures.

A Scanning Electron Microscopy (SEM) image showing an array of pairs of offset plate microstructures is shown in FIG. 5K.

Figures 5L, 5M:
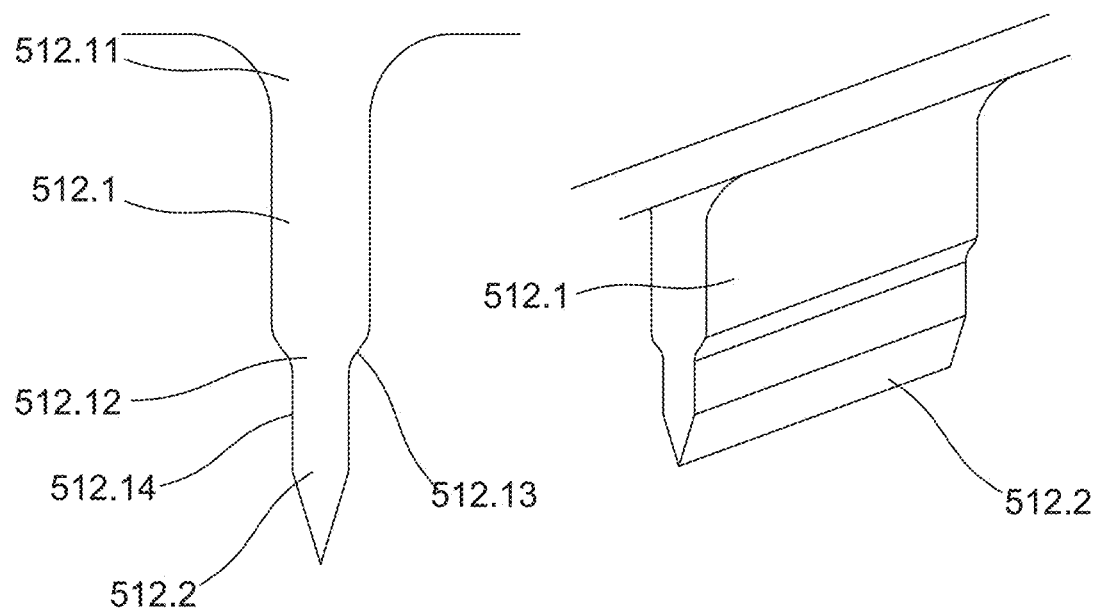
FIG. 5L is a schematic side view of a specific example of a plate microstructure.
FIG. 5M is a schematic perspective view of the plate microstructure of FIG. 5L.

Specific examples of microstructures for performing measurements in the epidermis are shown in FIGS. 5L and 5M.

In this example, the microstructures are plates or blades, having a body 512.1, with a flared base 512.11, where the body joins the substrate, to enhance the strength of the microstructure. The body narrows at a waist 512.12 to define shoulders 512.13 and then extends to a tapered tip 512.2, in this example, via an untapered shaft 512.14. Typical dimensions are shown in Table 1 below.

TABLE 1

| Parameter | Min. | Typical | Max. | Units |
| --- | --- | --- | --- | --- |
| Length | 50 | 150 | 300 | microns |
| Width | 50 | 150 | 300 | microns |
| Thickness | 10 | 25 | 50 | microns |
| Density | 100 | 600 | 5000 | $cm^{-2}$ |
| Tip radius | 0.1 | 1 | 5 | microns |
| Surface area per electrode | 2,000 | 22,500 | 200,000 | $micron^2$ |
| Buttress width at base | 30 | 75 | 150 | microns |

Figure 5N:
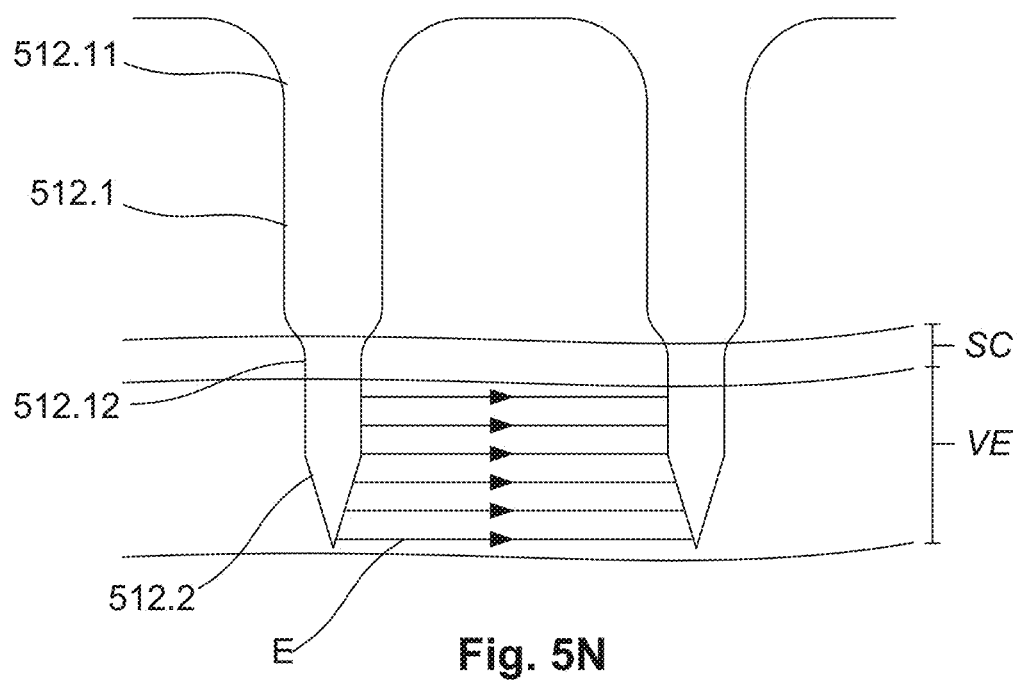
FIG. 5N is a schematic side view of an example of a pair of microstructures inserted into a subject for epidermal measurement.
Figure 5O:
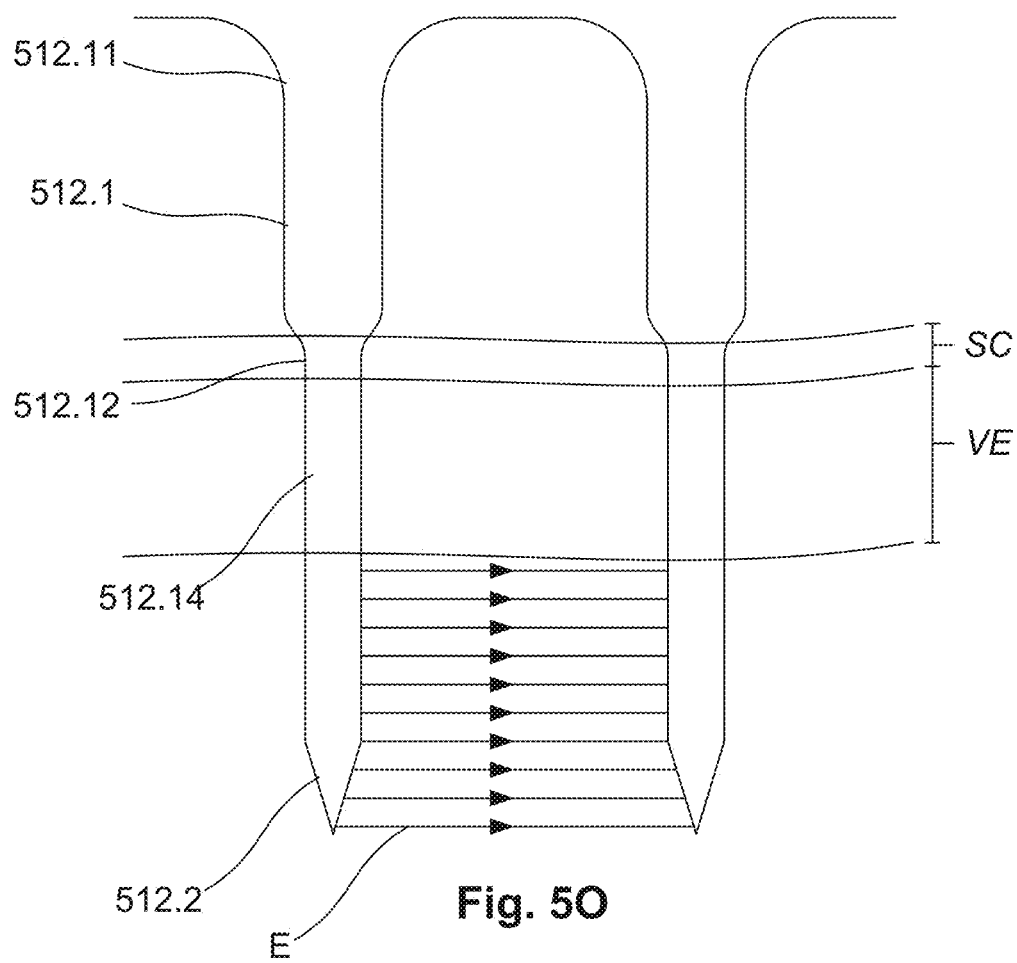
FIG. 5O is a schematic side view of an example of a pair of microstructures inserted into a subject for dermal measurement.

An example of a pair of the microstructures of FIGS. 5L and 5M on insertion into a subject is shown in FIG. 5N.

In this example, the microstructures are configured so that the tip 512.2 penetrates the stratum corneum SC and enters the viable epidermis VE. The waist 512.12, and in particular the shoulders 512.13 abut the stratum corneum SC so that the microstructure does not penetrate further into the subject, and so that the tip is prevented from entering the dermis. This helps avoid contact with nerves, which can lead to pain.

In this configuration, the body 512.1 of the microstructure can be coated with a layer of insulating material (not shown), with only the tip exposed. As a result a current signal applied between the microstructures, will generate an electric field E within the subject, and in particular within the viable epidermis VE, so that measurements reflect fluid levels in the viable epidermis VE.

However, it will be appreciated that other configurations can be used. For example, in the arrangement of FIG. 5M, the shaft 512.14 is lengthened so the tip 512.2 enters the dermis, allowing dermal (and optional epidermal) measurements to be performed.

In this example, typical dimensions are shown in Table 2 below.

TABLE 2

| Parameter | Min. | Typical | Max. | Units |
| --- | --- | --- | --- | --- |
| Length | 50 | 250 | 450 | microns |
| Width | 50 | 250 | 450 | microns |
| Thickness | 10 | 30 | 50 | microns |
| Density | 100 | 600 | 5000 | $cm^{-2}$ |
| Tip radius | 0.1 | 1 | 5 | microns |
| Surface area per electrode | 10,000 | 62,500 | 427,000 | $micron^2$ |
| Buttress width at base | 30 | 75 | 150 | microns |

An example of the inter and intra pair spacing for these configurations are shown in Table 3 below.

TABLE 3

| Parameter | Min. | Typical | Max. | Units |
| --- | --- | --- | --- | --- |
| Separation between microstructures in a group or pair | 10 | 100 | 1000 | microns |
| Separation between groups of microstructures | 200 | 500 | 1000 | microns |

Figure 6A:
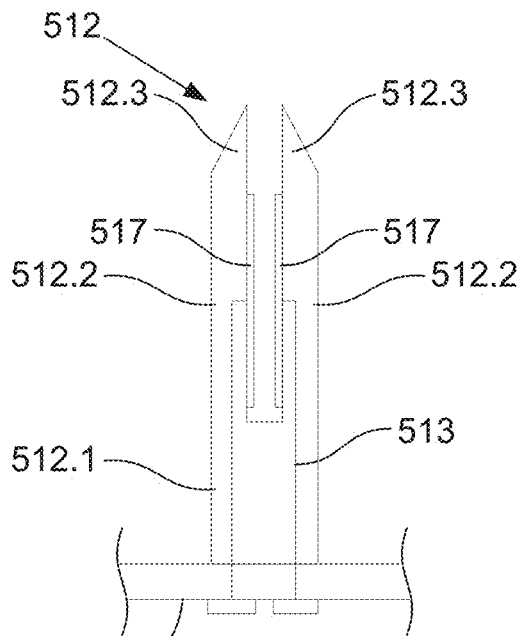
FIG. 6A is a schematic side view of a second example of a microstructure.
Figure 6B:
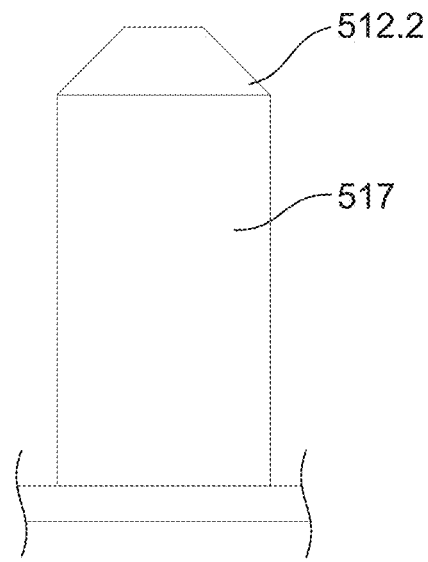
FIG. 6B is a schematic front view of the microstructure of FIG. 6A.

A further example arrangement is shown at FIGS. 6A and 6B, with the microstructure again including a generally similar plate like arrangement, with the microstructure including spaced apart prongs 612.2, each having an electrode 617 thereon, so that the electrodes are on faces between the prongs 612.2, again allowing for the application of a highly uniform field, or to allow capacitive sensing to be performed.

Figure 7A:
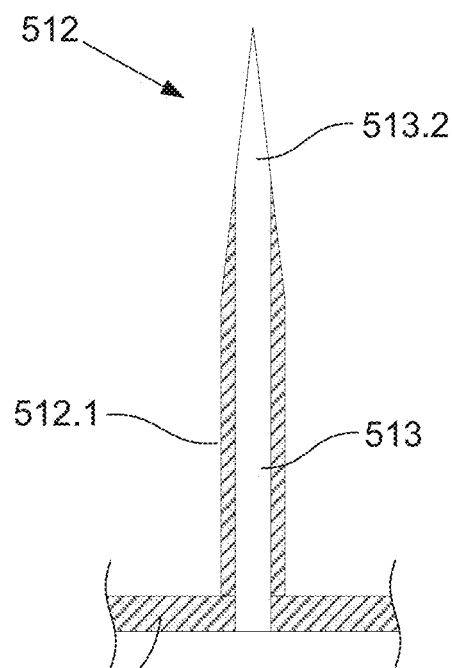
FIG. 7A is a schematic diagram of a third example of a microstructure.
Figure 7B:
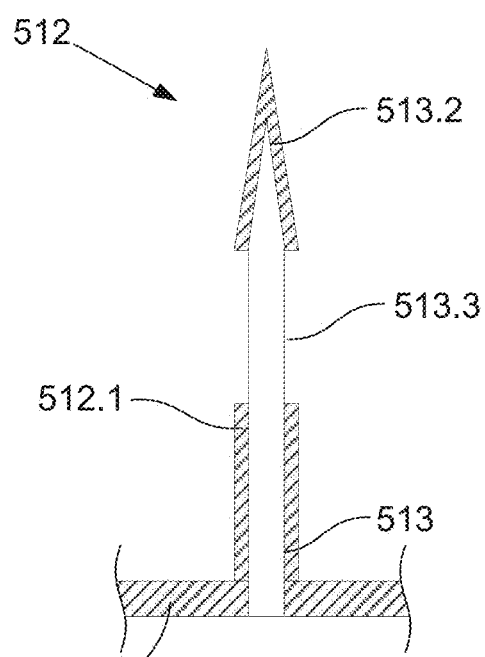
FIG. 7B is a schematic diagram of a modified version of the microstructure of FIG. 7A.

A further example of a microstructure is shown at FIG. 7A and FIG. 7B, which includes a body 512.1 containing a core 513 that is conductive, covered by an insulating layer 512.1, which in one example could be a polymer or other material. In this instance, the core 513 terminates at an opening 513.2 allowing electrical signals to be communicated via the outlet. Additionally, and/or alternatively, ports 513.3 may also be provided extending through the insulating layer, allowing electrical signals to be communicated midway along the structure as shown at FIG. 7B, allowing measurements to be performed at targeted depths within the viable epidermis.

It will also be appreciated that when pairs of microstructures are used, electrodes could be provided on an inner face of the pair only, for example, by insulating an outer face of the pair, to thereby reduce electrical interference between different pairs of microstructures.

An alternative technique for manufacturing microstructures will now be described with reference to FIGS. 8A to 8E.

In this example, a carrier wafer 891 is provided and spin coated with a photopolymer layer 892. The photopolymer layer 892 is selectively exposed to UV illumination and crosslinked, to create structural regions 892.1, which in this example form a substrate. A second photopolymer layer 893 is spun coated onto the first layer 891, and exposed to UV illumination and cross linked to form second structural regions 893.1, which in this example form microstructures, extending from the substrate. The carrier wafer and non-crosslinked polymer are removed to create the microstructures shown in FIG. 8D.

Figure 8A:
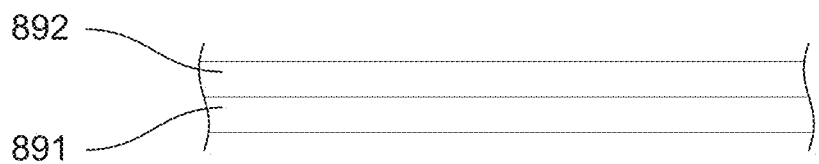
FIG. 8A is a schematic side view of an example of a first step of a microstructure construction technique.
Figure 8B:
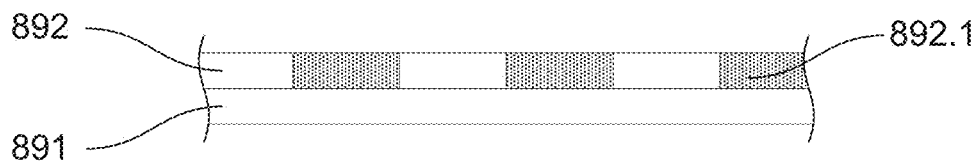
FIG. 8B is a schematic side view of an example of a second step of a microstructure construction technique.
Figure 8C:
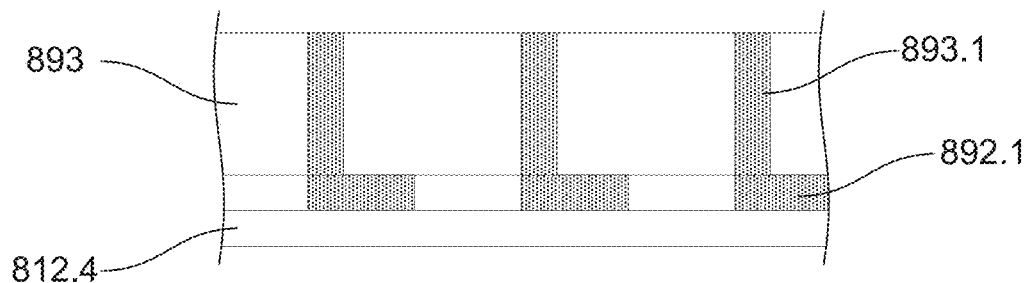
FIG. 8C is a schematic side view of an example of a third step of a microstructure construction technique.
Figure 8D:
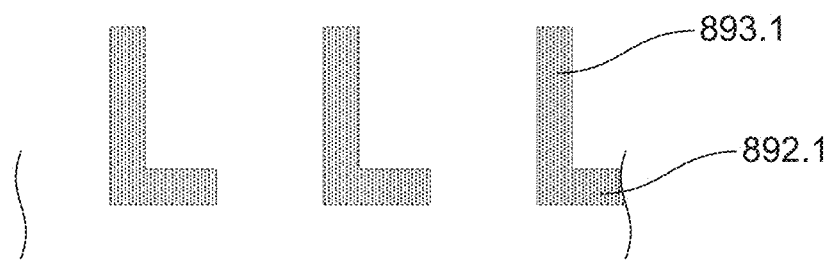
FIG. 8D is a schematic side view of a first example of a microstructure configuration created using the construction technique of FIGS. 8A to 8C.
Figure 8E:
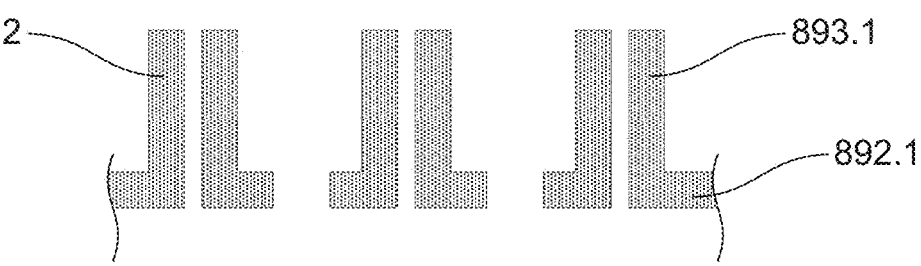
FIG. 8E is a schematic side view of a second example of a microstructure configuration created using the construction technique of FIGS. 8A to 8C.

It will be appreciated that this layering technique can be used to create a wide range of different microstructure configurations, and alternative design is shown in FIG. 8E.

Figure 9:
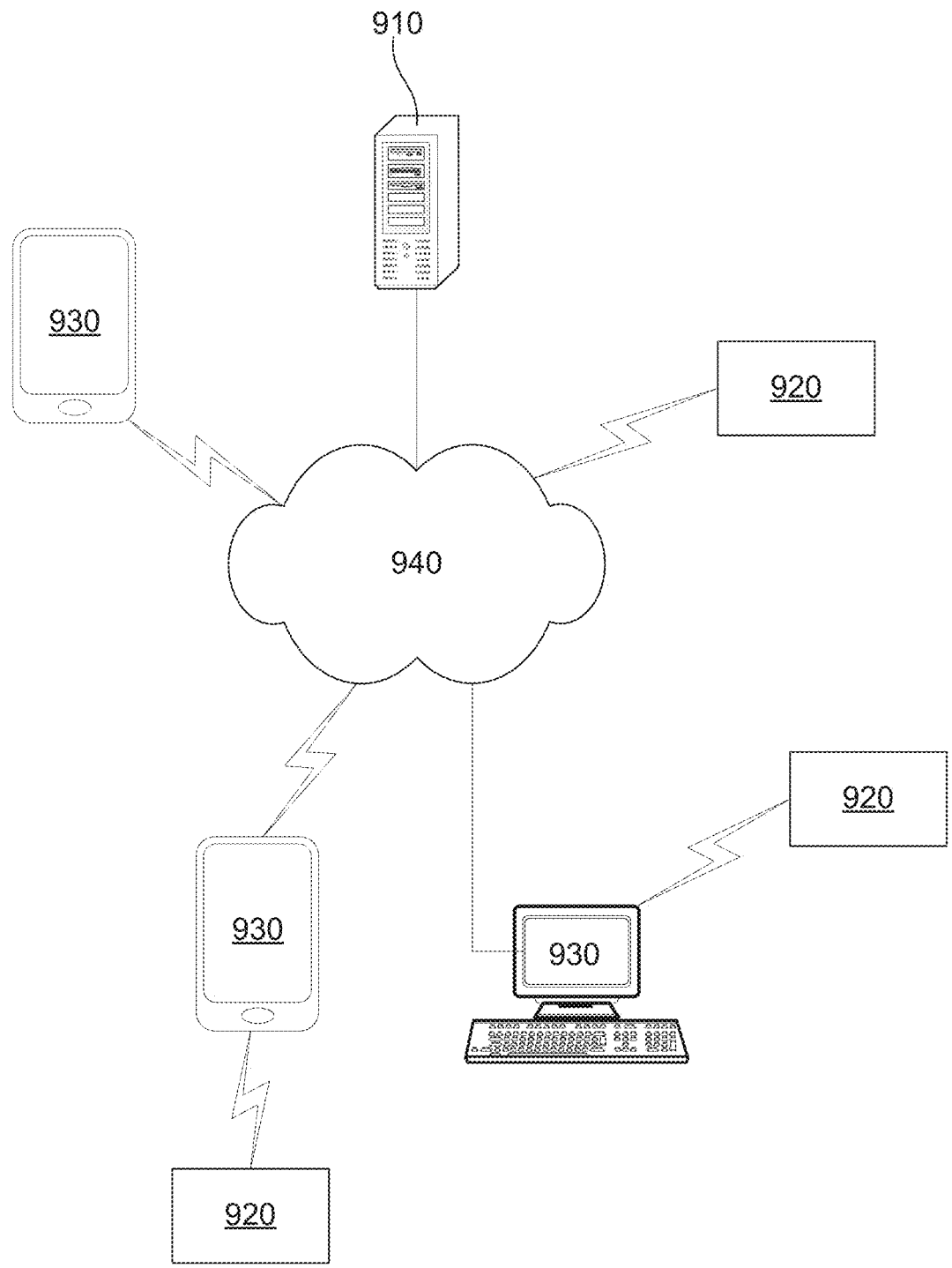
FIG. 9 is a schematic diagram of an example of a distributed computer architecture.

In one example, the monitoring device operates as part of a distributed architecture, an example of which will now be described with reference to FIG. 9.

In this example, one or more processing systems 910 are coupled via communications networks 940, and/or one or more local area networks (LANs), to a number of client devices 930 and monitoring devices 920. The monitoring devices 920 could connect direction to the networks, or could be configured to connect to a client device 930, which then provides onward connectivity to the networks 940. It will be appreciated that the configuration of the networks 940 are for the purpose of example only, and in practice the processing systems 910, client devices 930 and monitoring devices 930 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

In one example, each processing system 910 is configured to receive subject data from a monitoring device 920 or client device 930, and analyse the subject data to generate one or more health status indicators, which can then be provided to a client device 930 or monitoring device 920 for display. Whilst the processing system 910 is a shown as a single entity, it will be appreciated that the processing system 910 can be distributed over a number of geographically separate locations, for example by using processing systems 910 and/or databases that are provided as part of a cloud based environment. However, the above described arrangement is not essential and other suitable configurations could be used.

Figure 10:
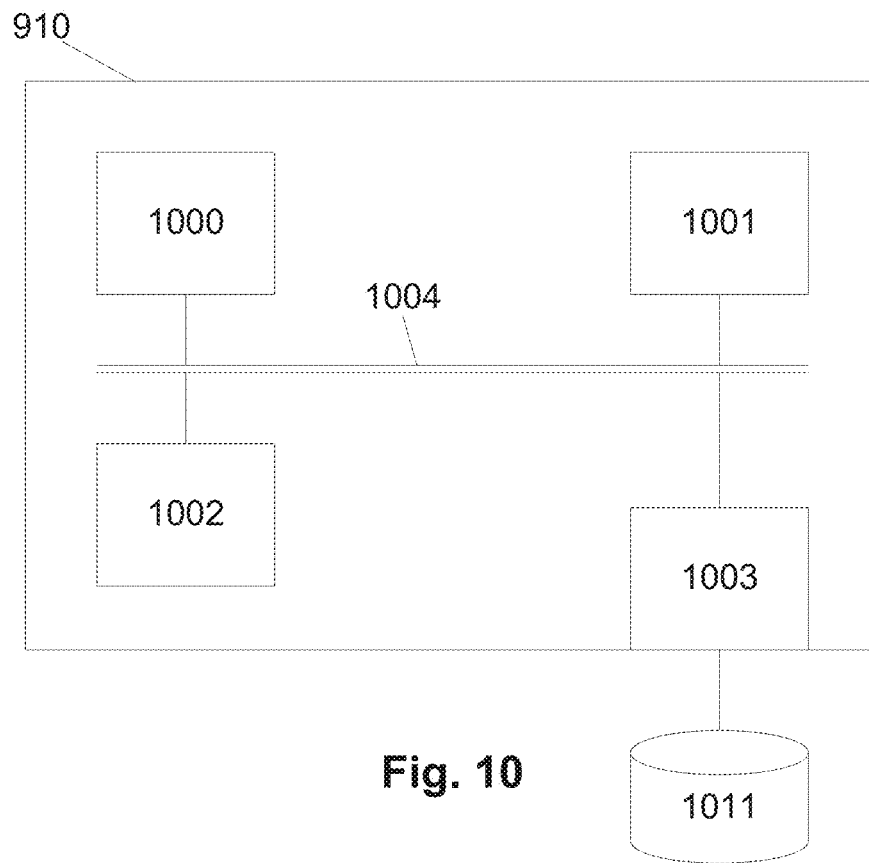
FIG. 10 is a schematic diagram of an example of a processing system.

An example of a suitable processing system 910 is shown in FIG. 10.

In this example, the processing system 910 includes at least one microprocessor 1000, a memory 1001, an optional input/output device 1002, such as a keyboard and/or display, and an external interface 1003, interconnected via a bus 1004 as shown. In this example the external interface 1003 can be utilised for connecting the processing system 910 to peripheral devices, such as the communications network 940, databases 1011, other storage devices, or the like. Although a single external interface 1003 is shown, this is for the purpose of example only, and in practice multiple interfaces using various methods (e.g., Ethernet, serial, USB, wireless or the like) may be provided.

In use, the microprocessor 1000 executes instructions in the form of applications software stored in the memory 1001 to allow the required processes to be performed. The applications software may include one or more software modules, and may be executed in a suitable execution environment, such as an operating system environment, or the like.

Accordingly, it will be appreciated that the processing system 910 may be formed from any suitable processing system, such as a suitably programmed client device, PC, web server, network server, or the like. In one particular example, the processing system 910 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Figure 11:
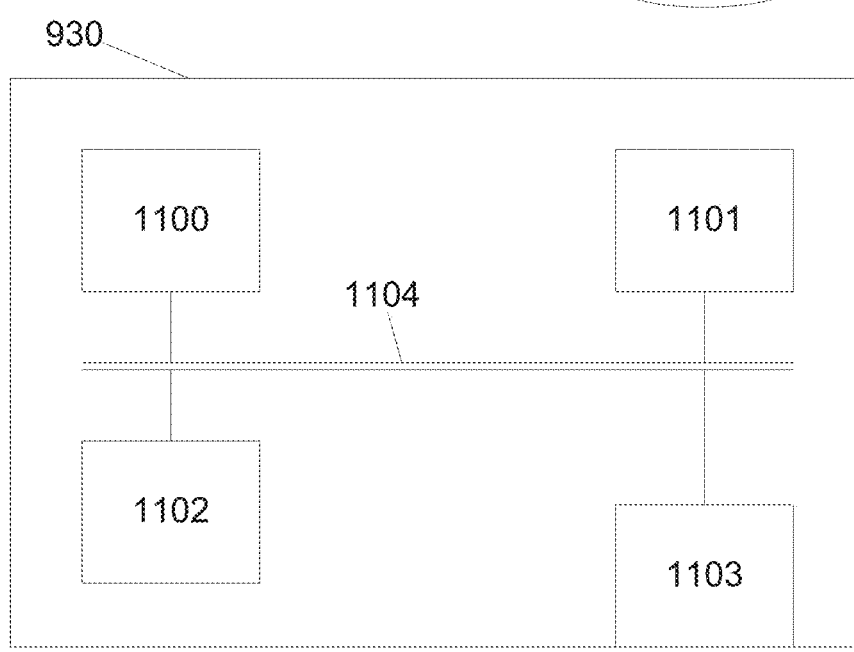
FIG. 11 is a schematic diagram of an example of a client device.

An example of a suitable client device 930 is shown in FIG. 11.

In one example, the client device 930 includes at least one microprocessor 1100, a memory 1101, an input/output device 1102, such as a keyboard and/or display, and an external interface 1103, interconnected via a bus 1104 as shown. In this example the external interface 1103 can be utilised for connecting the client device 930 to peripheral devices, such as the communications networks 940, databases, other storage devices, or the like. Although a single external interface 1103 is shown, this is for the purpose of example only, and in practice multiple interfaces using various methods (e.g., Ethernet, serial, USB, wireless or the like) may be provided.

In use, the microprocessor 1100 executes instructions in the form of applications software stored in the memory 1101 to allow communication with the processing system 910 and/or monitoring device 920.

Accordingly, it will be appreciated that the client devices 1130 may be formed from any suitable processing system, such as a suitably programmed PC, Internet terminal, laptop, or hand-held PC, and in one preferred example is either a tablet, or smart phone, or the like. Thus, in one example, the client device 1130 is a standard processing system such as an Intel Architecture based processing system, which executes software applications stored on non-volatile (e.g., hard disk) storage, although this is not essential. However, it will also be understood that the client devices 1130 can be any electronic processing device such as a microprocessor, microchip processor, logic gate configuration, firmware optionally associated with implementing logic such as an FPGA (Field Programmable Gate Array), or any other electronic device, system or arrangement.

Examples of the processes for performing measurements and generating indicators will now be described in further detail. For the purpose of these examples it is assumed that one or more processing systems 910 acts to analyse received subject data and generate resulting indicators. Measurements are performed by the monitoring devices 920, with subject data being transferred to the processing systems 910 via the client devices 230. In one example, to provide this in a platform agnostic manner, allowing this to be easily accessed using client devices 930 using different operating systems, and having different processing capabilities, input data and commands are received from the client devices 930 using via a webpage, with resulting visualisations being rendered locally by a browser application, or other similar application executed by the client device 930. The processing system 910 is therefore typically a server (and will hereinafter be referred to as a server) which communicates with the client device 930 and/or monitoring device 920, via a communications network 940, or the like, depending on the particular network infrastructure available.

To achieve this the server 910 typically executes applications software for hosting webpages, as well as performing other required tasks including storing, searching and processing of data, with actions performed by the processing system 910 being performed by the processor 1000 in accordance with instructions stored as applications software in the memory 1001 and/or input commands received from a user via the I/O device 1002, or commands received from the client device 1030.

It will also be assumed that the user interacts with the server 910 via a GUI (Graphical User Interface), or the like presented on the client device 930, and in one particular example via a browser application that displays webpages hosted by the server 910, or an App that displays data supplied by the server 910. Actions performed by the client device 930 are performed by the processor 1100 in accordance with instructions stored as applications software in the memory 1101 and/or input commands received from a user via the I/O device 1102.

However, it will be appreciated that the above described configuration assumed for the purpose of the following examples is not essential, and numerous other configurations may be used. It will also be appreciated that the partitioning of functionality between the monitoring devices 920, client devices 930, and the server 910 may vary, depending on the particular implementation.

Figure 12A:
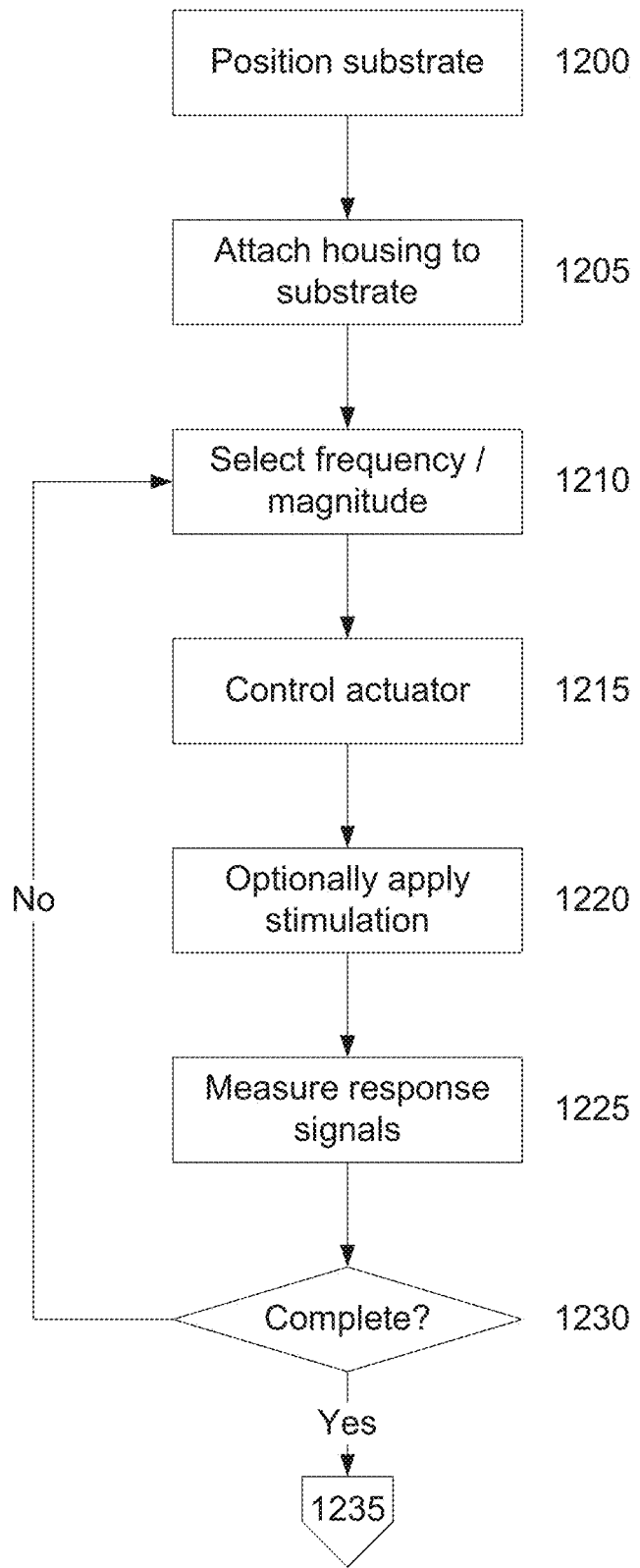
FIGS. 12A and 12B are a flow chart of an example of a process for performing a measurement on a biological subject.
Figure 12B:
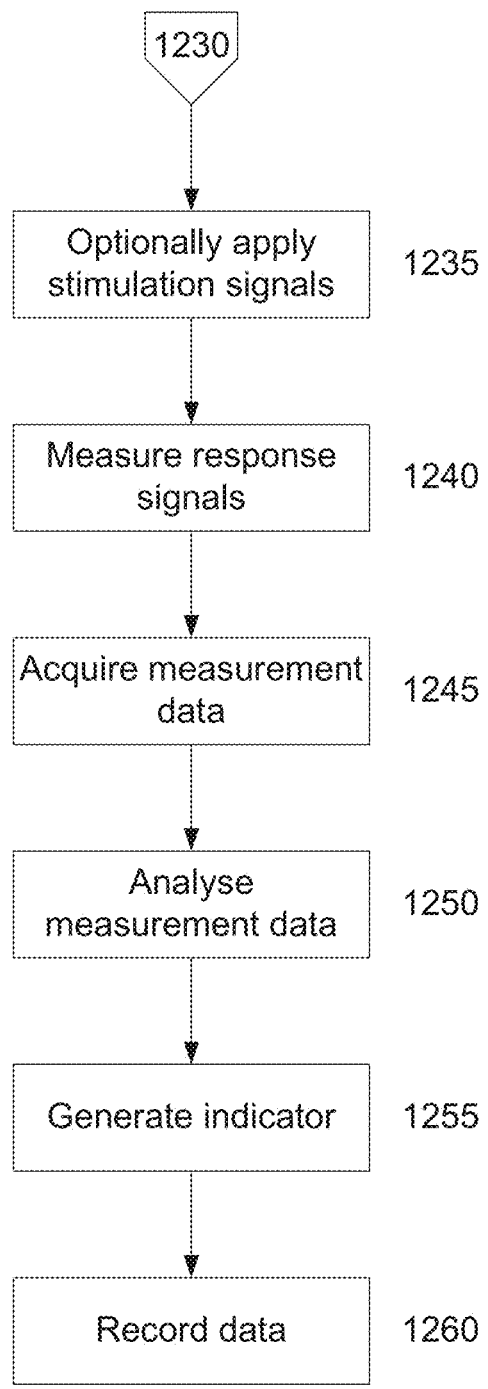

An example of process for performing measurements on a subject will now be described in more detail with reference to FIGS. 12A and 12B.

In this example, a process for applying a patch including the substrate and microstructures is shown in steps 1200 to 1230, whilst a measurement process is shown in steps 1235 to 1260. In this regard, it will be appreciated that for patches that are used for performing multiple measurements over a period of time, steps 1200 to 1230 would only be performed a single time, with steps 1235 to 1260 being repeated as needed.

Furthermore, for the purpose of this example, it is assumed that the system includes a reader formed by the housing 330 and associated signal generator, sensor and processing electronics. The reader could be integral with the patch 310 and/or separate from the patch 310 depending on the preferred implementation.

At step 1200, the substrate is provided in a desired position, with the substrate and microstructures in place against the subject. At step 1205, assuming the reader is not integrated into the patch 310, the housing 330 is attached to the substrate 311, for example, by magnetically or otherwise coupling the housing and substrate, or by holding the housing in contact with the patch 310.

At step 1210, the processing device 322 selects a frequency/magnitude for the actuator. This can be a standard value and/or might depend on the barrier to be breached, so that different values might be selected for different sites on a subject, and/or for different subjects.

At step 1215, the actuator 326 is controlled, to thereby begin vibration of the microstructures, and hence facilitate movement of the microstructures within the subject.

At step 1220 stimulation is optionally applied, with response signals being measured at step 1225, allowing the processing device 322 to monitor breaching of the functional barrier and/or a depth of penetration. The mechanism for achieving this will depend on the nature of the response signals and optional stimulation. For example, the stimulation and response could be used to derive an impedance, with the impedance value altering as the microstructures penetrate the stratum corneum and enter the viable epidermis.

At step 1230, the processing device 322 optionally determines if breaching or penetration are complete and if not the process returns to step 1210 to select a different frequency and/or magnitude. Thus, this allows the frequency and/or magnitude of any applied force to be adjusted continuously as the substrate and microstructures are applied, and in particular as the microstructures breach and optionally penetrate the functional barrier. In one example, this is used to allow the frequency to decrease during insertion, whilst the force progressively increases until the barrier is breached, at which point the force decreases. In this regard, it has been found that this can facilitate penetration of the barrier.

Once the patch is applied, measurements can commence. In this regard, if the reader is integrated into the patch, measurements can be performed as needed. Alternatively, if the reader is separate, this may require the reader be brought into proximity and/or contact with the patch, to allow a measurement to be performed.

In this example, at step 1235 the monitoring device 920 applies one or more stimulatory signals to the subject, and then measures response signal at step 1240. The response signals are measured by the sensor 321, which generates measurement data that is provided to the processing device 322 at step 1245.

In one example, the monitoring device 920 then transfers the measurement data to a client device 930 for further processing. In particular, the client device 930 might perform preliminary pre-processing of data and may append additional information, for example derived from onboard sensors, such as GPS or other like, to thereby add time or location information, or the like. This information can be useful in circumstances, such as tracking spread of infectious diseases or similar.

The resulting data is collated, for example by creating subject data, which can then be transferred to a server 910 allowing this to be analysed at step 1250. However, it will also be appreciated that the analysis could be performed on board the reader, and an indicator derived by performing the analysis could be displayed on the reader.

The nature of the analysis will vary depending on the preferred implementation and a wide range of options are envisaged.

When performing fluid level measurements, alternating electrical current signals are applied to the subject via a pair of microstructures, with resulting voltage signals being measured via the same microstructures. The magnitude and phase of the applied current and resulting voltage can then be used to calculate an impedance value, which depends on fluid volumes and ion concentrations within the subject. Accordingly, the measured impedance value can be correlated with a fluid level, allowing a subject hydration to be determined, and an example of this will be described in more detail below.

It will further be appreciated that different information can be derived depending on the frequency at which measurements are performed. For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, which are indicative of extracellular fluid levels.

Alternatively, the applied signal can have a relatively high frequency, such as above 200 kHz, and more typically above 500 kHz, or 1000 kHz. In this instance, such high frequency signals can be used as an estimate of the impedance at infinite applied frequency, which is in turn indicative of a combination of the extracellular and intracellular fluid levels.

Alternatively and/or additionally, the system can use Bioimpedance Spectroscopy (BIS) in which impedance measurements are performed at multiple frequencies, which can then be used to derive information regarding both intracellular and extracellular fluid levels, for example by fitting measured impedance values to a Cole model.

For example, the subject data could be used in conjunction with previously collected subject data in order to perform a longitudinal analysis, examining changes in measured values over time. Additionally and/or alternatively, the subject data could be analysed using a machine learning model or similar.

One or more indicators are generated at step 1255, with the nature of the indicators and the manner in which these are generated varying depending upon the preferred implementation and the nature of the analysis being performed.

At step 1260 data, such as the subject data, the indicators, or the measurement data, are recorded allowing this to be subsequently accessed as needed. The indicator may also be provided to the client device 930 and/or monitoring device 920, allowing this to be displayed.

Figure 13:
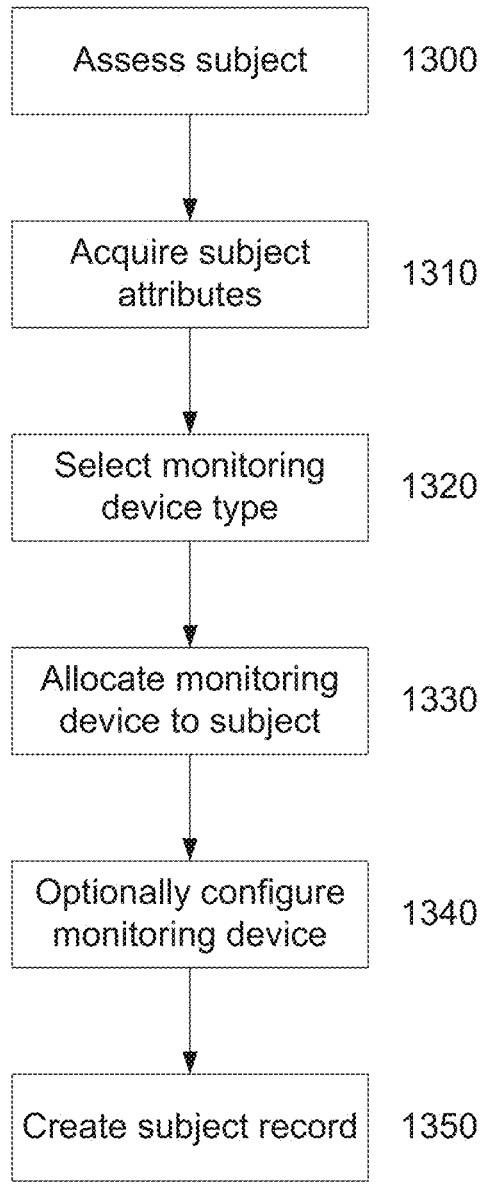
FIG. 13 is a flow chart of an example of a process for creating a subject record.

In one example, monitoring devices are allocated to respective users, with this allocation being used to track measurements for the subject. An example of a process for allocating a monitoring device 920 to a subject will now be described with reference to FIG. 13.

In this example, the subject initially undergoes an assessment at step 1300, with this process being performed by a clinician. The clinician will use the assessment to guide the type of monitoring that needs to be performed, for example to identify particular biomarkers that are to be measured, which in turn may depend on any symptoms or medical diseases, disorders or conditions suffered by the subject. As part of this process, the clinician will typically acquire subject attributes at step 1310, such as measurement of weight, height, age, sex, details of medical interventions, or the like. This can be performed using a combination or techniques, such as querying a medical record, asking questions, performing measurements or the like.

Once the assessment has been completed, a monitoring device type can be selected at 1320, with this being performed based on the measurements that are required. In this regard, it will be appreciated that different combinations of microstructure arrangement and sensing modalities can be used in order to allow a range of different measurements to be performed, and it is therefore important that the correct selection is made to enable the measurements to be collected. A specific monitoring device 920 is then allocated to the subject at step 1330. In this regard, in each device will typically include a unique identifier, such as a MAC (Media Access Control) address or other identifier, which can be used to uniquely associate the monitoring device with the subject.

At step 1340 the monitoring device 920 can optionally be configured, for example to update firmware or the instruction set needed to perform the respective measurements. At step 1350, a subject record is created, which is used to store details associated with the subject, including subject attributes, subject data, indicators, or any other relevant information. Additionally, the subject record will also typically include an indication of the monitoring device identifier, thereby associating the monitoring device with the subject.

Figure 14A:
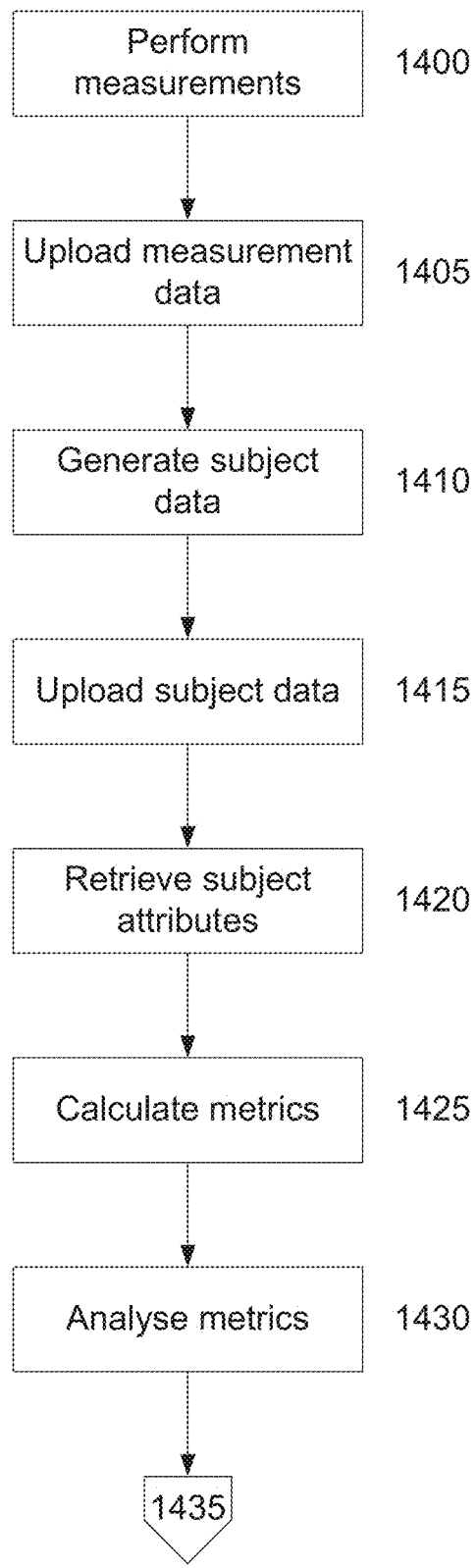
FIGS. 14A and 14B are a flow chart of a specific example of a process for performing measurements in a biological subject.
Figure 14B:
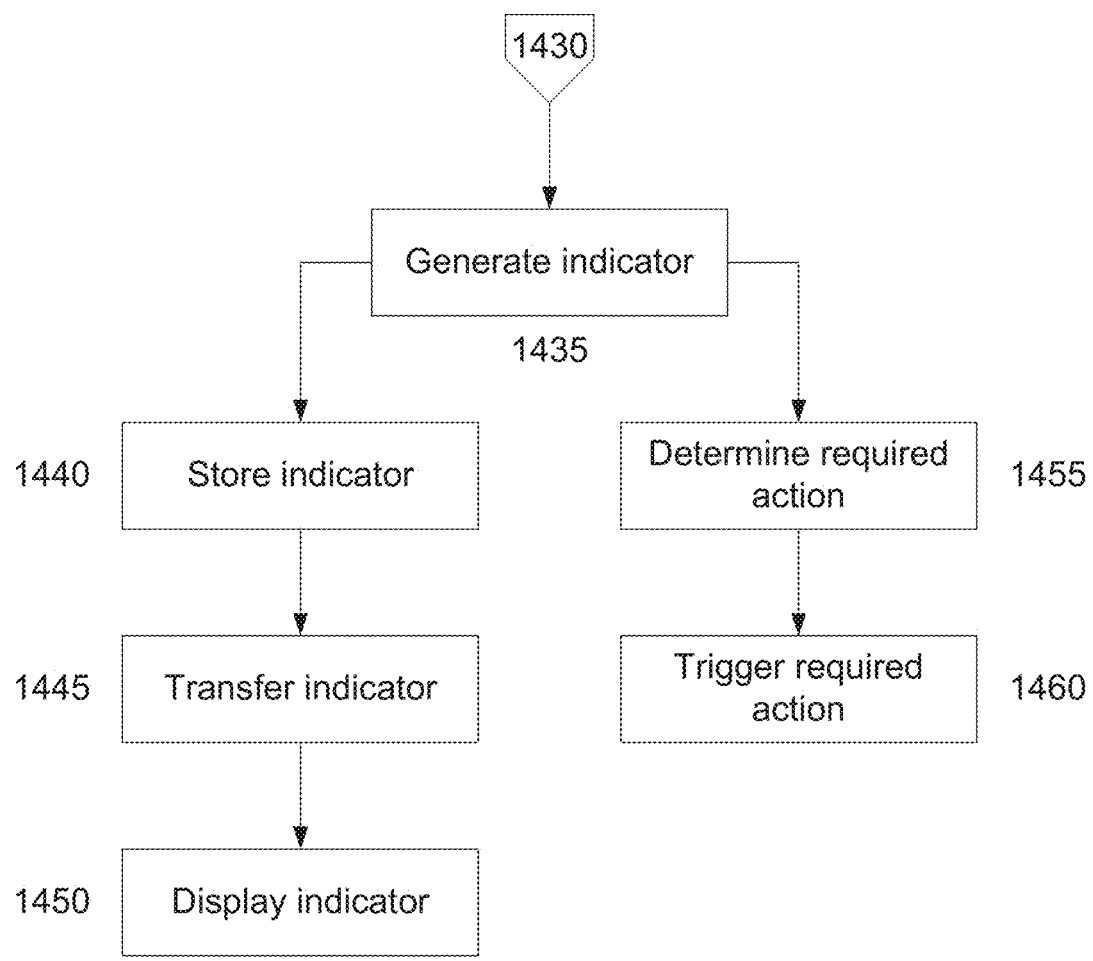

An example of the process of using the device to perform measurements will now be described with reference to FIGS. 14A and 14B.

In this example, at step 1400 one or more measurements are performed. The measurements are performed by utilising the process described above, for example by having the monitoring device apply stimulatory signals and measure response signals. Measurement data is recorded based on the response signals with this being uploaded to the client device 930 at step 1405, allowing the client device 930 to generate subject data at step 1410. The subject data could simply be the measurement data, but may also include additional information provided by the client device 930. This allows user inputs to be provided via the client device 930, for example providing details of symptoms, changes in attributes or the like. The subject data is then uploaded to the server 910 at step 1415. The server 910 then retrieves one more subject attributes at step 1420, for example from the subject record, with the server 910 then calculating one or more metrics at step 1425.

At step 1430, the server 910 analyses the metrics. The manner in which this is performed will vary depending on the preferred implementation. For example, this could be achieved by applying the metrics to a computational model that embodies a relationship between a relevant health status and the one or more metrics. Alternatively, the metrics could be compared to defined thresholds, which can be established from a population of reference subjects, and which are used to represent certain diseases, disorders or conditions, such as the presence or absence of a medical condition. As a further option, the metrics could be compared to previous metrics for the subject, for example to examine changes in the metrics, which could in turn represent a change in health status. The results of the analysis can be used to generate one or more indicators at step 1435. In one example, the indicator can be in the form of a score representing a health status, or could be indicative of a presence, absence or degree of diseases, disorders or condition.

At step 1440 the indicator can be stored, with an indication of the indicator being transferred to the client device 930 at step 1445, allowing the indicator to be displayed, either by the client device 930 or the monitoring device 920 at step 1450.

Additionally, and/or alternatively, at step 1455 the indicator can be used to determine if an action is required, for example if an intervention should be performed. The assessment of whether an action is required could be performed in any one of a number of manners, but typically involves comparing the indicator to assessment criteria defining a predetermined threshold or range of acceptable indicator values. For example, comparing a hydration indicator to a range indicative of normal hydration, or comparing an analyte indicator indicative of a normal level or concentration of analytes.

The assessment criteria can also specify the action required if the indicator falls outside of the acceptable range, and any steps required to perform the action, allowing the action to be performed at step 1460. For example, in a theranostic application, this could involve causing the applying monitoring device to apply a stimulation signal to electrodes, thereby allowing one or more therapeutic agents to be released. Alternatively, if the subject is dehydrated, the action could include having the monitoring device provide a recommendation to the user to hydrate, whereas if certain analytes are detected, this could be indicative of a medical situation, in which the processing system or monitoring device could generate a notification which is provided to a clinician, or other nominated person or system, allowing them to be alerted. The notification could include any determined indicator and/or measured response signals, allowing the clinician to rapidly identify any interventions needed. Alternatively, the action could involve notifying the user, so for example, if the subject is dehydrated, the action could include having the monitoring device provide a recommendation to the user to hydrate.

It will be therefore be appreciated that this enables actions to be triggered as needed.

The above described processes describe transfer of data to remote systems for analysis, which can have a number of benefits. For example, this allows more complex analysis to be performed than would otherwise be the case with existing processing capabilities. This also allows remote oversight, for example, allowing a clinician to access records associated with multiple patients, in real-time, enabling the clinician to respond rapidly as needed. For example, in the event that measured data shows an indication of a deleterious health state, the clinician could be alerted or notified, allowing an intervention to be triggered. Additionally, collective monitoring provides public health benefits, for example to allow tracking of infectious diseases or similar. Furthermore, central analysis allows data mining to be used in order refine analysis processes, making this more accurate as more data is collected.

However, it will be appreciated that the distributed implementation is not essential, and additionally or alternatively, analysis could be performed in situ, for example, by having the monitoring device 920 and/or client device 930 perform steps 1425 to 1460 with resulting information being displayed locally, for example, using the client device 930 or a in-built display.

A further example of a microstructure arrangement and analysis technique will now be described with reference to FIGS. 15A to 15F.

In this example, a patch 1510 is provided, including a substrate 1511 having a number of microstructures 512 thereon. The form and configuration of the microstructures is not critical for the purpose of this example, and it will be appreciated that a range of different configurations could be used, as described above.

In this example, the substrate 1511 includes a substrate coil 1515, positioned on the substrate 1511, typically on a rear surface. The coil is operatively coupled to the one or more microstructure electrodes, which could be electrodes provided on microstructures, or conductive microstructures themselves. Typically the substrate coil includes two ends, with each end being coupled to different microstructure electrodes, as shown by the dotted lines, so that a signal in the substrate coil 1511 is applied between the microstructure electrodes. An excitation and receiving coil (not shown) is provided, typically in a housing of a measuring device, so that the excitation and receiving coil is aligned with and placed in proximity to the substrate coil when a measurement is to be performed, for example, when the housing is attached to the substrate. This is performed to inductively couple the excitation and receiving coil to the substrate coil, so that when an excitation signal is applied to the excitation and receiving coil by the signal generator, this induces a corresponding signal in the substrate coil 1515, which is then applied across the microstructure electrodes.

Figure 15A:
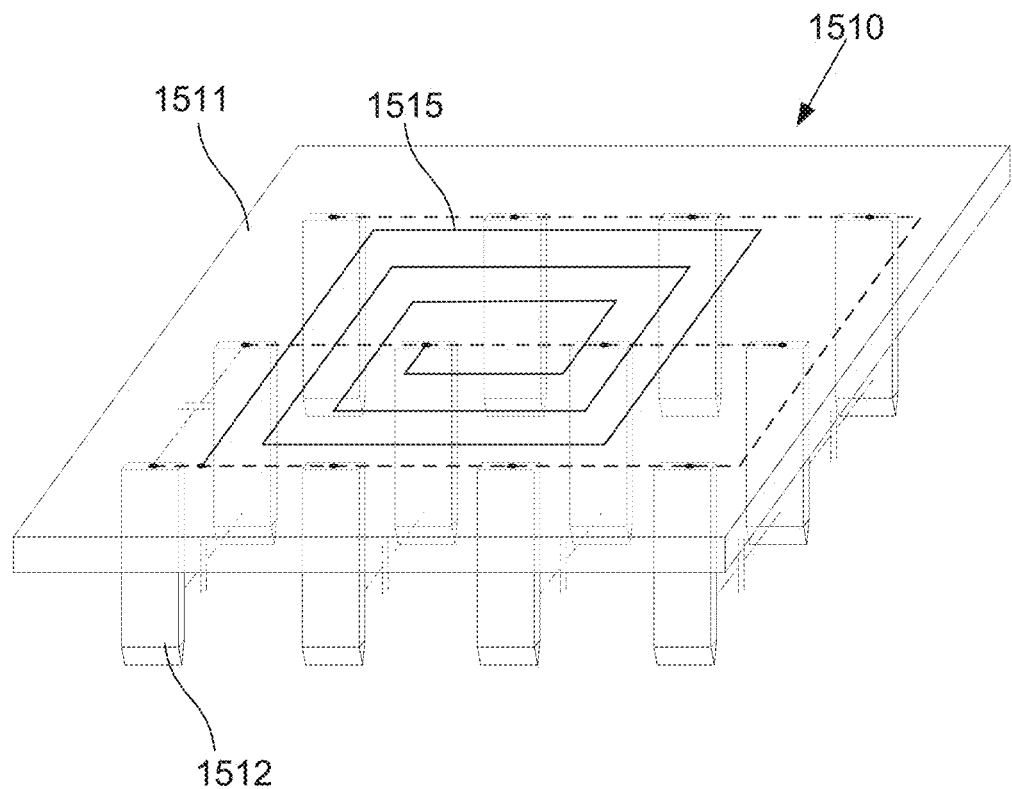
FIG. 15A is a schematic perspective topside view of an example of a patch including a substrate incorporating microstructure electrodes and a substrate coil.
Figure 15B:
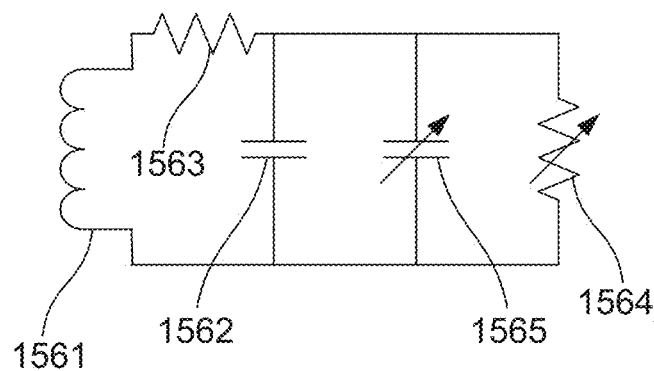
FIG. 15B is a schematic diagram of an equivalent circuit representing the electrical response of the patch of FIG. 15A.

The tissue and/or fluid surrounding the microstructure electrodes, and the electrodes, act as capacitors, as shown. As a result, the excitation and receiving coil and the substrate coil act as a tuned circuit, and an example circuit configuration is shown in FIG. 15B. This includes a fixed inductance 1561 and capacitance 1562 and resistance 1563, representing the inherent responsiveness of the excitation and substrate coils. The circuit also includes a variable capacitance and variable resistance 1565, 1564, representing the responsiveness of the microstructure electrodes, and the tissue or other materials between the electrodes. Thus, it will be appreciated that the frequency response and damping (Q) of the tuned circuit will vary depending on the values of the variable capacitance and resistance, which in turn depends on the environment within which the microstructure electrodes are present.

Figure 15C:
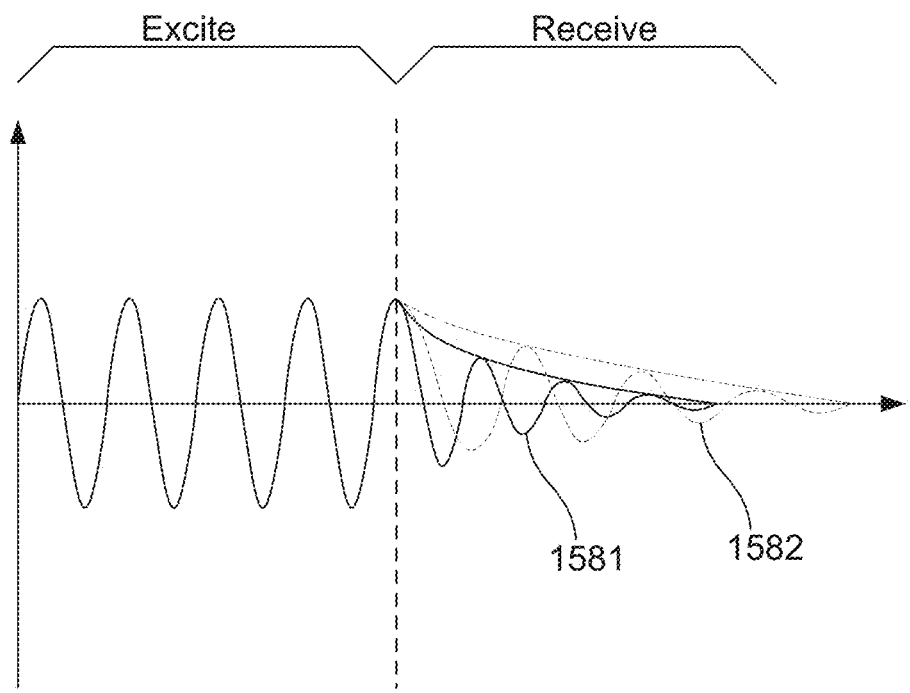
FIG. 15C is a graph illustrating the response to a drive signal for the patch of FIG. 15A.

In general, when a signal is applied to the excitation and receiving coil, the overall response will be a constant amplitude signal in the excitation and receiving coil, as shown in FIG. 15C. When the drive signal is halted, the circuit will continue to resonant, with the resulting signal decaying over time as shown to the right of the dotted line. The rate and/or frequency of the decay depends on the values of the variable capacitance and resistance, so different responses 1581, 1582 will arise depending on conditions within the subject, which in turn allows information regarding conditions within the subject to be derived. For example, this can be influenced by binding of analytes to the microstructure electrode, fluid levels, or the like, so examining changes in the decay rate and frequency can be used to derive information regarding the presence of analytes, fluid levels, or the like.

Figure 15D:
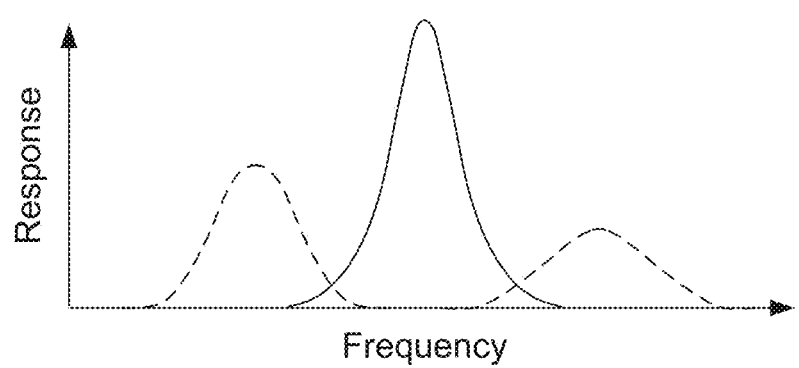
FIG. 15D is a graph illustrating the resonance response of the patch of FIG. 15A.
Figure 18A:
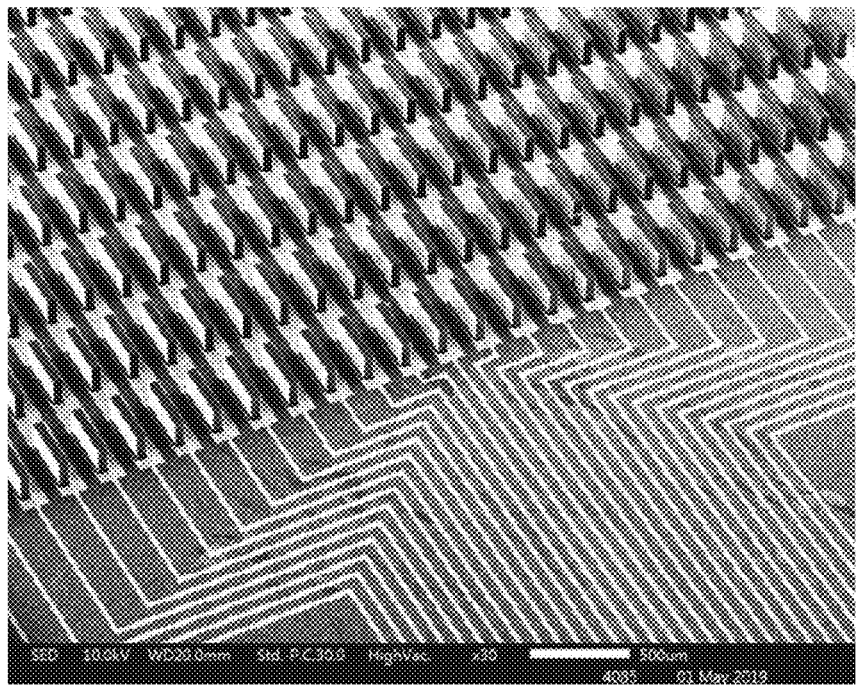
FIGS. 18A to 18D are micrograph images of examples of microstructures manufactured using the approach of FIGS. 17A to 17P.
Figure 18B:
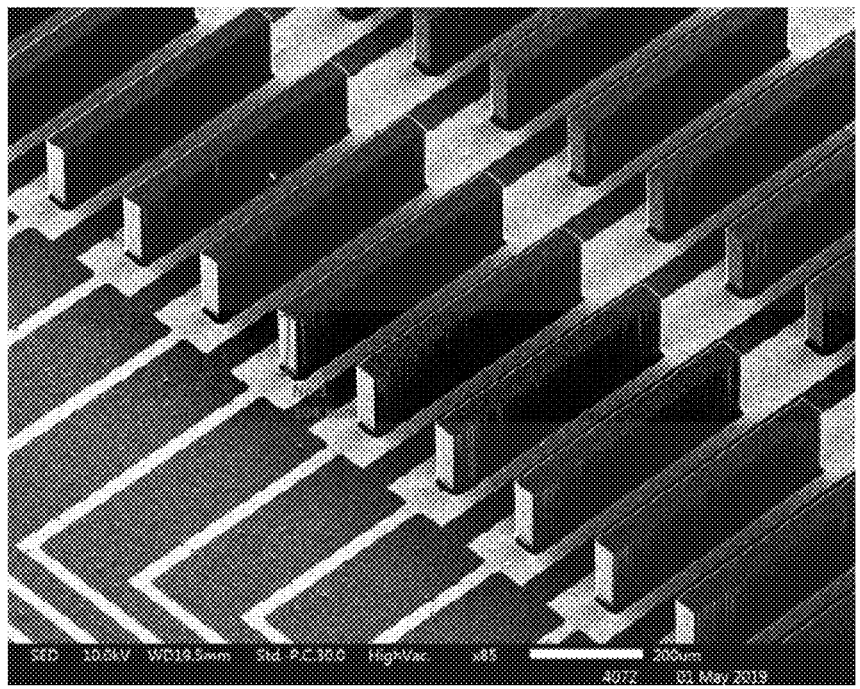
Figure 18C:
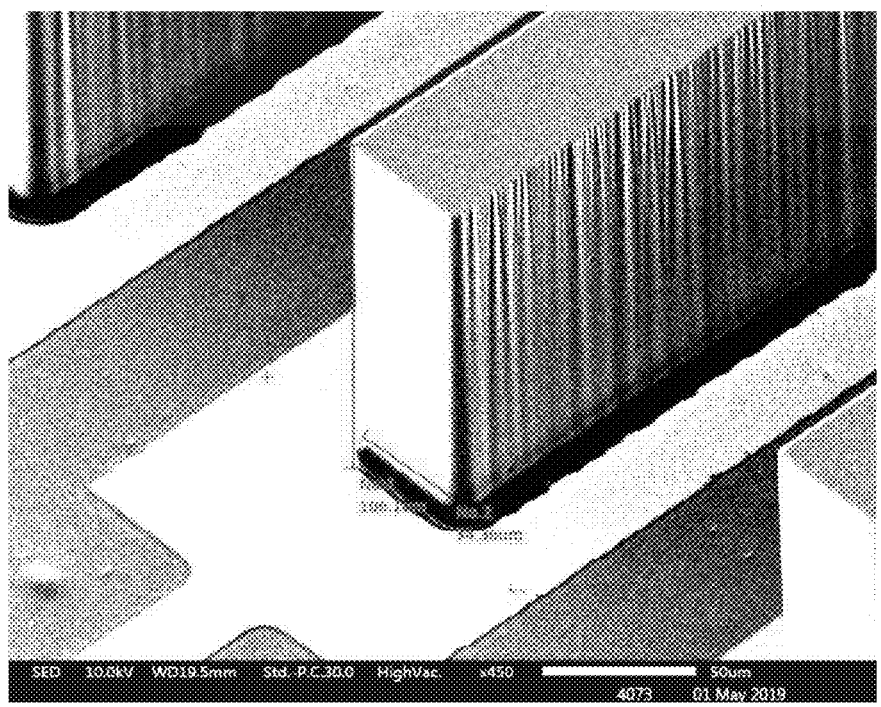
Figure 18D:
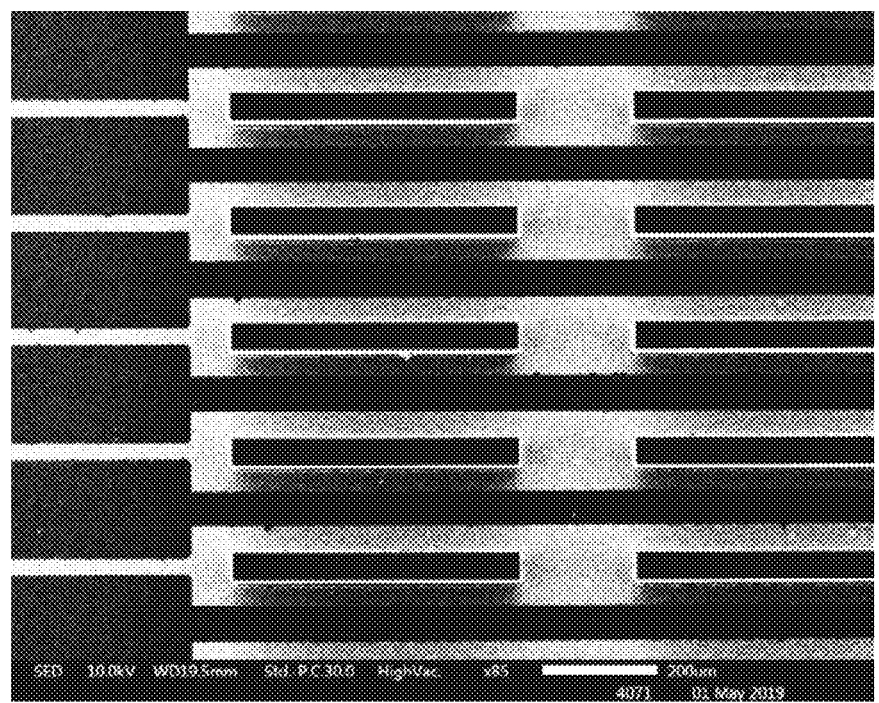

However, as decay signals are transient, in another example the circuit's response at different frequencies is analysed and used to determine the resonant frequency and Q factor of the tuned circuit, which are in turn indicative of the resistance and capacitance values. In this regard, a change in electrical conditions within the subject will result in a change in the frequency response, as shown in FIG. 15D. For example, a response in absence of analytes might be as shown in solid lines, whereas the presence of analytes might result in an increase or decrease in the resonant frequency and/or Q factor, as shown in dotted lines.

It will be appreciated that this technique employs a patch with no electronically active sensing elements, whilst allowing measurements to be made regarding conditions within the subject, such as the presence or concentration of analytes to be easily determined. It will also be appreciated that suitably adapting the coating allows a range of different analytes to be sensed and that this can also be adapted for performing other suitable measurements.

Further details exemplifying the above described arrangements will now be described.

Manufacture

Example process for manufacturing a substrate including microstructures will now be described in more detail.

In a first example, shown in FIGS. 17A to 17P, microstructures are made from an insulating polymer applied to a substrate, with electrodes patterned on the substrate through selective etching to act acting as electrical connections for the polymer microstructures. It will be also be appreciated that conductive polymers could be used, for example through suitable doping of an insulating polymer.

In this example, a first step shown in FIGS. 17A to 17G is to selectively pattern an electrode architecture onto a flexible polyethylene terephthalate (PET) substrate 1701. An electrode design, upon which microstructures were to be defined, was patterned on the PET; in this case Indium Tin Oxide (ITO) 1702 layer deposited atop flexible PET substrate, and the electrode pattern selectively etched from the ITO layer. The substrate was prepared (FIG. 17A), before a positive photoresist, AZ1518 (MicroChemicals), was patterned on top of the ITO via photolithography (FIG. 17B), and soft baked (FIG. 17C). The photoresist is selectively exposed to UV (FIG. 17D) to define an electrode pattern, before the photoresist is baked and developed using a developer AZ 726MIF (MicroChemicals) (FIG. 17E) and the exposed ITO regions wet acid etched (FIG. 17F). The photoresist was removed to reveal the final etched ITO pattern that provides the conductive electrodes for the device (FIG. 17G).

In a second step, shown in FIGS. 17H to 17P, 3D microstructures were fabricated from photosensitive polymers onto the ITO electrodes. The patterned PET substrate with ITO electrodes was treated with an oxygen plasma (FIG. 17H), to improve wetting and resist adhesion, and a seed adhesion layer of SU-8 3005 (MicroChemicals) 1704 was spin-coated on to the ITO-PET substrate (FIG. 17I). After baking of the seed SU-8 layer lamination (FIG. 17J) an SUEX SU-8 film resist 1705 (DJ MicroLaminates) was bonded to the substrate (FIG. 17K) through thermal lamination. After alignment and exposure to UV through a mask aligner (FIG. 17L), the exposed SU-8 areas crosslinked to form rows of rectangular microstructures 1706 with vertical wall profile along the conductive ITO fingers 1702 (FIG. 17M). The structures are baked, with the SU-8 1704 and SUEX 1705 before being developed in PGMEA (Propylene glycol monomethyl ether acetate) (Sigma Aldrich), and then hard baked (FIG. 17N). A shadow mask 1708 is applied to the substrate 1701 with the microstructures 1706 being coated with gold 1707 (FIG. 17O) through selective deposition, before the mask is removed (FIG. 17P), leaving selectively metallized microstructures that act as electrodes.

In this example the microstructures have flat tips, but it will be appreciated that other UV lithography techniques such as greyscale lithography, backside diffraction lithography, 2 photon lithography etc. could be employed to define tapered microstructures.

Resulting microstructures are shown in FIGS. 18A to 18D.

In a second example, shown in FIGS. 19A to 19L, microstructures are made by molding.

Figure 19A:
Figure 19B:
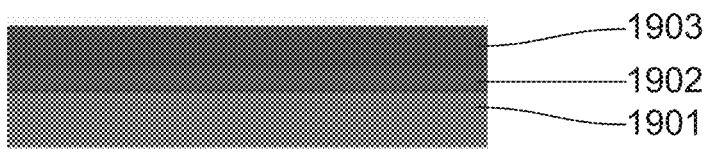
Figure 19C:
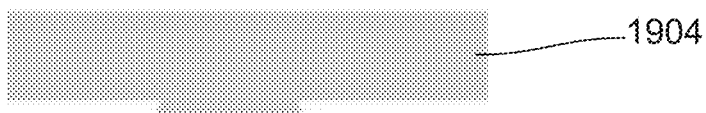
Figure 19D:
Figure 19E:
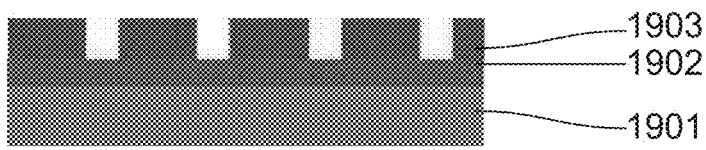
Figure 19F:
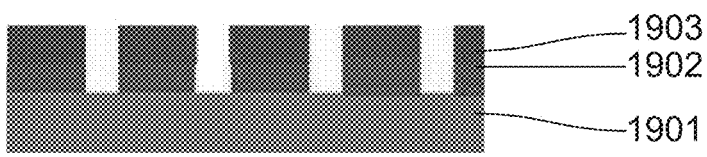
Figure 19G:
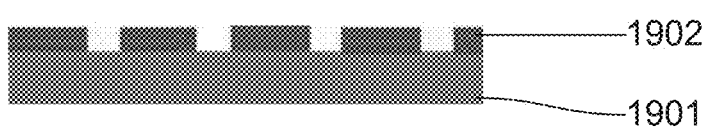

In this example, a silicon wafer 1901 was deposited with a 90 nm layer 1902 of Nitride (FIG. 19A). AZ1505 (MicroChemicals) positive resist 1903 was then spun on at 4000 rpm (FIG. 19B). Rectangular pattern to define the blade outline was directly written using a mask writer 1904 (FIG. 19C). The written pattern was developed using AZ 726 MIF (MicroChemicals) for 30 secs (FIG. 19D). Reactive ion etching is used to remove the nitride layer 1902 (FIG. 19F), before the photoresist 1913 is removed (FIG. 1919E). The wafer is then held vertically in a bath of Potassium Hydroxide at 80° C. for 40 mins, to etch the silicon wafer along the crystal axis of the wafer (FIG. 19G). The etching stops at the axis 111 thus defining the sharp tips needed, this then acts as a mold for the devices that are fabricated.

Omni-Coat is used as a lift off resist and is coated onto the wafer to a thickness of about 20 nm, using a spin recipe of 3000 RPM for 1 min and then baking at 200° C. for 1 min. Following this a 5 micron layer 1905 of SU8 3005 is spun on to the wafer at 3000 RPM following by baking at 65° C. for 1 min, then at 95° C. for 20 secs followed by 65° C. again for 1 min (FIG. 19H). The thinner formulation of the SU8 3005 would allow it to flow more easily into the sharp triangular crevices etched into the silicon wafer mold. A layer 2016 of SU8 1900 is then spun on top of this layer to a thickness of 200 microns using a spin recipe of 2000 RPM for 60 secs (FIG. 19I). Following this the wafer was baked at 65° C. for 5 mins, then at 95° C. for 35 mins and then again at 65° C. for 5 mins. This layer of SU8 1900 would allow the sharp tips to stand on a solid layer.

Finally the wafer is flood exposed using an Ultra Violet source 1907 delivering 15 mW/cm$^2$ of Power for 40 secs (FIG. 19J). The structures are released by soaking the wafer in an AZ 726 developer solution overnight (FIG. 19K) and exposed the wafer to a thermal shock of 120° C. for 15 secs. The structures are removed from the mold flipped and dried using Nitrogen gas (FIG. 19L).

Figure 20A:
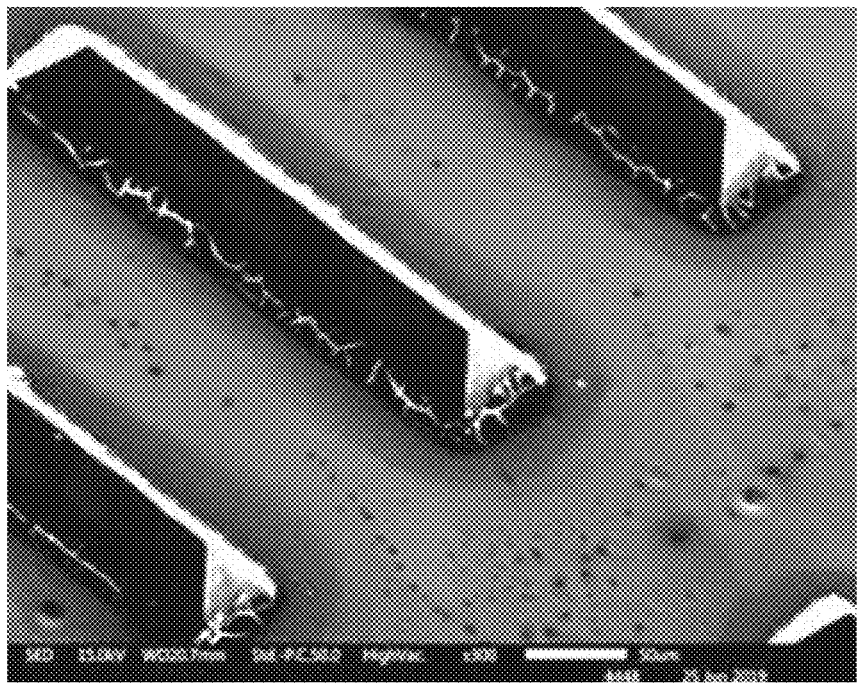
FIGS. 20A and 20B are micrograph images of examples of microstructures manufactured using the approach of FIGS. 19A to 19L.
Figure 20B:
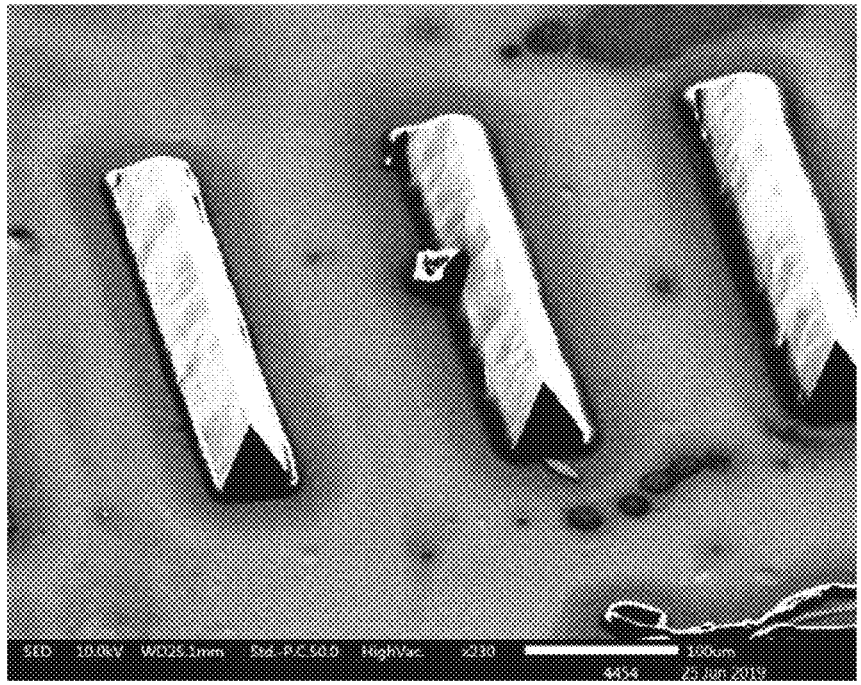
Figure 20C:
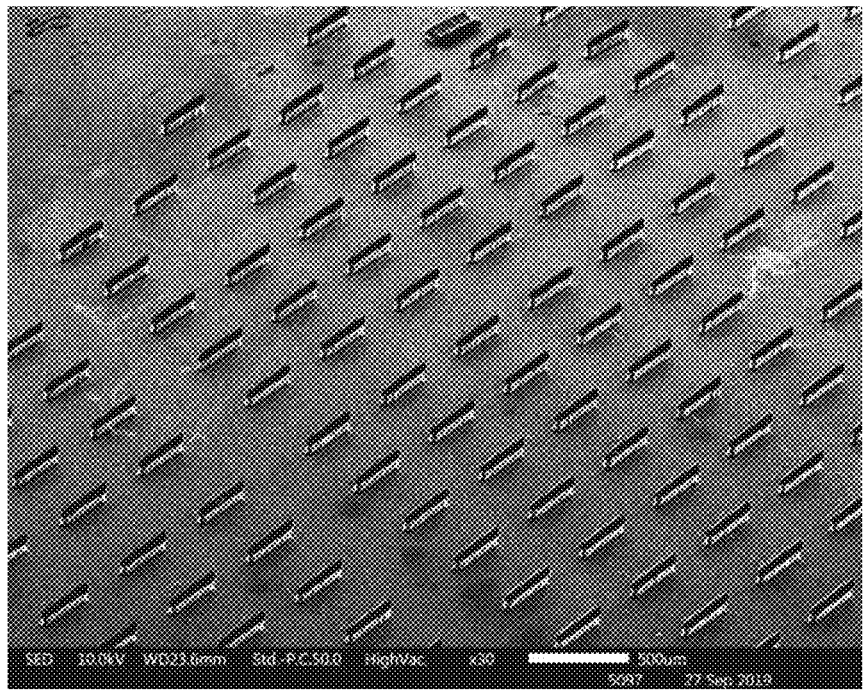
FIGS. 20C and 20D are micrograph images of further examples of microstructures manufactured using the approach of FIGS. 19A to 19L.
Figure 20D:
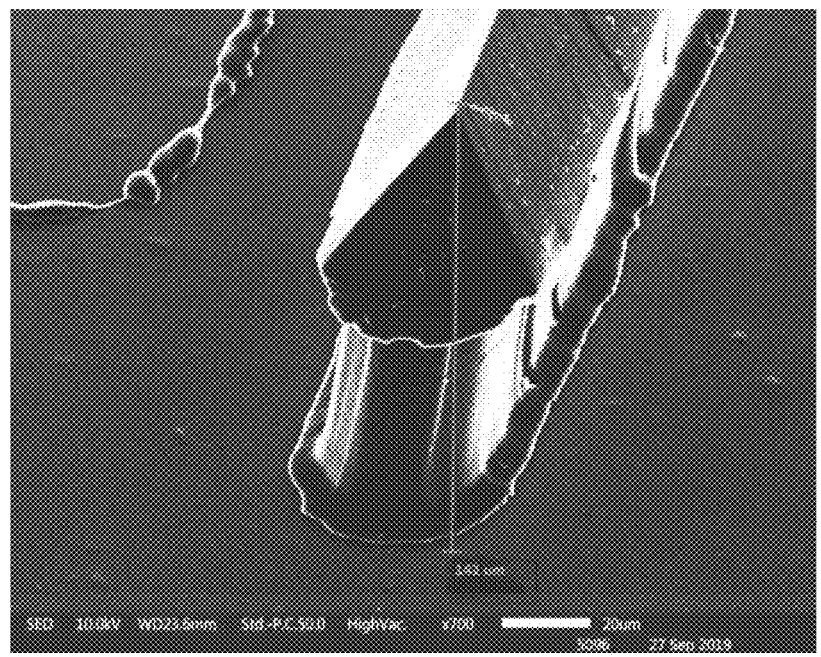

Resulting microstructures are shown in FIGS. 20A and 20B.

Figure 21A:
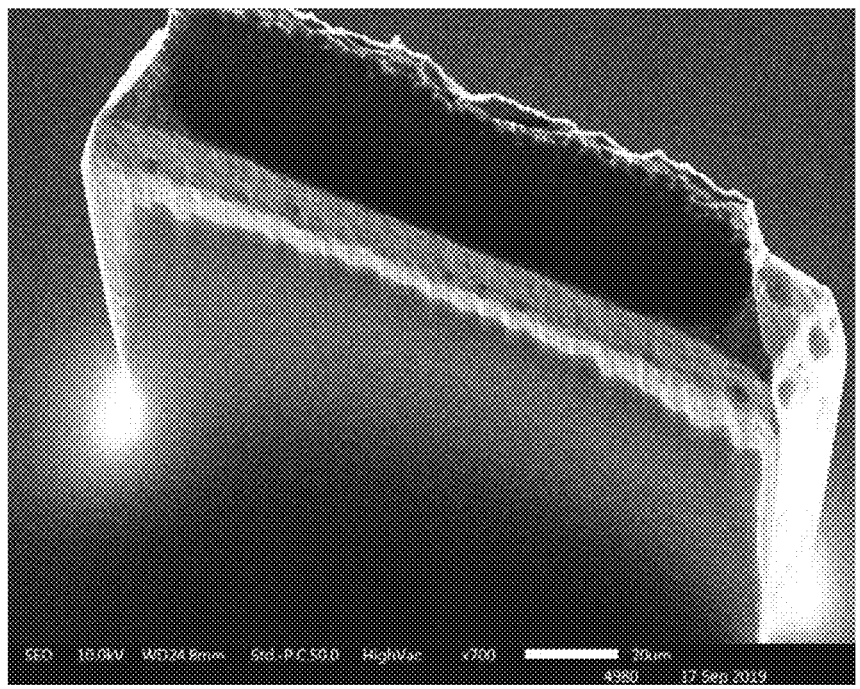
FIGS. 21A and 21B are micrograph images of examples of partially coated microstructures.
Figure 21B:
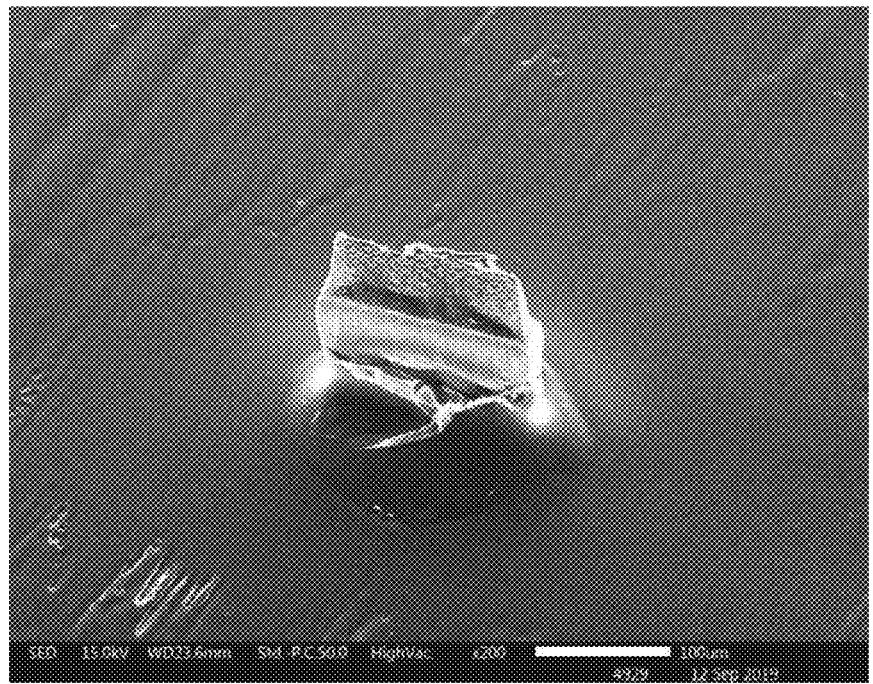

FIGS. 21A and 21B show silicon blades fabricated via etching. FIG. 21A shows the blade coated with a nearly 1 micron thick layer of SU8 3005 which has been diluted in a ratio of 3:2 using SU8 thinner and spun at 5000 RPM for 40 secs. FIG. 21B gives a depiction of the blade selectively coated at its base with the polymer coating. While the tip of the blade is bare and available for detection purposes only at this area. This selective coating is achieved by pressing and removing the coated blade in FIG. 21A into a thin layer of Aluminium foil which mechanically removes the resist from the tip of the blade. This allows the blade to be partially covered with an insulative coating, so that only the tip portion acts as an electrode, thereby allowing measurements to be performed in the epidermis and/or dermis, as described above with respect to FIGS. 5L and 5M.

Hydration

An example of use of the microstructures in measuring hydration will now be described.

In this regard studies have suggested that there is a strong correlation between level of performance and hypohydration measured as % Δ in body mass, with significant hypohydration occurring when body mass loss is >2%. Evidence suggests that hypohydration detrimentally effects high-intensity muscular endurance, strength and power. Furthermore, there is a relationship between decrease in muscular strength and power and the likelihood of injury occurrence, which suggests that the ability to accurately measure hydration could be valuable for athletes, particularly in high risk sports.

An experiment was performed to measure pig skin hydration using a microstructure impedance based approach. In this example, tissue was measured at a nominal 'fresh' hydration point and dehydrated by application to a warming plate with a set point of 38° C. Tissue block volume was measured by a displacement method at the commencement, and end of the experiment. It was assumed that all mass change was due to water loss due to evaporation from the excised tissue.

Figure 22A:
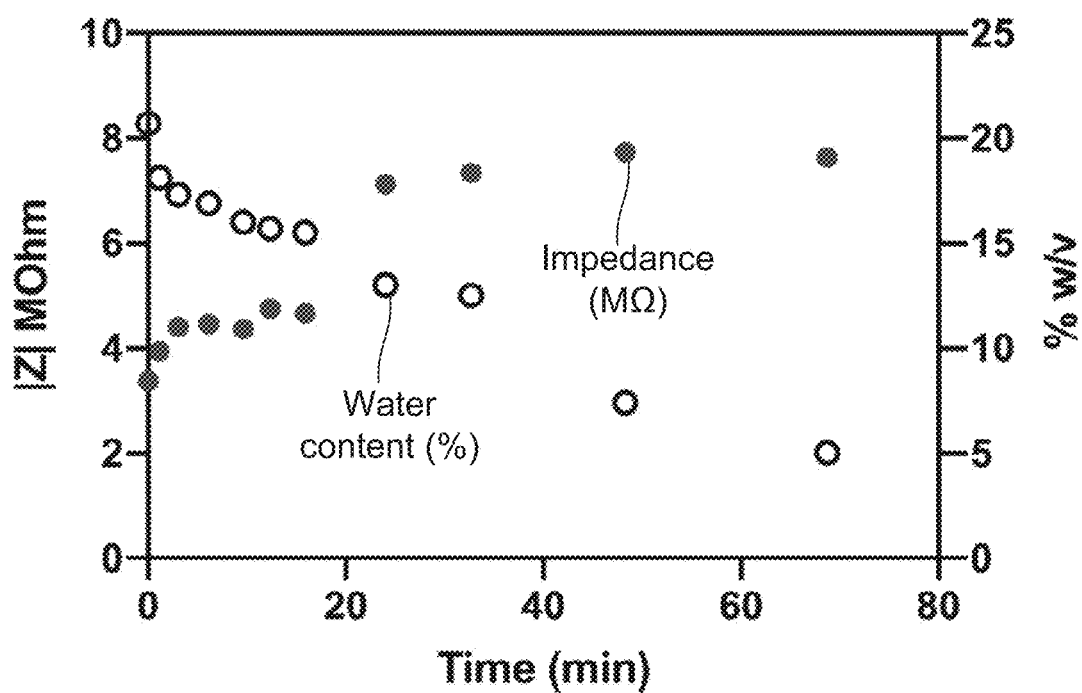
FIG. 22A is a graph illustrating an example of changes in epidermal impedance versus changing hydration in pig skin.

Time-series data of impedance measured at 200 Hz is shown in FIG. 22A, with the second axis representing concurrent water content estimates derived from measured mass and volume measures. The inverse relationship between impedance and water content is as expected and the first-order water loss rate is mirrored in the impedance changes measured.

This demonstrates a microstructure patch can successfully engage and allow measurement of the specimen water loss to a satisfactory level of precision. This architecture is thereby a firm basis for development of the electrically interfacing microstructure patch as demonstrated in hydration sensing.

A human water loss and rehydration experiment was conducted to examine the ability of the above described arrangements, to assess body water loss (and gain) through interrogation of the interstitial fluid in the viable epidermis layers of the human anterior forearm. A 4×4 mm gold-coated patch was applied and multi-frequency impedance measures were made with bench instrument (Keysight E4990A). The 4×4 mm device was electrically divided into two 2×4 mm regions with 15 blade microstructure electrodes of 150 μm depth and 260 µm wide, which are expected to have penetrated to around 80 µm deep into the human tissue an in in vivo experiment.

Dehydration was controlled over a three-hour period and a reference or 'ground truth' measure of plasma water loss was performed by serial haematocrit (Hct) measures. Normal red cell mass accounts for approximately 43% of the plasma volume at normal hydration levels in the adult male. Increases in the Hct in the absence of blood loss are therefore due to water loss.

Figure 22B:
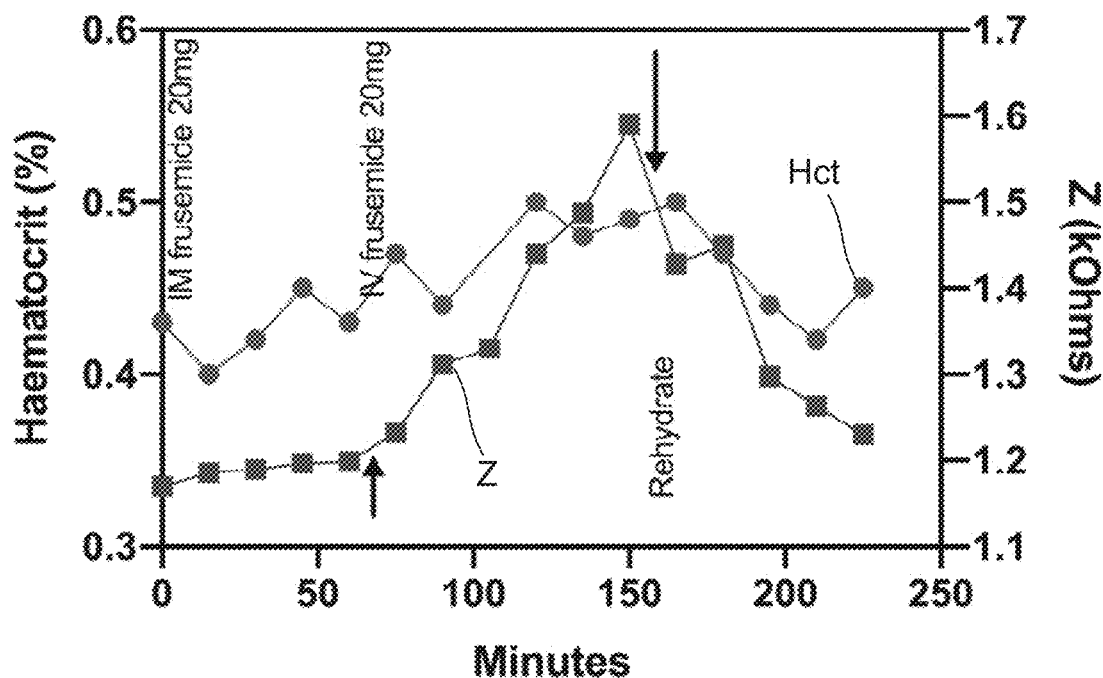
FIG. 22B is a graph illustrating an example of changes in epidermal impedance and Hematocrit versus changing in hydration; and, FIG. 22C is a graph illustrating an example of changes in epidermal and skin impedance versus changing in hydration.

FIG. 22B is a graph showing resulting measured impedance (Z) and haematocrit (Hct) vs. time as total body water loss approaches 1.7%. Impedance trend follows dehydration as measured by Hct and follows restoration with a response time of minutes.

Recording Hct and impedance of the viable epidermis over time shows good association with dehydration. At the rehydration point the measure also follows the restoration of total body water levels. Body weight and urine analysis were used to quantify total body water loss and gain over the study period.

Notably at a total body water loss of less than 1.7%, electrical correlates were able to be detected. This level is below the threshold of detection of dehydration by trained clinicians and would conventionally require plasma osmolarity measures by blood sampling and laboratory assay. Restoration of body water was rapid and the sensor was able to detect this change in the ISF in less than 15 minutes.

The two-electrode measurement and range of impedance changes seen on a bench instrument is easily miniaturized into a wearable device and the minimally invasive nature of the sensor resulted in only extremely mild local erythema post removal of the device.

It is also notable that total body water loss induces physiological responses which may be categorized depending on the resultant osmolarity of plasma. For example, loss of water through sweat and restriction of oral fluids results predominantly in hypertonic hypovolaemia i.e. reduced plasma volume with disproportionately higher salt ($Na^+$, $Cl^-$, $K^+$) concentration. By contrast, water loss induced by diuretics, vomiting, cold and altitude induces isotonic or hypotonic hypovolaemia. Plasma osmolarity is reduced due to the disproportionate loss of salt with respect to water. Conductivity of interstitial fluid (ISF) is intimately related to the concentration of conductive ions, and therefore these different modes of hydration change can be discerned based on changes in impedance.

Figure 22C:
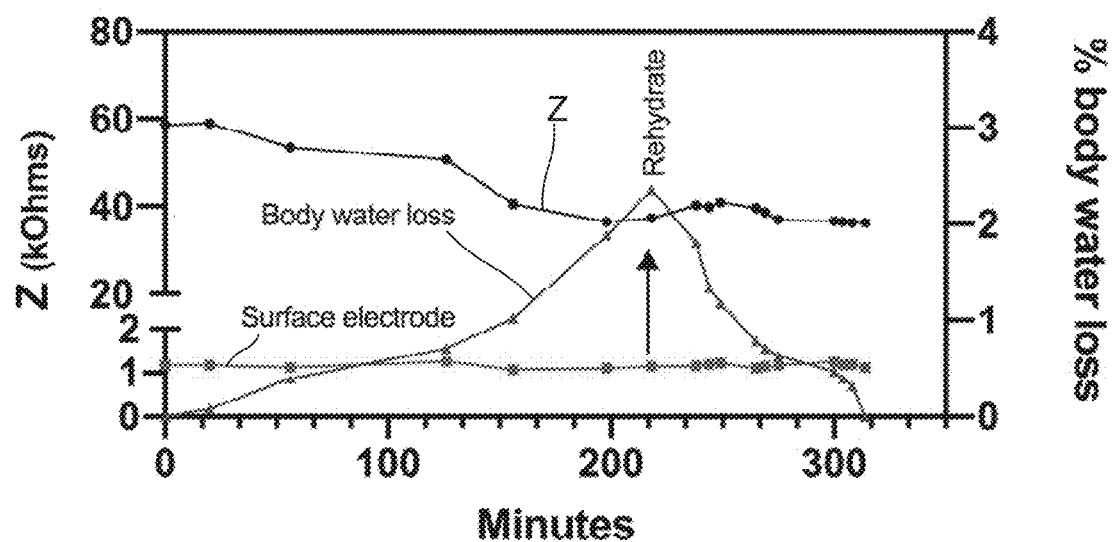

An example of this is shown in FIG. 22C, which illustrates changes in impedance as a result of exercise induced water loss, which causes a hypertonic response whereby conductivity is increased (impedance declines). This is contrasted to the results in FIG. 22B of diuretic induced hypovolaemia shows an increase in impedance consistent with a loss of ions disproportionate to the water excreted through the kidneys.

It will therefore be appreciated that not only can changes in impedance be indicative of hydration changes, but that additionally monitoring a direction of impedance change can be used to indicate the nature of the water loss, and specifically, whether this is hypertonic or isotonic, with the magnitude of any change reflecting the amount of fluid lost. Similarly, if a hydration level is maintained or approximately constant then a change in impedance is indicative of a change in ion concentrations Erythema Studies have been performed to evaluate the tolerability and functionality of microstructure patches in humans.

Figure 23A:
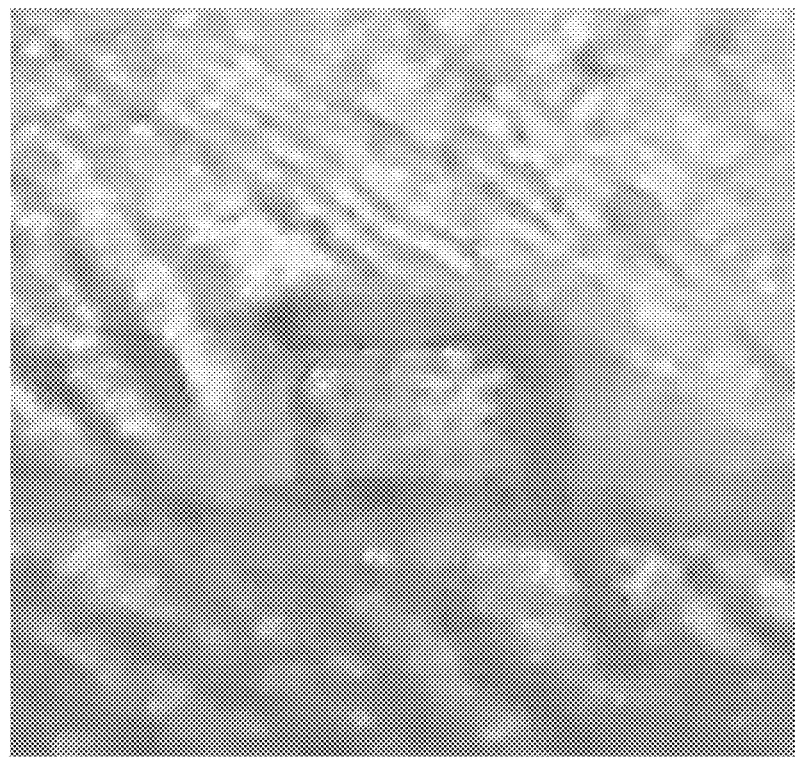
FIG. 23A is an image of a microstructure patch application site on a human forearm skin immediately post-removal.

In one example, a qualitative tolerability assessment was performed following microstructure patches application which noted a very mild local response at the application site immediately post-removal. This was characterized by slight indentation with no overt erythema or oedema, which was resolved within 15 minutes of removal. This is shown in FIG. 23A. This shows the indentation was most prominent around the edges and corners of the microstructure patch, with very mild redness at these locations, and with no redness associated with the microstructures themselves.

Figure 23B:
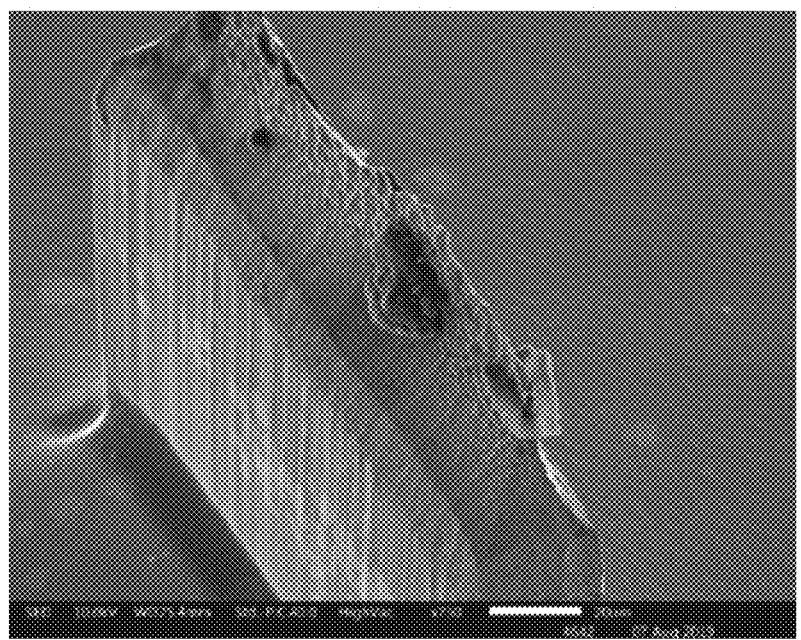
FIG. 23B is a Scanning Electron Micrograph of a microstructure after application to human skin.

Scanning Electron Microscopy (SEM) was performed to confirm that the microstructures had, in fact, penetrated the skin, showing cellular debris remaining on the removed microstructures, as shown in FIG. 23B, confirming successful microstructure penetration despite the absence of overt erythema.

To investigate this observation further, we two dedicated erythema studies were performed with multiple subjects. These studies investigated the local skin response to microstructure patch application to the skin of the anterior forearm over a time period of 2 hours. Microstructure patches were applied using a guided load cell mechanism, at a force of either 5N remaining in place for 30 minutes (Study 1) or 3N and remaining in place for 10 minutes (Study 2).

The first human erythema study was on five volunteers. In some cases, hair was removed from the skin using depilatory cream and a paper mask was fixed to the application area to avoid any effect due to sensitivity to surgical adhesives in tapes. Three separate non-functionalised microstructure patches were applied to skin exposed by windows in the paper mask, and a fourth window was untreated and used as a control for comparison.

Observations were made for local erythema and a scoring rubric was used as given in Table 4 below.

TABLE 4

| eScore | Observation |
| --- | --- |
| 0 | No discernable difference relative to control |
| 1 | Very mild redness |
| 2 | Mild redness |
| 3 | Red region extending beyond 4 $mm^2$ application area |
| 4 | Extensive redness and/or capillary rupture |
| 5 | Frank blood and/or oedema superficially |

Figure 24A:
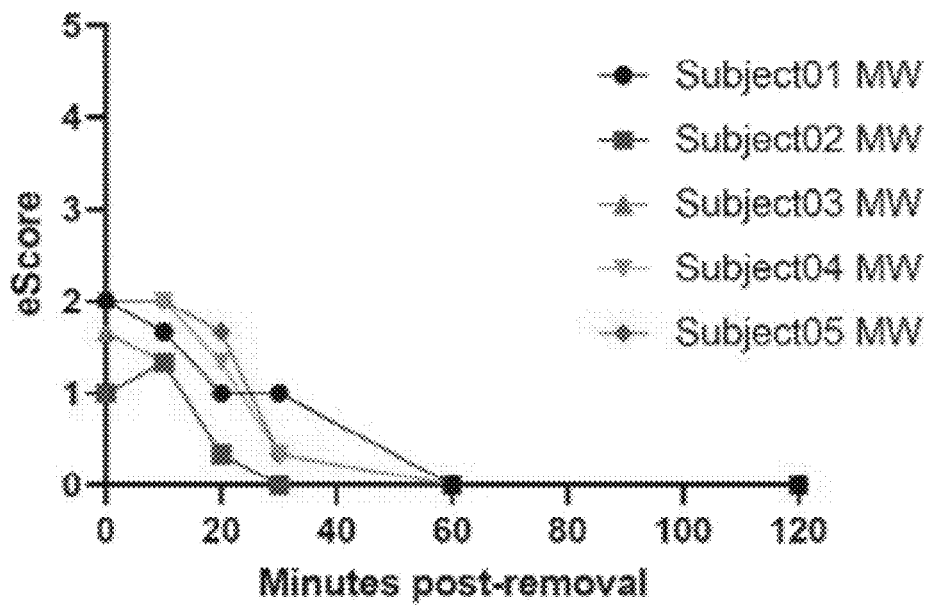
FIG. 24A is a graph of example qualitative scores of erythema at microstructure patch application sites on human forearm skin from a first study.

Results from the first study are shown in FIG. 24A, which shows the eScores for Subjects 01-05 in this study, which were independently assessed at 10, 20, 30, 60 and 120 minutes post-application. Data points represent the average eScore from three Microwearables per subject per timepoint.

Results show that all volunteers experienced some mild or very mild erythema at the site of Microwearable application as observed immediately after removal, which quickly resolved within 60 minutes. No erythema was noted after this time point. Similar to the earlier single subject observation, the indentation/redness was localised around the edges of the Microwearable, with little or no effect seem from the microstructures themselves.

Figure 24B:
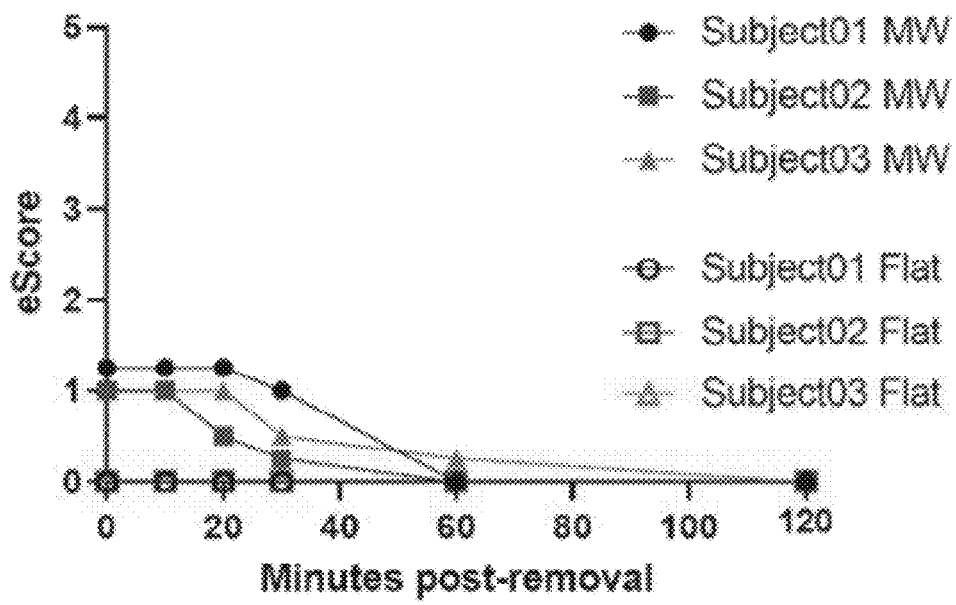
FIG. 24B is a graph of example qualitative scores of erythema at microstructure patch application sites on human forearm skin from a second study.

The second erythema study was performed on three volunteers. Two Microwearable devices were applied at 3N and were removed after 10 minutes of wearing. To investigate further the 'edge effect' observed in a first-in-human trial and in Study 1, a flat patch (i.e. without microstructures) was applied on the third skin site, for comparison. The fourth window remained untreated as a control. Results are shown in FIG. 24B, which shows the eScore observations (data points are an average of 2 separate observations per subject per time point) over 120 minutes post-removal.

Results are similar to Study 1 in that no subject experienced erythema more extensive than 'mild redness' at the site immediately prior to removal of the Microwearable. This mild erythema resolved quickly within 60 minutes, with one subject with a score of 0.5 at 60 minutes, which subsequently resolved completely by 120 minutes. No erythema was observed following application of flat patches, which may suggest that the very mild/mild erythema observed following microstructure patch application is associated with skin barrier penetration (i.e. by the presence of microstructures).

Microstructure patch eScores were, in general, lower in Study 2 than Study 1, suggesting that lowering the application force of application reduces the extent of the mild erythema that occurs. As the erythema was observed immediately after the microstructure patches were removed and did not increase over time, it appears erythema is caused by the application event itself—driven by the corners and edges of the microstructure patches—and is not exacerbated by continuous wearing. Future-generation microstructure patch can use different edges and corner configurations leading to negligible erythema.

As no local erythema was observed within the area covered by microstructures, SEM was performed to confirm that the structures had successfully penetrated the skin of the subjects in Study 1. Example images of individual or row of microstructures after application to two subjects are shown in FIG. 25, including images of individual microstructures prior to application to the skin (FIGS. 25A and 25D) and images post application (FIGS. 25B, 25C and 25E, 25F).

Images from all subjects confirmed successful penetration of the skin, from the presence of biological material located on the upper portion of the microstructures (FIGS. 25B and 25E), with arrows indicating examples of cellular debris extracted by the microstructures on removal.

FIGS. 25C and 25F show rows of microstructures, and exhibit areas with dried interstitial fluid as indicated by the arrows. These observations confirm that the microstructures have successfully breached the outermost stratum corneum layer of the skin and are able to access cellular environments beneath to gain access to the interstitial fluid, which is the source of bio-signals including biomarkers of disease.

It is therefore apparent that microstructure patches are at worst only associated with very mild/mild erythema at the site of application. This mild local response is transient, and is completely resolved within 60-120 mins post-application. Any redness immediately occurs after application, and is not associated with continuous wearing of the microstructure patch.

Any erythema is focused around the edges and corners of the microstructure patch, with little/no erythema noted in the area covered by microstructures, but the observation that a flat patch had no effect suggests that the erythema after microstructure patch application is associated with a physical breach of the skin barrier.

Despite the observation that microstructures did not cause overt erythema, it was we confirmed that microstructure penetration was successful, with visible breaching of the stratum corneum and with confirmed access to skin compartments rich in interstitial fluid.

Use of the System

In one example, the above described system allows fluid measurements, such as ion concentration and/or hydration measurements to be performed. The length of the structures can be controlled during manufacture to enable targeting of specific layers in the target tissue. In one example, this is performed to target fluid levels in the epidermal and/or dermal ISF.

The patches can therefore provide a measurement device which avoids the need to be perform surface based measurements, allowing measurements to be performed that are more accurate and/or sensitive.

The system can provide simple, semi-continuous or continuous monitoring: a low cost-device micro wearable would be applied to the skin and potentially be worn for days (or longer), and then simply replaced by another micro wearable component. Thus, micro wearables provide a route for monitoring over time—which can be particularly important in circumstances where fluid levels are changing rapidly.

In one example, the above described approach can allow wearables to provide widespread, low-cost healthcare monitoring for a multitude of health conditions that cannot be assayed by current devices, which are placed on the skin.

The above described patches may also be used to test other forms of subjects, such as food stuffs, or the like. In this example, the patch could be used to test for the presence of unwanted contaminants, such as pathogens, such as bacteria, exotoxins, mycotoxins, viruses, parasites, or the like, as well as natural toxins. Additionally contaminants could include agrochemicals, environmental contaminants, pesticides, carcinogens, or the like. bacteria, or the like.

Accordingly, it will be appreciated that the term subject can include living subjects, such as humans, animals, or plants, as well as non-living materials, such as foodstuffs, packaging, or the like.

Accordingly, the above described arrangement provides a wearable monitoring device that uses microstructures that breach a barrier, such as penetrating into the stratum corneum in order to perform measurements on a subject. The measurements can be of any appropriate form, and can include measuring the fluid levels within the subject, and in particular a subject measuring electrical signals within the subject, or the like. Measurements can then be analysed and used to generate an indicator indicative of a health status of the subject.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A system for performing fluid level measurements on a biological subject, the system including:
    a) at least one substrate including a plurality of microstructures configured to breach a stratum corneum of the biological subject, at least some microstructures including an electrode and wherein the microstructures are conductive and include an insulating layer extending over an end of the microstructure proximate the substrate so that at least a tip portion of the microstructure is uncoated and acts as the electrode, and wherein at least some of the microstructures include a shoulder that is configured to abut against the stratum corneum to control a depth of penetration;
    b) a signal generator operatively connected to at least one microstructure pair to apply an electrical stimulatory signal between microstructures in the at least one microstructure pair, wherein microstructures in the at least one microstructure pair each have respective electrodes in opposition from one microstructure and another microstructure, and wherein the electrical stimulatory signal generates an electric field between the respective electrodes;
c) at least one sensor operatively connected to the at least one microstructure pair, the at least one sensor being configured to measure electrical response signals between microstructures in the pair; and,
d) one or more electronic processing devices that are configured to:
i) determine measured electrical response signals, the response signals being at least partially indicative of a bioimpedance; and,
ii) perform an analysis at least in part using the measured electrical response signals to determine at least one indicator at least partially indicative of fluid levels in the subject and wherein the system is configured to perform repeated measurements over a time period so that changes in impedance are used to track changes in fluid levels over time.

2. A system according to claim 1, wherein at least one of:
a) at least some pairs of microstructures are angularly offset;
b) at least some pairs of microstructures are orthogonally arranged;
c) adjacent pairs of microstructures are orthogonally arranged;
d) pairs of microstructures are arranged in rows, and the pairs of microstructures in one row are angularly offset relative to pairs of microstructures in other rows;
e) pairs of microstructures are arranged in rows, and the pairs of microstructures in one row are orthogonally arranged relative to pairs of microstructures in other rows.

3. A system according to claim 1, wherein:
a) a spacing between the plurality of microstructures is at least one of:
i) less than 1 mm;
ii) about 0.5 mm;
iii) about 0.2 mm;
iv) about 0.1 mm; and,
v) more than 10 μm; and,
b) a spacing between pairs of microstructures is at least one of:
i) less than 1 mm;
ii) about 0.5 mm; and,
iii) more than 0.2 mm.

4. A system according to claim 1, wherein at least some of the plurality of microstructures at least one of:
a) are at least partially tapered and have a rounded rectangular cross sectional shape;
b) have a length that is at least one of:
i) less than 300 μm;
ii) about 150 μm;
iii) greater than 100 μm; and,
iv) greater than 50 μm;
c) have a maximum width that is at least one of:
i) about the same order of magnitude to the length;
ii) greater than the length;
iii) about the same as the length;
iv) less than 300 μm;
v) about 150 μm; and,
vi) greater than 50 μm; and,
d) have a thickness that is at least one of:
i) less than the width;
ii) of a smaller order of magnitude to the length;
iii) less than 50 μm;
iv) about 25 μm;
v) greater than 10 μm.

5. A system according to claim 1, wherein at least some of the plurality of microstructures have a tip that at least one of:
a) has a length that is at least one of:
i) less than 50% of a length of the microstructure;
ii) at least 10% of a length of the microstructure; and,
iii) about 30% of a length of the microstructure; and,
b) has a radius of at least one of:
i) at least 0.1 μm;
ii) less than 5 μm; and,
iii) about 1 μm.

6. A system according to claim 1, wherein at least some of the plurality of microstructures include at least one of:
a) a shaft extending from a shoulder to the tip, the shaft being configured to control a position of the tip in the subject; and,
b) anchor microstructures used to anchor the substrate to the subject.

7. A system according to claim 1, wherein the microstructures have a density that is at least one of:
a) less than 5000 per $cm^2$;
b) greater than 100 per $cm^2$; and,
c) about 600 per $cm^2$.

8. A system according to claim 1, wherein the substrate includes electrical connections to allow electrical signals to be applied to and/or received from respective microstructures which are connected to the electrical connections.

9. A system according to claim 1, wherein the system includes one or more switches for selectively connecting at least one of the at least one sensor and at least one signal generator to one or more of the plurality of microstructures and wherein the one or more processing devices are configured to control the switches and the signal generator to allow at least one measurement to be performed.

10. A system according to claim 1, wherein system includes:
a) a substrate coil positioned on the substrate and operatively coupled to one or more planar electrodes; and,
b) an excitation and receiving coil positioned in proximity to the substrate coil such that alteration of a drive signal applied to the excitation and receiving coil acts as a response signal.

11. A system according to claim 1, the insulating layer extending over at least one of:
a) at least half of a length of the microstructure;
b) about 90 μm of a proximal end of the microstructure; and,
c) at least part of a tip portion of the microstructure.

12. A system according to claim 1, wherein at least one planar electrode has at least one of:
a) has a surface area of at least one of:
i) less than 200,000 $μm^2$;
ii) about 22,500 $μm^2$;
iii) at least 2,000 $μm^2$;
b) extends over a length of a distal portion of the microstructure;
c) extends over a length of a portion of the microstructure spaced from the tip;
d) is positioned proximate a distal end of the microstructure;
e) is positioned proximate a tip of the microstructure;
f) extends over at least 25% of a length of the microstructure;
g) extends over less than 50% of a length of the microstructure;
h) extends over about 60 μm of the microstructure; and,
i) is configured to be positioned in a viable epidermis of the subject in use.

13. A system according to claim 1, wherein the microstructures include a material including at least one of:
   a) a material to reduce biofouling;
   b) a material to attract at least one substance to the microstructures; and,
   c) a material to repel at least one substance from the microstructures.

14. A system according to claim 1, wherein at least some of the plurality of microstructures are coated with a coating and wherein the coating at least one of:
   a) modifies surface properties to at least one of:
      i) increase hydrophilicity;
      ii) increase hydrophobicity; and,
      iii) minimize biofouling;
   b) attracts at least one substance to the microstructures;
   c) repels at least one substance from the microstructures;
   d) acts as a barrier to preclude at least one substance from the microstructures; and,
   e) includes at least one of:
      i) a permeable membrane;
      ii) polyethylene;
      iii) polyethylene glycol;
      iv) polyethylene oxide;
      v) zwitterions;
      vi) peptides;
      vii) hydrogels; and,
      viii) self-assembled monolayer.

15. A system according to claim 1, wherein the system includes a housing containing the at least one sensor, the signal generator and at least one electronic processing device, wherein the housing selectively couples to the substrate.

16. A system according to claim 1, wherein the system includes:
   a) a patch including the substrate and the plurality of microstructures; and,
   b) a monitoring device that is configured to:
      i) perform the measurements; and,
      ii) at least one of:
         (1) provide an output indicative of the indicator; and,
         (2) provide a recommendation based on the indicator.

17. A system according to claim 16, wherein the monitoring device is at least one of:
   a) inductively coupled to the patch;
   b) attached to the patch;
   c) brought into contact with the patch when a reading is to be performed.

18. A system according to claim 1, wherein the system includes:
   a) a transmitter that transmits at least one of:
      i) subject data derived from the measured response signals; and,
      ii) measured response signals; and,
   b) a processing system that:
      i) receives subject data derived from the measured response signals; and,
      ii) analyses the subject data to generate at least one indicator, the at least one indicator being at least partially indicative of a health status associated with the subject.

19. A system according to claim 1, wherein the system is configured to perform impedance measurements in a viable epidermis to determine an indicator indicative of at least one of:
   a) a hydration of the subject;
   b) interstitial fluid levels;
   c) a change in interstitial fluid levels;
   d) an ion concentration in interstitial fluid;
   e) a change in an ion concentration in interstitial fluid;
   f) an ion concentration;
   g) a change in an ion concentration;
   h) a total body water;
   i) intracellular fluid levels;
   j) extracellular fluid levels;
   k) plasma water levels;
   l) Fluid volumes; and,
   m) hydration levels.

20. A method for performing fluid level measurements on a biological subject, the method including:
   a) using at least one substrate including a plurality of microstructures to breach a stratum corneum of the biological subject, at least some microstructures including an electrode and wherein the microstructures are conductive and include an insulating layer extending over end of the microstructure proximate the substrate so that at least a tip portion of the microstructure is uncoated and acts as the electrode, and wherein at least some of the microstructures include a shoulder that is configured to abut against the stratum corneum to control a depth of penetration;
   b) using a signal generator operatively connected to at least one microstructure pair to apply an electrical stimulatory signal between microstructures in the at least one microstructure pair, wherein microstructures in the at least one microstructure pair each have respective electrodes in opposition from one microstructure and another microstructure, and wherein the electrical stimulatory signal generates an electric field between the respective electrodes;
   c) using at least one sensor operatively connected to the at least one microstructure pair, the at least one sensor being configured to measure electrical response signals between microstructures in the pair; and,
   d) in one or more electronic processing devices:
      i) determining measured electrical response signals, the response signals being at least partially indicative of a bioimpedance; and,
      ii) performing an analysis at least in part using the measured electrical response signals to determine at least one indicator at least partially indicative of fluid levels in the subject and wherein the system is configured to perform repeated measurements over a time period so that changes in impedance are used to track changes in fluid levels over time.

* * * * *